(12) United States Patent
Heldreth et al.

(10) Patent No.: US 11,883,298 B2
(45) Date of Patent: Jan. 30, 2024

(54) MEDIAL STABILIZED ORTHOPAEDIC KNEE PROSTHESIS

(71) Applicant: DEPUY IRELAND UNLIMITED COMPANY, Ringaskiddy (IE)

(72) Inventors: Mark A. Heldreth, Warsaw, IN (US); Travis D. Bennett, Huntington, IN (US); Amitkumar M. Mane, South Whitley, IN (US); Michael J. Rock, Leeds (GB); Thomas E. Wogoman, Warsaw, IN (US); Stephen E. White, Fort Wayne, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 70 days.

(21) Appl. No.: 17/372,443

(22) Filed: Jul. 10, 2021

(65) Prior Publication Data
US 2022/0008208 A1 Jan. 13, 2022

Related U.S. Application Data

(60) Provisional application No. 63/050,744, filed on Jul. 10, 2020.

(51) Int. Cl.
*A61F 2/38* (2006.01)
*A61F 2/30* (2006.01)

(52) U.S. Cl.
CPC .......... *A61F 2/389* (2013.01); *A61F 2/3859* (2013.01); *A61F 2002/30131* (2013.01); *A61F 2002/30621* (2013.01); *A61F 2002/3863* (2013.01)

(58) Field of Classification Search
CPC .................. A61F 2/389; A61F 2/3859; A61F 2002/30131
See application file for complete search history.

(56) References Cited

U.S. PATENT DOCUMENTS

| 3,748,662 A | 7/1973 | Helfet |
| 5,219,362 A | 6/1993 | Tuke et al. |

(Continued)

FOREIGN PATENT DOCUMENTS

| EP | 1604623 A1 | 12/2005 |
| EP | 2572677 A1 | 3/2013 |

(Continued)

OTHER PUBLICATIONS

Advance, Medial-Pivot and Stemmed Medial-Pivot Knee Systems, Wright Medical Technology, Inc., 2010, 12 pages.

(Continued)

*Primary Examiner* — Jason-Dennis N Stewart
(74) *Attorney, Agent, or Firm* — BARNES & THORNBURG LLP

(57) ABSTRACT

An orthopaedic knee prosthesis includes a tibial insert and a femoral component configured to articulate on the tibial insert. The tibial insert includes a lateral articular surface and medial articular surface that is asymmetrically shaped relative to the lateral articular surface. The medial articular surface is shaped to reduce anterior translation of a medial condyle of the femoral component, while the lateral articular surface is shaped to allow a lateral condyle of the femoral component to pivot, relative to the medial articular surface, along an arcuate articular path. Additionally, one or both condyles of the femoral component may include a femoral articular surface having a curved femoral surface section defined by a continuously decreasing radius of curvature.

20 Claims, 29 Drawing Sheets

(56) References Cited

U.S. PATENT DOCUMENTS

| | | | |
|---|---|---|---|
| 5,370,701 A | 12/1994 | Finn | |
| 5,682,886 A | 11/1997 | Delp et al. | |
| 5,735,856 A | 4/1998 | Mccue et al. | |
| 5,871,018 A | 2/1999 | Delp et al. | |
| 5,964,808 A | 10/1999 | Blaha et al. | |
| 6,013,103 A | 1/2000 | Kaufman et al. | |
| 6,986,791 B1 | 1/2006 | Metzger | |
| 7,261,740 B2 | 8/2007 | Tuttle et al. | |
| 8,187,335 B2 | 5/2012 | Wyss et al. | |
| 8,192,498 B2 | 6/2012 | Wagner et al. | |
| 8,211,181 B2 | 7/2012 | Walker | |
| 8,236,061 B2 | 8/2012 | Heldreth et al. | |
| 8,292,964 B2 | 10/2012 | Walker | |
| 8,328,873 B2 | 12/2012 | Metzger et al. | |
| 8,480,752 B2 | 7/2013 | Dun | |
| 8,628,579 B2 | 1/2014 | Ries et al. | |
| 8,784,496 B2 | 7/2014 | Wagner et al. | |
| 8,795,380 B2 | 8/2014 | Heldreth et al. | |
| 8,828,086 B2 | 9/2014 | Williams et al. | |
| 8,834,575 B2 | 9/2014 | Wyss et al. | |
| 8,915,965 B2 | 12/2014 | Komistek | |
| 9,101,393 B2 | 8/2015 | Jordan et al. | |
| 9,101,394 B2 | 8/2015 | Arata et al. | |
| 9,168,145 B2 | 10/2015 | Wyss et al. | |
| 9,216,088 B2 | 12/2015 | Wasielewski | |
| 9,220,601 B2 | 12/2015 | Williams et al. | |
| 9,299,138 B2 | 3/2016 | Zellner et al. | |
| 9,320,616 B2 | 4/2016 | Samuelson et al. | |
| 9,320,624 B2 | 4/2016 | Shin | |
| 9,326,864 B2 | 5/2016 | Wyss et al. | |
| 9,402,726 B2 | 8/2016 | Linderman et al. | |
| 9,452,053 B2 | 9/2016 | Wagner et al. | |
| 9,539,099 B2 | 1/2017 | Heldreth et al. | |
| 9,603,711 B2 | 3/2017 | Bojarski et al. | |
| 9,668,870 B2 | 6/2017 | Wasielewski | |
| 9,788,954 B2 | 10/2017 | Parisi et al. | |
| 9,820,821 B2 | 11/2017 | Aram et al. | |
| 9,861,446 B2 | 1/2018 | Lang | |
| 9,931,216 B2 | 4/2018 | Williams et al. | |
| 9,937,049 B2 | 4/2018 | Wyss et al. | |
| 9,962,264 B2 | 5/2018 | Komistek | |
| 10,080,663 B2 | 9/2018 | Wasielewski | |
| 10,159,530 B2 | 12/2018 | Lang | |
| 10,179,051 B2 | 1/2019 | Heldreth et al. | |
| 10,179,052 B2 | 1/2019 | Clary et al. | |
| 10,195,056 B2 | 2/2019 | Wogoman et al. | |
| 10,201,429 B2 | 2/2019 | Enomoto et al. | |
| 10,265,180 B2 | 4/2019 | Wyss et al. | |
| 10,278,827 B2 * | 5/2019 | Drury | A61F 2/389 |
| 10,478,307 B2 | 11/2019 | Wasielewski et al. | |
| 10,543,098 B2 | 1/2020 | Williams et al. | |
| 10,729,551 B2 | 8/2020 | Heldreth et al. | |
| 10,849,760 B2 | 12/2020 | Wyss et al. | |
| 11,141,291 B2 | 10/2021 | Wogoman et al. | |
| 11,229,485 B2 | 1/2022 | Otto et al. | |
| 11,324,598 B2 | 5/2022 | Dai et al. | |
| 11,337,823 B2 | 5/2022 | Williams et al. | |
| 11,364,081 B2 | 6/2022 | Dees, Jr. | |
| 11,369,478 B2 | 6/2022 | Wyss et al. | |
| 11,612,488 B2 | 3/2023 | Wogoman et al. | |
| 2003/0009228 A1 | 1/2003 | Figueroa et al. | |
| 2005/0107886 A1 | 5/2005 | Crabtree et al. | |
| 2005/0278035 A1 | 12/2005 | Wyss et al. | |
| 2008/0262812 A1 | 10/2008 | Arata et al. | |
| 2008/0269596 A1 | 10/2008 | Revie et al. | |
| 2009/0088860 A1 | 4/2009 | Romeis et al. | |
| 2009/0204221 A1 | 8/2009 | Walker | |
| 2010/0036499 A1 | 2/2010 | Pinskerova | |
| 2010/0286788 A1 | 11/2010 | Komistek | |
| 2012/0197409 A1 | 8/2012 | Mckinnon et al. | |
| 2012/0265496 A1 | 10/2012 | Mahfouz | |
| 2012/0310246 A1 | 12/2012 | Belcher et al. | |
| 2012/0310362 A1 | 12/2012 | Li et al. | |
| 2013/0006373 A1 | 1/2013 | Wyss et al. | |
| 2013/0197653 A1 | 8/2013 | Hawkins et al. | |
| 2013/0197654 A1 | 8/2013 | Samuelson et al. | |
| 2013/0325021 A1 | 12/2013 | Sordelet et al. | |
| 2014/0039635 A1 | 2/2014 | Bartels et al. | |
| 2014/0081412 A1 | 3/2014 | Metzger | |
| 2014/0277534 A1 | 9/2014 | Wasielewski | |
| 2014/0330388 A1 | 11/2014 | Mizuguchi et al. | |
| 2015/0032215 A1 | 1/2015 | Slamin et al. | |
| 2015/0088264 A1 | 3/2015 | Li et al. | |
| 2015/0190235 A1 | 7/2015 | Mcminn | |
| 2016/0030184 A1 | 2/2016 | Whiteside | |
| 2016/0317312 A1 | 11/2016 | Bojarski et al. | |
| 2017/0020674 A1 | 1/2017 | Walker | |
| 2017/0079801 A1 | 3/2017 | Drury et al. | |
| 2017/0128219 A1 | 5/2017 | Metzger et al. | |
| 2017/0189191 A1 | 7/2017 | Heldreth et al. | |
| 2017/0189195 A1 | 7/2017 | Blaha | |
| 2017/0266013 A1 | 9/2017 | Enomoto et al. | |
| 2017/0340389 A1 | 11/2017 | Otto et al. | |
| 2019/0209331 A1 | 7/2019 | Varadarajan et al. | |
| 2019/0209333 A1 | 7/2019 | Drury et al. | |
| 2019/0240032 A1 | 8/2019 | Wasielewski et al. | |
| 2020/0069432 A1 | 3/2020 | Mcminn | |
| 2020/0085583 A1 | 3/2020 | Hodge | |
| 2020/0100902 A1 | 4/2020 | Wasielewski et al. | |
| 2020/0214843 A1 | 7/2020 | Radermacher et al. | |
| 2020/0246149 A1 | 8/2020 | Matyas et al. | |
| 2022/0079678 A1 | 3/2022 | Duxbury et al. | |

FOREIGN PATENT DOCUMENTS

| | | |
|---|---|---|
| EP | 3854353 A1 | 7/2021 |
| WO | 9723172 A2 | 7/1997 |
| WO | 2010151564 A1 | 12/2010 |
| WO | 2011075697 A2 | 6/2011 |
| WO | 2014143538 A1 | 9/2014 |
| WO | 2017155995 A1 | 9/2017 |
| WO | 2017160889 A1 | 9/2017 |
| WO | 2017204832 A1 | 11/2017 |

OTHER PUBLICATIONS

Persona, The Personalized Knee, Surgical Technique, Zimmer Biomet, 2018, 76 pages.

Persona, The Personalized Knee, Medial Congruent Bearing Design Rationale, Zimmer Biomet, 2017, 20 pages.

eMP, Evolution, Medial-Pivot Knee System, The ACL-PCL Substituting Knee, Key Aspects, MicroPort Orthopaedics, 2015, 6 pages.

Evolution, Medial-Pivot Knee System, Surgical Technique, Distal Cut First, MicroPort Orthopaedics, 2014, 52 pages.

PCT Search Report & Written Opinion prepared for PCT/EP2021/069244, dated Nov. 1, 2022, 24 pages.

Smith & Nephew, Journey II TKA Total Knee System—Combined Technique for Journey II BCS and Journey II CR, 68 pages.

International SR and Written Opinion for International App. No. PCT/US2020/022123, dated May 8, 2020, 13 Pages.

International SR and Written Opinon for International App. No. PCT/US2020/022119, dated May 27, 2020, 11 Pages.

International SR for International App. No. PCT/IB20/54105, dated Aug. 31, 2020, 3 Pages.

PCT International SR for International App. No. PCT/IB20/54110, dated Aug. 12, 2020, 3 Pages.

PCT International SR and Written Opinion for International App. No. PCT/EP2020/075246, dated Mar. 15, 2022, 11 Pages.

* cited by examiner

| Component Size | RAY LENGTH EQUATION |
|---|---|
| 1 | R=29.383391+0.0166694187*θ-0.000270023780*θ²-0.00000124837*θ³ |
| 2 | R=30.470577+0.0166694187*θ-0.000270023780*θ²-0.00000124837*θ³ |
| 3 | R=31.597988+0.0166694187*θ-0.000270023780*θ²-0.00000124837*θ³ |
| 4 | R=32.767114+0.0166694187*θ-0.000270023780*θ²-0.00000124837*θ³ |
| 5 | R=33.979497+0.0166694187*θ-0.000270023780*θ²-0.00000124837*θ³ |
| 6 | R=35.236738+0.0166694187*θ-0.000270023780*θ²-0.00000124837*θ³ |
| 7 | R=36.540498+0.0166694187*θ-0.000270023780*θ²-0.00000124837*θ³ |
| 8 | R=37.892496+0.0166694187*θ-0.000270023780*θ²-0.00000124837*θ³ |
| 9 | R=39.294518+0.0166694187*θ-0.000270023780*θ²-0.00000124837*θ³ |
| 10 | R=40.748416+0.0166694187*θ-0.000270023780*θ²-0.00000124837*θ³ |

Origin Distance column: 4.008, 3.898, 3.722, 3.629, 3.468, 3.288, 3.088, 2.866, 2.623, 2.356

Fig. 7

MEDIAL STABILIZED ORTHOPAEDIC KNEE PROSTHESIS

CROSS-REFERENCE TO RELATED APPLICATIONS

This application claims priority under 35 U.S.C. § 119 to U.S. Provisional Patent Application Ser. No. 63/050,744, entitled "ORTHOPAEDIC KNEE PROSTHESIS SYSTEM AND METHODS FOR USING SAME," which was filed on Jul. 10, 2020 and is expressly incorporated by reference into the present application.

TECHNICAL FIELD

The present disclosure relates to orthopaedic knee prosthesis systems and, more specifically, to orthopaedic knee prosthesis, instrumentation, and methods for total knee arthroplasty procedures.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial insert in some cases wherein it is desirable to limit the movement of the knee prosthesis, such as when significant soft tissue damage or loss is present. Alternatively, the knee prosthesis may include a "mobile" tibial insert in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior-stabilized knee prosthesis may be used to provide additional support and/or control at later degrees of flexion. Alternatively, if the posterior cruciate ligament is intact, a cruciate-retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

SUMMARY

According to one aspect, a tibial insert includes a lateral articular surface and a medial articular surface. The lateral articular surface is configured to articulate with a lateral condyle of a femoral component and includes an arcuate articular path extending in an anterior-posterior direction. The arcuate articular path is defined by a plurality of points on the lateral articular surface and, when the tibial insert is viewed in a cross-sectional medial-lateral plane at each point, each point defines a distal-most point of the lateral articular surface in the corresponding cross-sectional medial-lateral plane. The lateral articular surface has a cross-sectional concave curvature orthogonal to the arcuate articular path, the cross-sectional concave curvature being uniform at each of the plurality of points. The medial articular surface is configured to articulate with a medial condyle of the femoral component. The medial articular surface is asymmetrically shaped relative to the lateral articular surface and has a coronal concave curvature that is non-uniform in the anterior-posterior direction.

In an embodiment, the medial articular surface includes a medial dwell point that defines a distal-most point of the medial articular surface. The coronal concave curvature of the medial articular surface is non-uniform anterior of the medial dwell point and uniform posterior of the medial dwell point.

In an embodiment, the arcuate articular path when viewed in a cross-sectional plane has a curvature that includes a semi-planar section, an anterior curved section located anterior of the planar section, and a plurality of posterior curved sections located posterior of the planar section. The semi-planar section defines a lateral dwell region that defines a distal-most area of the lateral articular surface. In an embodiment, each posterior curved section is defined by a corresponding radius of curvature, wherein the radii of curvature of the plurality of posterior curved sections decrease posteriorly.

In an embodiment, the plurality of posterior curved sections includes a first posterior curved section adjacent to a posterior-most end of the planar section and a second posterior curved section adjacent to the first posterior curved section, wherein a radius of curvature of the first posterior curved section is greater than a radius of curvature of the second posterior curved section. In an embodiment, the anterior curved section is defined by a corresponding radius of curvature that is (i) less than the radius of curvature of the first posterior curved section and (ii) greater than the radius of curvature of the second posterior curved section. In an embodiment, the anterior curved section extends for an arc length in the range of 33.5 degrees to 34.4 degrees, the first posterior curved section extends for about 3.4 degrees, and the second posterior curved section extends for an arc length in the range of 13.2 degrees to 13.7 degrees.

In an embodiment, the medial articular surface includes a sagittal concave curvature, when viewed in a sagittal plane, that is defined by a plurality of curved sections and a medial dwell point that defines a distal-most point of the medial articular surface, wherein the medial dwell point is located on the sagittal concave curvature. In an embodiment, the plurality of curved sections includes a first curved section adjacent to the medial dwell point and extending posterior therefrom and a second curved section adjacent the medial dwell point and extending anterior therefrom, wherein a radius of curvature of the first curved section is greater than a radius of curvature of the second curved section. In an embodiment, the first curved section extends for an arc length of in the range of 15.9 degrees to 17.4 degrees and the second curved section extends for about 5.2 degrees.

In an embodiment, the plurality of curved sections includes a third curved section adjacent to the second curved section and extending anterior therefrom, a fourth curved section adjacent to the third curved section and extending anterior therefrom, and a fifth curved section adjacent the fourth curved section and extending anterior therefrom. A radius of curvature of the third curved section is less that the radius of curvature of the second curved section, less than a radius of curvature of the fourth curved section, and less than a radius of the fifth radius of curvature. In an embodiment, the third curved section extends for an arc length in the range of 14.8 degrees to 24.8 degrees, the fourth curved section extends for an arc length in the range of 10.7 degrees to 20.7 degrees, and the fifth radius of curvature extends for an arc length in the range of 0.2 degrees to 6.3 degrees.

In an embodiment, the coronal concave curvature of the medial articular surface is defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other. In an embodiment, the first coronal curvature is defined by a coronal curved section that extends for an arc length in the range of 18.6 degrees to 26.8 degrees medially from the medial dwell point and for about 25.0 degrees laterally from the medial dwell point. In an embodiment, the second coronal curvature crosses the sagittal concave curvature of the medial articular surface at an anterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section. In an embodiment, a radius of curvature of the first coronal curved section of the second coronal curvature is less than a radius of curvature of the second coronal curved section of the second coronal curvature. In an embodiment, the first coronal curved of the second coronal curvature section extends for an arc length in the range of 14.7 degrees to 15.7 degrees and the second coronal curved section of the second coronal curvature extends for an arc length in the range of 20.1 degrees to 28.5 degrees.

In an embodiment, the third coronal curvature crosses the sagittal concave curvature of the medial articular surface at an anterior-most point of the fourth curved section of the plurality of curved sections that define the sagittal concave curvature of the medial articular surface. The third coronal curvature is defined by a planar section having a medial end and a lateral end, a first coronal curved section extending from the medial end of the planar section, and a second coronal curved section extending from the lateral end of the planar section. In an embodiment, the planar section of the third coronal curvature is angled about 6 degrees relative to a bottom surface of the tibial insert. In an embodiment, the first coronal curved section of the third coronal curvature extends for an arc length in the range of 0.3 degrees to 0.9 degrees and the second coronal curved section of the third coronal curvature extends for an arc length in the range of 16.4 degrees to 24.7 degrees.

In an embodiment, the tibial insert further includes an anterior sidewall and a posterior sidewall opposite the anterior side, wherein a distance between the anterior sidewall and the posterior sidewall defines an anterior-posterior length of the tibial insert. The medial articular surface includes a medial dwell point that defines a distal-most point of the medial articular surface, wherein the medial dwell point is located about 63.3% of the anterior-posterior length from the anterior end.

In an embodiment, the medial articular surface includes a medial dwell point that defines a distal-most point of the medial articular surface, and the arcuate articular path of the lateral articular surface, when viewed in a transverse plane, is defined by a radius of curvature having an origin on the medial dwell point.

In an embodiment, the tibial insert further includes a first portion of a locking mechanism located on a bottom surface of the tibial insert. The first portion of the locking mechanism is configured to mate with a second portion of the locking mechanism located on a tibial base to secure the tibial insert to the tibial base.

According to another aspect, a tibial insert includes a lateral articular surface and a medial articular surface. The lateral articular surface is configured to articulate with a lateral condyle of a femoral component and includes an arcuate articular path extending in an anterior-posterior direction. The arcuate articular path when viewed in a cross-section plane has a curvature that includes a semi-planar section, wherein the semi-planar section defines a distal-most area of the lateral articular surface. The medial articular surface is configured to articulate with a medial condyle of the femoral component. The medial articular surface is asymmetrically shaped relative to the lateral articular surface and includes a medial dwell point that defines a distal-most point of the medial condyle surface. The medial dwell point is located on the medial condyle surface (i) between a first imaginary medial-lateral bisecting line of the tibial insert that includes an anterior-most end of the planar section of the sagittal curvature of the lateral articular surface and a second imaginary medial-lateral bisecting line of the tibial insert that includes a posterior-most end of the planar section of the sagittal curvature of the lateral articular surface and (ii) posterior to an anterior-posterior midpoint of the planar section of the sagittal curvature of the lateral articular surface.

In an embodiment, the tibial insert further includes an anterior sidewall and a posterior sidewall opposite the anterior side, wherein a distance between the anterior sidewall and the posterior sidewall defines an anterior-posterior length of the tibial insert. The medial dwell point is located about 63.3% of the anterior-posterior length from the anterior end.

In an embodiment, the medial articular surface has a coronal concave curvature that is non-uniform anterior of the medial dwell point and uniform posterior of the medial dwell point.

In an embodiment, the curvature of the arcuate articular path, when viewed in the cross-section plane, further includes an anterior curved section located anterior of the semi-planar section and a plurality of posterior curved sections located posterior of the semi-planar section. In an embodiment, each posterior curved section is defined by a corresponding radius of curvature, and the radii of curvature of the plurality of posterior curved sections decrease posteriorly. In an embodiment, the plurality of posterior curved sections includes a first posterior curved section adjacent to the posterior-most end of the planar section and a second posterior curved section adjacent to the first posterior curved section, wherein a radius of curvature of the first posterior curved section is greater than a radius of curvature of the second posterior curved section. In an embodiment, the anterior curved section is defined by a corresponding radius of curvature that is (i) less than the radius of curvature of the first posterior curved section and (ii) greater than radius of curvature of the second posterior curved section. In an embodiment, the anterior curved section extends for an arc length in the range of 33.5 degrees to 34.4 degrees, the first posterior curved section extends for about 3.4 degrees, and the second posterior curved section extends for an arc length in the range of 13.2 degrees to 13.7 degrees.

In an embodiment, the medial articular surface includes a sagittal concave curvature, when viewed in a sagittal plane, that is defined by a plurality of curved sections, wherein the medial dwell point is located on the sagittal concave curvature. In an embodiment, the plurality of curved sections includes a first curved section adjacent to the medial dwell point and extending posterior therefrom and a second curved section adjacent the medial dwell point and extending anterior therefrom, wherein a radius of curvature of the first curved section is greater than a radius of curvature of the second curved section. In an embodiment, the first curved section extends for an arc length of in the range of 15.9 degrees to 17.4 degrees and the second curved section extends for about 5.2 degrees.

In an embodiment, the plurality of curved sections includes a third curved section adjacent to the second curved section and extending anterior therefrom, a fourth curved section adjacent to the third curved section and extending anterior therefrom, and a fifth curved section adjacent the fourth curved section and extending anterior therefrom, wherein a radius of curvature of the third curved section is less that the radius of curvature of the second curved section, less than a radius of curvature of the fourth curved section, and less than a radius of the fifth radius of curvature. In an embodiment, the third curved section extends for an arc length in the range of 14.8 degrees to 24.8 degrees, the fourth curved section extends for an arc length in the range of 10.7 degrees to 20.7 degrees, and the fifth radius of curvature extends for an arc length in the range of 0.2 degrees to 6.3 degrees.

In an embodiment, the medial articular surface has a coronal curvature defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other. In an embodiment, the first coronal curvature is defined by a coronal curved section that extends for an arc length in the range of 18.6 degrees to 26.8 degrees medially from the medial dwell point and for about 25.0 degrees laterally from the medial dwell point.

In an embodiment, the second coronal curvature crosses the sagittal concave curvature of the medial articular surface at an anterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section. In an embodiment, a radius of curvature of the first coronal curved section of the second coronal curvature is less than a radius of curvature of the second coronal curved section of the second coronal curvature. In an embodiment, the first coronal curved of the second coronal curvature section extends for an arc length in the range of 14.7 degrees to 15.7 degrees and the second coronal curved section of the second coronal curvature extends for an arc length in the range of 20.1 degrees to 28.5 degrees.

In an embodiment, the third coronal curvature crosses the sagittal concave curvature of the medial articular surface at an anterior-most point of the fourth curved section of the plurality of curved sections that define the sagittal concave curvature of the medial articular surface, wherein the third coronal curvature is defined by a planar section having a medial end and a lateral end, a first coronal curved section extending from the medial end of the planar section, and a second coronal curved section extending from the lateral end of the planar section. In an embodiment, the planar section of the third coronal curvature is angled about 6 degrees relative to a bottom surface of the tibial insert. In an embodiment, the first coronal curved section of the third coronal curvature extends for an arc length in the range of 0.3 degrees to 0.9 degrees and the second coronal curved section of the third coronal curvature extends for an arc length in the range of 16.4 degrees to 24.7 degrees.

In an embodiment, the arcuate articular path, when viewed in a transverse plane, is defined by a radius of curvature having an origin on the medial dwell point.

In an embodiment, the tibial insert further includes a first portion of a locking mechanism located on a bottom surface of the tibial insert. The first portion of the locking mechanism is configured to mate with a second portion of the locking mechanism located on a tibial base to secure the tibial insert to the tibial base.

According to another aspect, a tibial insert includes a lateral articular surface configured to articulate with a lateral condyle of a femoral component and a medial articular surface configured to articulate with a medial condyle of the femoral component. The lateral articular surface includes an arcuate articular path extending in an anterior-posterior direction, a lateral dwell point that defines a distal-most point on the lateral articular surface located on the arcuate articular path, and an anterior lateral lip, wherein an inferior-superior distance between the lateral dwell point and a superior-most point of the anterior lateral lip defines a lip height of the anterior lateral lip. The medial articular surface is asymmetrically shaped relative to the lateral articular surface and includes a medial dwell point that defines a distal-most point on the medial articular surface and an anterior medial lip, wherein an inferior-superior distance between the medial dwell point and a superior-most point on the medial lateral lip defines a lip height of the anterior medial lip. The lip height of the anterior medial lip is greater than the lip height of the anterior lateral lip, and a ratio of the lip height of the anterior medial lip to an anterior-posterior distance between an anterior sidewall of the medial articular surface and a posterior sidewall of the medial articular surface is in the range of 18.9% to 20.9%.

In an embodiment, the medial articular surface has a coronal concave curvature that is non-uniform anterior of the medial dwell point and uniform posterior of the medial dwell point.

In an embodiment, the arcuate articular path, when viewed in the cross-section plane, has curvature that includes a semi-planar section, an anterior curved section located anterior of the planar section, and a plurality of posterior curved sections located posterior of the planar section. The lateral dwell point is located on the semi-planar section.

In an embodiment, each posterior curved section is defined by a corresponding radius of curvature, wherein the radii of curvature of the plurality of posterior curved sections decrease posteriorly.

In an embodiment, the plurality of posterior curved sections includes a first posterior curved section adjacent to a posterior-most end of the planar section and a second posterior curved section adjacent to the first posterior curved section, wherein a radius of curvature of the first posterior curved section is greater than a radius of curvature of the second posterior curved section. In an embodiment, an anterior curved section is defined by a corresponding radius of curvature that is (i) less than the radius of curvature of the first posterior curved section and (ii) greater than radius of curvature of the second posterior curved section. In an embodiment, the anterior curved section extends for an arc length in the range of 33.5 degrees to 34.4 degrees, the first posterior curved section extends for about 3.4 degrees, and the second posterior curved section extends for an arc length in the range of 13.2 degrees to 13.7 degrees.

In an embodiment, the medial articular surface includes a sagittal concave curvature, when viewed in a sagittal plane, that is defined by a plurality of curved sections, wherein the medial dwell point is located on the sagittal concave curvature. In an embodiment, the plurality of curved sections includes a first curved section adjacent to the medial dwell point and extending posterior therefrom and a second curved section adjacent the medial dwell point and extending anterior therefrom, wherein a radius of curvature of the first curved section is greater than a radius of curvature of the second curved section. In an embodiment, the first curved section extends for an arc length of in the range of 15.9 degrees to 17.4 degrees and the second curved section extends for about 5.2 degrees.

In an embodiment, the plurality of curved sections includes a third curved section adjacent to the second curved section and extending anterior therefrom, a fourth curved section adjacent to the third curved section and extending anterior therefrom, and a fifth curved section adjacent the fourth curved section and extending anterior therefrom, wherein a radius of curvature of the third curved section is less that the radius of curvature of the second curved section, less than a radius of curvature of the fourth curved section, and less than a radius of the fifth radius of curvature. In an embodiment, the third curved section extends for an arc length in the range of 14.8 degrees to 24.8 degrees, the fourth curved section extends for an arc length in the range of 10.7 degrees to 20.7 degrees, and the fifth radius of curvature extends for an arc length in the range of 0.2 degrees to 6.3 degrees.

In an embodiment, the medial articular surface has a coronal curvature defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other. In an embodiment, the first coronal curvature is defined by a coronal curved section that extends for an arc length in the range of 18.6 degrees to 26.8 degrees medially from the medial dwell point and for about 25.0 degrees laterally from the medial dwell point.

In an embodiment, the second coronal curvature crosses the sagittal concave curvature of the medial articular surface at an anterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section. In an embodiment, a radius of curvature of the first coronal curved section of the second coronal curvature is less than a radius of curvature of the second coronal curved section of the second coronal curvature. In an embodiment, the first coronal curved of the second coronal curvature section extends for an arc length in the range of 14.7 degrees to 15.7 degrees and the second coronal curved section of the second coronal curvature extends for an arc length in the range of 20.1 degrees to 28.5 degrees.

In an embodiment, the third coronal curvature crosses the sagittal concave curvature of the medial articular surface at an anterior-most point of the fourth curved section of the plurality of curved sections that define the sagittal concave curvature of the medial articular surface, wherein the third coronal curvature is defined by a planar section having a medial end and a lateral end, a first coronal curved section extending from the medial end of the planar section, and a second coronal curved section extending from the lateral end of the planar section. In an embodiment, the planar section of the third coronal curvature is angled about 6 degrees relative to a bottom surface of the tibial insert. In an embodiment, the first coronal curved section of the third coronal curvature extends for an arc length in the range of 0.3 degrees to 0.9 degrees and the second coronal curved section of the third coronal curvature extends for an arc length in the range of 16.4 degrees to 24.7 degrees.

In an embodiment, the tibial insert further includes an anterior side and a posterior side opposite the anterior side. A distance between the anterior side and the posterior side defines an anterior-posterior length of the tibial insert. The medial dwell point is located about 63.3% of the anterior-posterior length from the anterior end. In an embodiment, the arcuate articular path of the lateral articular surface, when viewed in a transverse plane, is defined by a radius of curvature having an origin on the medial dwell point.

In an embodiment, the tibial insert further includes a first portion of a locking mechanism located on a bottom surface of the tibial insert. The first portion of the locking mechanism is configured to mate with a second portion of the locking mechanism located on a tibial base to secure the tibial insert to the tibial base.

According to yet another aspect, an orthopaedic knee prosthesis includes a femoral component having a lateral condyle and a medial condyle and a tibial insert having a lateral articular surface configured to articulate with the lateral condyle of the femoral component and a medial articular surface configured to articulate with the medial condyle of the femoral component. The medial condyle includes a femoral articular surface defined by a plurality of curved femoral surface sections that includes a first curved femoral surface section defined by a continually decreasing radius of curvature. The medial articular surface is asymmetrically shaped relative to the lateral articular surface and includes a medial dwell point that defines a distal-most point on the medial articular surface. The medial condyle contacts the medial dwell point at a first contact point on the first curved femoral surface section at a first degree of flexion and contacts the medial dwell point at a second contact point on the first curved femoral surface section at a second degree of flexion, wherein the second contact point is posterior of the first contact point and wherein the second degree of flexion is greater than the first degree of flexion. The medial articular surface includes a sagittal concave curvature that has a first sagittal conformity with the medial condyle at a location anterior to dwell point at the first degree of flexion and a second sagittal conformity with the medial condyle at the location anterior to the dwell point at the second degree of flexion, wherein the second sagittal conformity is greater than the first sagittal conformity to reduce anterior translation of the medial condyle at the second degree of flexion.

In an embodiment, the medial condyle of femoral component includes a sagittal convex curvature, and a sagittal conformity between the sagittal concave curvature of the medial articular surface and sagittal concave curvature of the medial condyle is greater at a first degree of flexion of the femoral condyle than at extension. In an embodiment, the first degree of flexion is about 30 degrees.

In an embodiment, the medial articular surface includes a coronal concave curvature and a coronal conformity between the coronal concave curvature and the medial condyle at the degree of flexion is greater at the medial dwell point of the medial articular surface than at the location on the medial articular surface that is anterior of the medial dwell point. In an embodiment, the medial articular surface is non-uniform anterior of the medial dwell point and uniform posterior of the medial dwell point.

In an embodiment, the medial condyle and the medial articular surface are more conforming with each other than the lateral condyle and the lateral articular surface.

In an embodiment, the medial articular surface includes a coronal concave curvature and a coronal conformity between the coronal concave curvature and the medial condyle is greater when the femoral component is positioned at extension than when the femoral component is positioned at a later degree of flexion.

In an embodiment, the lateral articular surface includes an arcuate articular path that when viewed in a cross-section plane has a curvature that includes a planar section, an anterior curved section located anterior of the semi-planar section, and a plurality of posterior curved sections located posterior of the planar section. the semi-planar section defines a distal-most area of the lateral articular surface. In an embodiment, each posterior curved section is defined by a corresponding radius of curvature, and wherein the radii of curvature of the plurality of posterior curved sections decrease posteriorly.

In an embodiment, the sagittal concave curvature of the medial articular surface, when viewed in a sagittal plane, includes a plurality of curved sections and wherein the medial dwell point is located on the sagittal concave curvature. The plurality of curved sections includes a first curved section adjacent to the medial dwell point and extending posterior therefrom, a second curved section adjacent the medial dwell point and extending anterior therefrom, a third curved section adjacent to the second curved section and extending anterior therefrom, a fourth curved section adjacent to the third curved section and extending anterior therefrom, and a fifth curved section adjacent the fourth curved section and extending anterior therefrom. A radius of curvature of the first curved section is greater than a radius of curvature of the second curved section and wherein a radius of curvature of the third curved section is less that the radius of curvature of the second curved section, less than a radius of curvature of the fourth curved section, and less than a radius of the fifth radius of curvature.

In an embodiment, the medial articular surface includes a coronal concave curvature that is defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other. In an embodiment, the second coronal curvature crosses the sagittal concave curvature of the medial articular surface at an anterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section, and wherein a radius of curvature of the first coronal curved section is less than a radius of curvature of the second coronal curved section. In an embodiment, the third coronal curvature crosses the sagittal concave curvature of the medial articular surface at an anterior-most point of the fourth curved section of the plurality of curved sections that define the sagittal concave curvature of the medial articular surface, wherein the third coronal curvature is defined by a planar section having a medial end and a lateral end, a first coronal curved section extending from the medial end of the planar section, and a second coronal curved section extending from the lateral end of the planar section.

In an embodiment, the tibial insert further includes a first portion of a locking mechanism located on a bottom surface of the tibial insert. The first portion of the locking mechanism is configured to mate with a second portion of the locking mechanism located on a tibial base to secure the tibial insert to the tibial base.

In an embodiment, a distal-most point of the femoral articular surface when the femoral component is in extension defines zero degrees of flexion, and the first curved femoral surface section extends from a first degree of flexion of about 5 degrees to a second degree of flexion of about 65 degrees. In an embodiment, the first curved femoral surface section is defined by a plurality of rays extending from a common origin to a corresponding point on the second curved femoral surface section. Each ray has a length defined by the following polynomial equation: $r_\theta=(a+(b*\theta)+(c*\theta^2)+(d*\theta^3))$, wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30<b<0.00$, $0.00<b<0.30$, and $b=0$, wherein when b is in the range of $-0.30<b<0.00$, (i) c is a coefficient value between 0.00 and 0.012 and (ii) d is a coefficient value between $-0.00015$ and 0.00, wherein when b is in the range of $0<b<0.30$, (i) c is a coefficient value between $-0.010$ and 0.00 and (ii) d is a coefficient value between $-0.00015$ and 0.00, and wherein when b is equal to 0, (i) c is a coefficient value in a range selected from the group consisting of: $-0.0020<c<0.00$ and $0.00<c<0.0025$ and (ii) d is a coefficient value between $-0.00015$ and 0.00.

In an embodiment, the plurality of curved femoral surface sections includes a second curved femoral surface section posteriorly adjacent the first curved femoral section, wherein the second curved femoral surface section is defined by a constant radius of curvature greater than a posterior-most radii of curvature of the first curved femoral surface section. In an embodiment, the second curved femoral surface section extends from a first degree of flexion of about 65 degrees to a second degree of flexion of about 90.

According to another aspect, an orthopaedic knee prosthesis includes a femoral component having a lateral condyle and a medial condyle and a tibial insert having a lateral articular surface configured to articulate with the lateral condyle of the femoral component and a medial articular surface configured to articulate with the medial condyle of the femoral component. The medial condyle includes a femoral articular surface defined by a plurality of curved femoral surface sections that includes a first curved femoral surface section and a second curved femoral surface section posteriorly adjacent the first curved femoral surface section, wherein the first curved femoral surface section is defined by a continually decreasing radius of curvature and the second curved femoral surface section is defined by a constant radius of curvature greater than a posterior-most radii of curvature of the first curved femoral surface section. The medial articular surface is asymmetrically shaped relative to the lateral articular surface and includes a medial dwell point that defines a distal-most point on the medial articular surface. The medial condyle (i) contacts the medial dwell point at a first contact point on the first curved femoral surface section at a first degree of flexion, the first contact point being defined by the posterior-most radii of curvature of the first curved femoral surface section and (ii) contacts the medial dwell point at a second contact point on the second curved femoral surface section at a second degree of flexion greater than the first degree of flexion, the second contact point being defined by the constant radius of curvature of the second curved femoral surface section. An inferior-superior distance between the medial dwell point and an origin of the constant radius of curvature of the second curved femoral surface section at the second degree of flexion is greater than an inferior-superior distance between the medial dwell point and an origin of the posterior-most radii of curvature of the first curved femoral surface section at the first degree of flexion.

In an embodiment, the medial condyle of femoral component includes a sagittal convex curvature and the medial articular surface includes a sagittal concave curvature, wherein a sagittal conformity between the sagittal concave curvature of the medial articular surface and sagittal concave curvature of the medial condyle is greater at a first degree of flexion of the femoral condyle than at extension. In an embodiment, the first degree of flexion is about 30 degrees.

In an embodiment, the medial articular surface includes a sagittal concave curvature, wherein at the medial dwell point the sagittal concave curvature has a first sagittal conformity with the medial condyle at a first degree of flexion of the femoral component, wherein at a location on the medial articular surface that is anterior of the medial dwell point the sagittal concave curvature has a second sagittal conformity with the medial condyle at the first degree of flexion, and wherein the second sagittal conformity is greater than the first sagittal conformity.

In an embodiment, the medial articular surface includes a coronal concave curvature, wherein at the medial dwell point the coronal concave curvature has a first coronal conformity with the medial condyle at the first degree of flexion, wherein at the location on the medial articular surface that is anterior of the medial dwell point the coronal concave curvature has a second coronal conformity with the medial condyle at the first degree of flexion, and wherein the second coronal conformity is greater than the first coronal conformity. In an embodiment, the medial articular surface is non-uniform anterior of the medial dwell point and uniform posterior of the medial dwell point.

In an embodiment, the medial condyle and the medial articular surface are more conforming with each other than the lateral condyle and the lateral articular surface.

In an embodiment, the medial articular surface includes a coronal concave curvature, wherein a coronal conformity between the coronal concave curvature and the medial condyle is greater when the femoral component is positioned at extension than when the femoral component is positioned at a later degree of flexion.

In an embodiment, the lateral articular surface includes an arcuate articular path that when viewed in a cross-section plane has a curvature that includes a semi-planar section, an anterior curved section located anterior of the semi-planar section, and a plurality of posterior curved sections located posterior of the planar section. The planar section defines a distal-most area of the lateral articular surface. In an embodiment, each posterior curved section is defined by a corresponding radius of curvature, wherein the radii of curvature of the plurality of posterior curved sections decrease posteriorly.

In an embodiment, the sagittal concave curvature of the medial articular surface, when viewed in a sagittal plane, includes a plurality of curved sections, wherein the medial dwell point is located on the sagittal concave curvature. The plurality of curved sections includes a first curved section adjacent to the medial dwell point and extending posterior therefrom, a second curved section adjacent the medial dwell point and extending anterior therefrom, a third curved section adjacent to the second curved section and extending anterior therefrom, a fourth curved section adjacent to the third curved section and extending anterior therefrom, and a fifth curved section adjacent the fourth curved section and extending anterior therefrom. A radius of curvature of the first curved section is greater than a radius of curvature of the second curved section and wherein a radius of curvature of the third curved section is less that the radius of curvature of the second curved section, less than a radius of curvature of the fourth curved section, and less than a radius of the fifth radius of curvature In an embodiment, the medial articular surface includes a coronal concave curvature that is defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other.

In an embodiment, the second coronal curvature crosses the sagittal concave curvature of the medial articular surface at an anterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section, and wherein a radius of curvature of the first coronal curved section is less than a radius of curvature of the second coronal curved section.

In an embodiment, the third coronal curvature crosses the sagittal concave curvature of the medial articular surface at an anterior-most point of the fourth curved section of the plurality of curved sections that define the sagittal concave curvature of the medial articular surface, wherein the third coronal curvature is defined by a planar section having a medial end and a lateral end, a first coronal curved section extending from the medial end of the planar section, and a second coronal curved section extending from the lateral end of the planar section.

In an embodiment, the tibial insert further includes a first portion of a locking mechanism located on a bottom surface of the tibial insert, wherein the first portion of the locking mechanism is configured to mate with a second portion of the locking mechanism located on a tibial base to secure the tibial insert to the tibial base.

In an embodiment, a distal-most point of the femoral articular surface when the femoral component is in extension defines zero degrees of flexion, and the first curved femoral surface section extends from a first degree of flexion of about 5 degrees to a second degree of flexion of about 65 degrees. In an embodiment, the first curved femoral surface section is defined by a plurality of rays extending from a common origin to a corresponding point on the second curved femoral surface section. Each ray has a length defined by the following polynomial equation: $r_\theta=(a+(b*\theta)+(c*\theta^2)+(d*\theta^3))$, wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30<b<0.00$, $0.00<b<0.30$, and $b=0$, wherein when b is in the range of $-0.30<b<0.00$, (i) c is a coefficient value between 0.00 and 0.012 and (ii) d is a coefficient value between $-0.00015$ and 0.00, wherein when b is in the range of $0<b<0.30$, (i) c is a coefficient value between $-0.010$ and 0.00 and (ii) d is a coefficient value between $-0.00015$ and 0.00, and wherein when b is equal to 0, (i) c is a coefficient value in a range selected from the group consisting of: $-0.0020<c<0.00$ and $0.00<c<0.0025$ and (ii) d is a coefficient value between $-0.00015$ and 0.00.

In an embodiment, the plurality of curved femoral surface sections includes a second curved femoral surface section posteriorly adjacent the first curved femoral section, wherein the second curved femoral surface section is defined by a constant radius of curvature greater than a posterior-most radii of curvature of the first curved femoral surface section. In an embodiment, the second curved femoral surface section extends from a first degree of flexion of about 65 degrees to a second degree of flexion of about 90.

According to another aspect, an orthopaedic knee prosthesis includes a femoral component having a lateral condyle and a medial condyle and a tibial insert having a lateral articular surface configured to articulate with the lateral condyle of the femoral component and a medial articular surface configured to articulate with the medial condyle of the femoral component. The medial condyle includes a femoral articular surface defined by a plurality of curved femoral surface sections that includes a first curved femoral surface section defined by a continually decreasing radius of curvature. The lateral articular surface includes an arcuate articular path extending in an anterior-posterior direction, wherein the arcuate articular path when viewed in a cross-section plane has a curvature that includes a planar section and wherein the planar section defines a distal-most area of the lateral articular surface. The medial articular surface is asymmetrically shaped relative to the lateral articular surface and includes a medial dwell point that defines a distal-most point of the medial condyle surface, and wherein the medial dwell point is located on the medial condyle surface (i) between a first imaginary medial-lateral bisecting line of the tibial insert that includes an anterior-most end of the planar section of the sagittal curvature of the lateral articular surface and a second imaginary medial-lateral bisecting line of the tibial insert that includes a posterior-most end of the planar section of the sagittal curvature of the lateral articular surface and (ii) posterior to an anterior-posterior midpoint of the planar section of the sagittal curvature of the lateral articular surface.

In an embodiment, the medial condyle of femoral component includes a sagittal convex curvature and the medial articular surface includes a sagittal concave curvature, and wherein a sagittal conformity between the sagittal concave curvature of the medial articular surface and sagittal concave curvature of the medial condyle is greater at a first degree of flexion of the femoral condyle than at extension. In an embodiment, the first degree of flexion is about 30 degrees.

In an embodiment, the medial articular surface includes a sagittal concave curvature, wherein at the medial dwell point the sagittal concave curvature has a first sagittal conformity with the medial condyle at a first degree of flexion of the femoral component, wherein at a location on the medial articular surface that is anterior of the medial dwell point the sagittal concave curvature has a second sagittal conformity with the medial condyle at the first degree of flexion, and wherein the second sagittal conformity is greater than the first sagittal conformity.

In an embodiment, the medial articular surface includes a coronal concave curvature, wherein at the medial dwell point the coronal concave curvature has a first coronal conformity with the medial condyle at the first degree of flexion, wherein at the location on the medial articular surface that is anterior of the medial dwell point the coronal concave curvature has a second coronal conformity with the medial condyle at the first degree of flexion, and wherein the second coronal conformity is greater than the first coronal conformity. In an embodiment, the medial articular surface is non-uniform anterior of the medial dwell point and uniform posterior of the medial dwell point.

In an embodiment, the medial articular surface includes a coronal concave curvature and a coronal conformity between the coronal concave curvature and the medial condyle is greater when the femoral component is positioned at extension than when the femoral component is positioned at a later degree of flexion.

In an embodiment, the arcuate articular path of the lateral articular surface, when viewed in a cross-section plane, has a curvature that includes a semi-planar section, an anterior curved section located anterior of the planar section, and a plurality of posterior curved sections located posterior of the planar section. The semi-planar section defines a distal-most area of the lateral articular surface. In an embodiment, each posterior curved section is defined by a corresponding radius of curvature, and wherein the radii of curvature of the plurality of posterior curved sections decrease posteriorly.

In an embodiment, the sagittal concave curvature of the medial articular surface, when viewed in a sagittal plane, includes a plurality of curved sections and wherein the medial dwell point is located on the sagittal concave curvature. The plurality of curved sections includes a first curved section adjacent to the medial dwell point and extending posterior therefrom, a second curved section adjacent the medial dwell point and extending anterior therefrom, a third curved section adjacent to the second curved section and extending anterior therefrom, a fourth curved section adjacent to the third curved section and extending anterior therefrom, and a fifth curved section adjacent the fourth curved section and extending anterior therefrom. A radius of curvature of the first curved section is greater than a radius of curvature of the second curved section and wherein a radius of curvature of the third curved section is less that the radius of curvature of the second curved section, less than a radius of curvature of the fourth curved section, and less than a radius of the fifth radius of curvature.

In an embodiment, the medial articular surface includes a coronal concave curvature that is defined by a plurality of coronal curvatures including a first coronal curvature that crosses the sagittal concave curvature of the medial articular surface at the medial dwell point, a second coronal curvature located anteriorly to the first coronal curvature, a third coronal curvature located anteriorly to the second coronal curvature, wherein each of the first, second, and third coronal curvatures are different from each other.

In an embodiment, the second coronal curvature crosses the sagittal concave curvature of the medial articular surface at a posterior-most point of the third curved section of the plurality of curved sections that define the sagittal concave curvature of the medial articular surface, wherein the second coronal curvature is defined by a planar section having a medial end and a lateral end, a first coronal curved section extending from the medial end of the planar section, and a second coronal curved section extending from a lateral end of the planar section, and wherein a radius of curvature of the first coronal curved section is less than a radius of curvature of the second coronal curved section.

In an embodiment, the third coronal curvature crosses the sagittal concave curvature of the medial articular surface at an anterior-most point of the fourth curved section of the plurality of curved sections that define the sagittal concave curvature of the medial articular surface, wherein the third coronal curvature is defined by a planar section having a medial end and a lateral end, a first coronal curved section extending from the medial end of the planar section, and a second coronal curved section extending from the lateral end of the planar section.

In an embodiment, the tibial insert further includes a first portion of a locking mechanism located on a bottom surface of the tibial insert, wherein the first portion of the locking mechanism is configured to mate with a second portion of the locking mechanism located on a tibial base to secure the tibial insert to the tibial base.

In an embodiment, a distal-most point of the femoral articular surface when the femoral component is in extension defines zero degrees of flexion. The first curved femoral surface section extends from a first degree of flexion of about 5 degrees to a second degree of flexion of about 65 degrees. In an embodiment, the first curved femoral surface section is defined by a plurality of rays extending from a common origin to a corresponding point on the second curved femoral surface section. Each ray has a length defined by the following polynomial equation: $r_\theta=(a+(b*\theta)+(c*\theta^2)+(d*\theta^3))$, wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30<b<0.00$, $0.00<b<0.30$, and $b=0$, wherein when b is in the range of $-0.30<b<0.00$, (i) c is a coefficient value between 0.00 and 0.012 and (ii) d is a coefficient value between $-0.00015$ and 0.00, wherein when b is in the range of $0<b<0.30$, (i) c is a coefficient value between $-0.010$ and 0.00 and (ii) d is a coefficient value between $-0.00015$ and 0.00, and wherein when b is equal to 0, (i) c is a coefficient value in a range selected from the group consisting of: $-0.0020<c<0.00$ and $0.00<c<0.0025$ and (ii) d is a coefficient value between $-0.00015$ and 0.00.

In an embodiment, the plurality of curved femoral surface sections includes a second curved femoral surface section posteriorly adjacent the first curved femoral surface section, wherein the second curved femoral surface section is defined by a constant radius of curvature greater than a posterior-most radii of curvature of the first curved femoral surface section.

In an embodiment, the second curved femoral surface section extends from a first degree of flexion of about 65 degrees to a second degree of flexion of about 90.

BRIEF DESCRIPTION OF THE DRAWINGS

The detailed description particularly refers to the following figures, in which:

FIG. 7 is a table of an embodiment of coefficient values of a polynomial equation that may define a curved surface section of one or more condyle surfaces of the femoral component of FIG. 4;

DETAILED DESCRIPTION OF THE DRAWINGS

Figure 1:
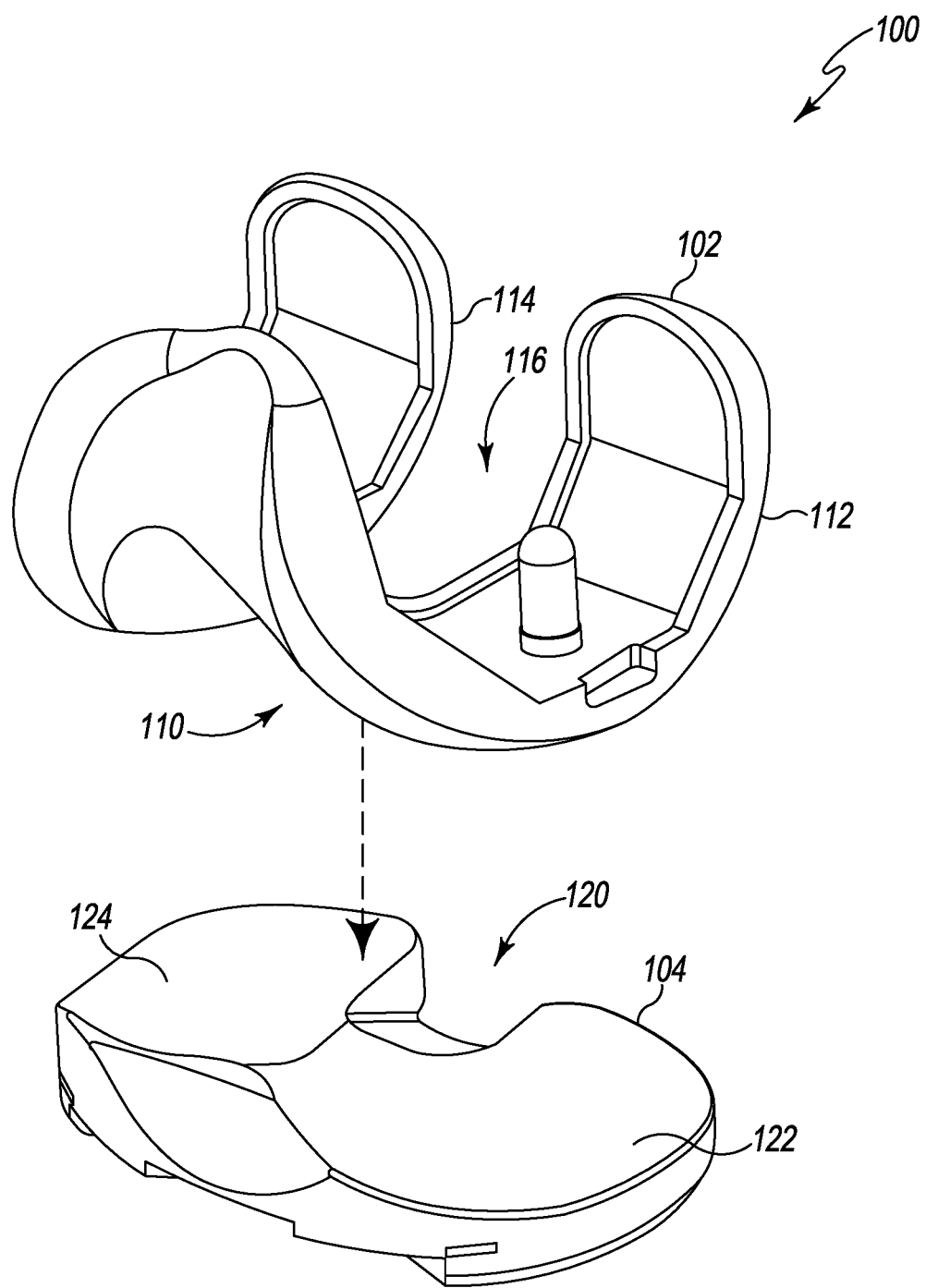
FIG. 1 is an exploded perspective view of an embodiment of an orthopaedic knee prosthesis.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and/or surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. Additionally, the term "about" may be used in the specification in reference to certain measurements that are defined within manufacturing tolerances. That is, the provided measurements and/or numerical values may deviate, in practice, due to tolerances inherent in the machine or fabrication process.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 2:
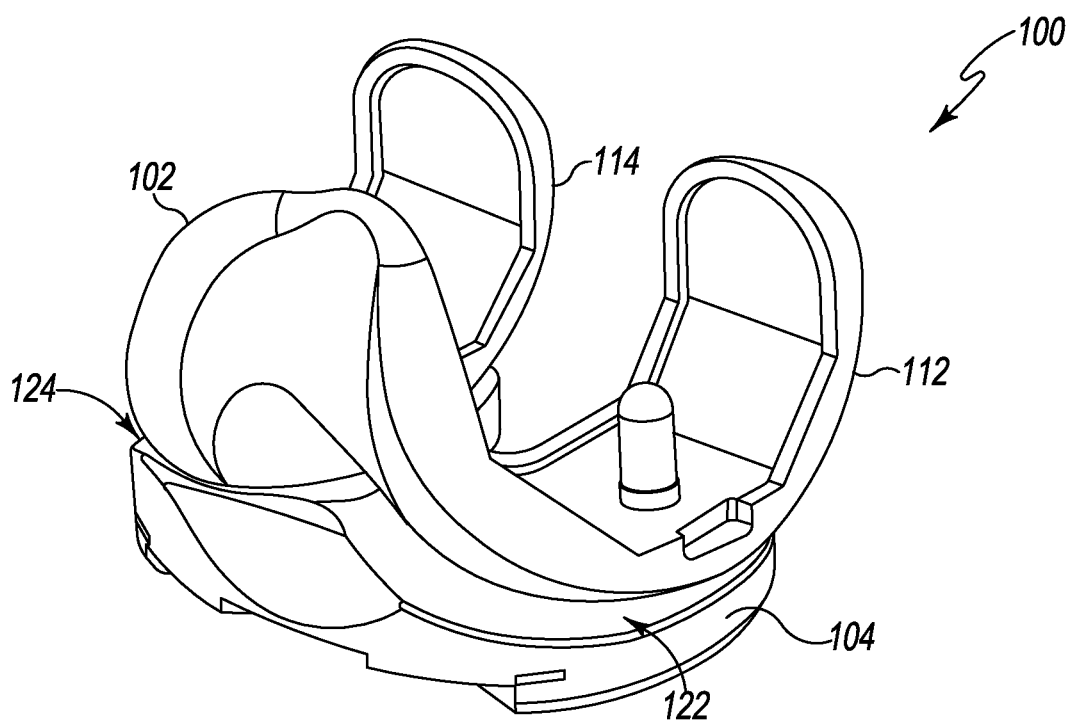
FIG. 2 is lateral perspective view of the orthopaedic knee prosthesis of FIG. 1 in an assembled configuration.
Figure 3:
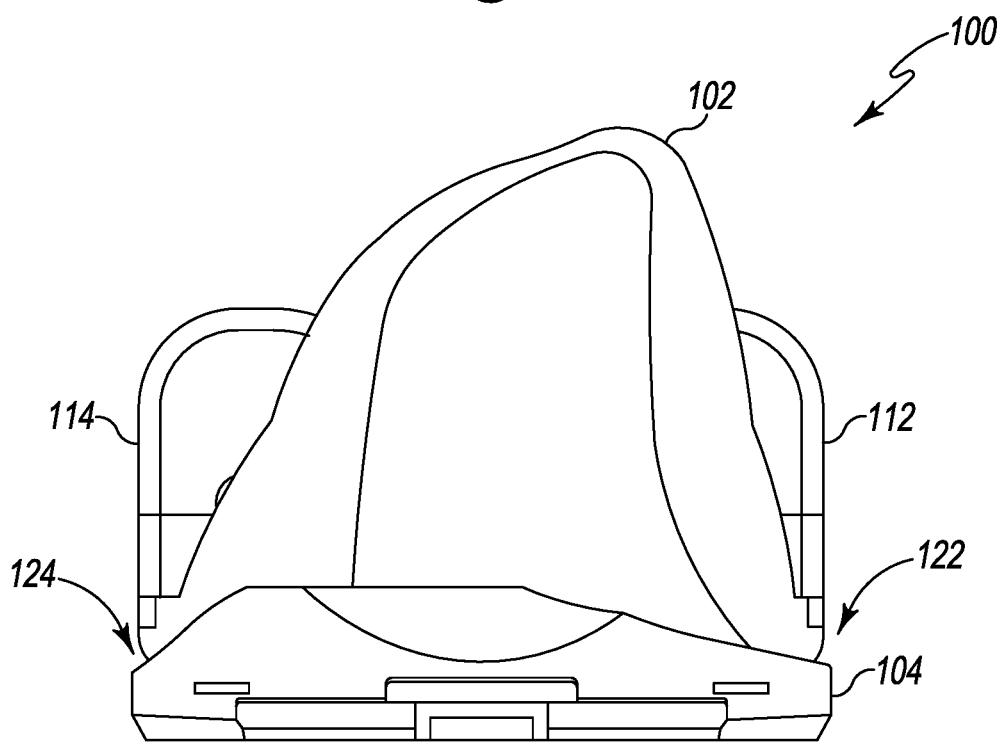
FIG. 3 is an anterior elevation view of the orthopaedic knee prosthesis of FIG. 1.

Referring now to FIGS. 1-3, in an illustrative embodiment, an orthopaedic knee prosthesis 100 includes a femoral component 102 and a tibial insert 104. Additionally, the orthopaedic knee prosthesis 100 may include a tibial tray (not shown) to which the tibial insert 104 is coupled during use. The femoral component 102 (and the tibial tray) are illustratively formed from a metallic material such as cobalt-chromium or titanium, but may be formed from other materials, such as a ceramic material, a polymer material, a bio-engineered material, or the like, in other embodiments. The tibial insert 104 is illustratively formed from a polymer material such as an ultra-high molecular weight polyethylene (UHMWPE), but may be formed from other materials, such as a ceramic material, a metallic material, a bio-engineered material, or the like, in other embodiments.

The femoral component 102 is configured to be coupled to a surgically-prepared surface of the distal end of a patient's femur (not shown), and the tibial insert 104 is configured to be coupled to a surgically-prepared surface of the proximal end of a patient's tibia (not shown) via, for example, a tibial tray (not shown). Alternatively, in other embodiments, the tibial insert 104 may be configured to attach to the surgically-prepared surface of the proximal end of the patient's tibia directly, without use of a tibial tray. For example, the tibial insert 104 and a polymer "tray" may be combined into a single polymeric component.

In use, the femoral component 102 is configured to articulate with the tibial insert 104. To do so, the femoral component includes an outer, articulating surface 110 having a lateral condyle 112 and a medial condyle 114. Similarly, the tibial insert 104 includes an articular surface 120 having lateral articular surface 122 and a medial articular surface 124. As such, the lateral condyle 112 is configured to articulate with the lateral articular surface 122, and the medial condyle 114 is configured to articulate with a medial articular surface 124 of the tibial insert as shown in FIGS. 28-31.

As discussed in more detail below, each of the femoral component 102 and the tibial insert 104 include articular curvatures and related features that facilitate or promote pivoting of the lateral condyle 112 on the lateral articular surface 122, while limiting or reducing anterior translation of the medial condyle 114 on the medial articular surface 124 during flexion. For example, one or both of the condyles 112, 114 include a sagittal condylar surface having a curved surface section defined by a continuously decreasing radius of curvature. Additionally, the medial articular surface 124 has a concave sagittal curvature that is overall more conforming with a convex sagittal curvature of the medial condyle 114 at a degree of mid-flexion (e.g., 30 degrees) than at extension. The lateral and medial articular surfaces 122, 124 of the tibial insert 104 are also asymmetrically shaped to provide asymmetric pivoting of the femoral component 102 on the tibial insert 104. Additionally, the lateral articular surface 122 and the lateral condyle 112 may be less conforming with each other than the medial articular surface 124 and the medial condyle 114. Furthermore, as discussed below, the coronal curvature of the lateral articular surface 122 is uniform in the anterior-posterior direction, while the coronal curvature of the medial articular surface 124 is non-uniform in the anterior-posterior direction (e.g., the coronal curvature of the medial articular surface 124 is defined by multiple, different coronal curvatures). Additionally, the medial articular surface 124 may be more conforming with the medial condyle 114 in extension, compared to flexion and more conforming anterior of a dwell point of the medial condyle 114 (see discussion of FIGS. 18-27 below) than at the dwell point, due to the sagittal shape of the medial articular surface 124. It should be appreciated that the sagittal curvature of the femoral condyles 112, 114, the overall sagittal conformity between the medial condyle 114 and the medial articular surface 124, the asymmetry of the lateral and medial articular surfaces 122, 124, the increased conformity in extension and anterior of the dwell point of the medial condyle 114 improves the stability of the orthopaedic knee prosthesis 100, facilitates pivoting of the lateral femoral condyle 112, and reduces or restricts medial anterior translation of the femur.

As discussed above, the femoral component 102 is configured to be coupled to a surgically-prepared surface of the distal end of a patient's femur (not shown) and may be secured to the patient's femur via use of bone adhesive or other attachment means. The femoral component 102 includes the lateral condyle 112 and the medial condyle 114, which are spaced apart to define an intercondylar opening 116 therebetween. In use, the condyles 112, 114 replace the natural condyles of the patient's femur and are configured to articulate on the corresponding lateral and medial articular surfaces 122, 124 of the tibial insert 104 as discussed above.

Figure 4:
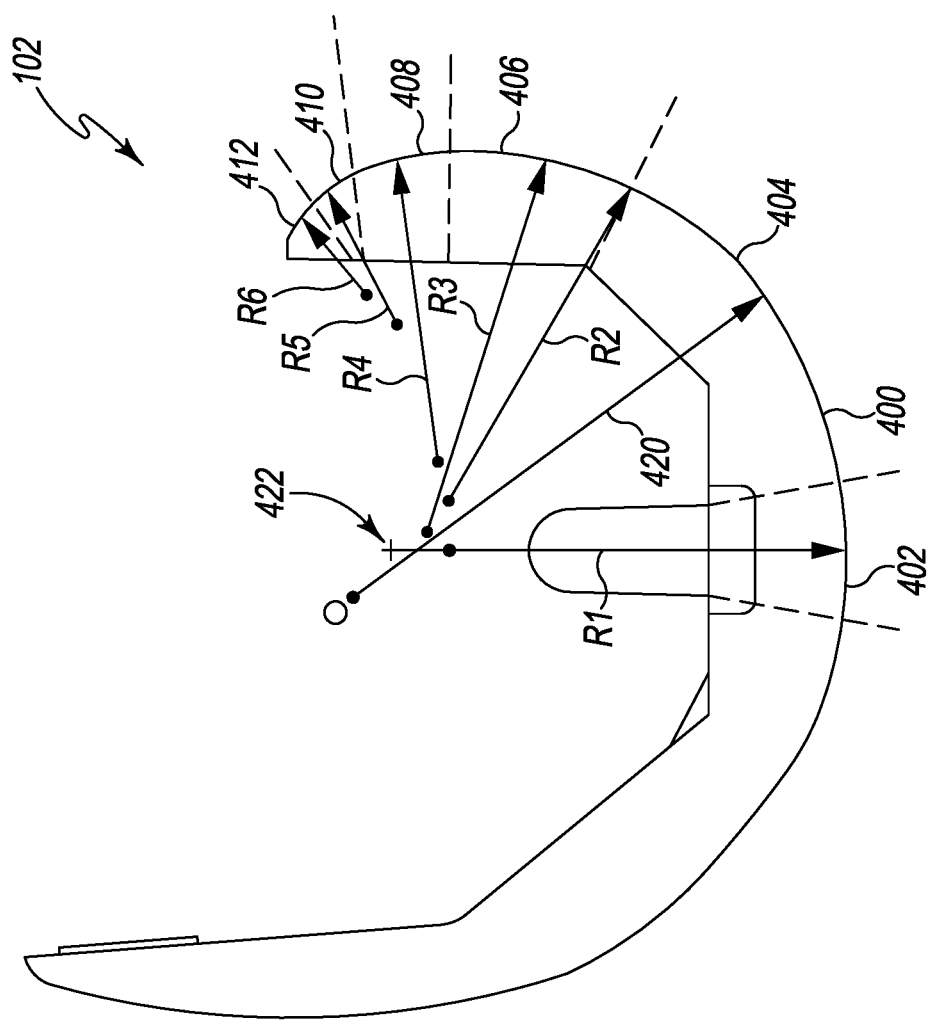
FIG. 4 is a side elevation view of an embodiment of a femoral component of the orthopaedic knee prosthesis of FIG. 1.

Referring now to FIG. 4, one or both of the condyles 112, 114 of the femoral component 102 include a condyle surface 400, which is convexly curved in the sagittal plane. Illustratively, the condyle surface 400 is formed from a number of curved surface sections 402, 404, 406, 408, 410, and 412 each of which is tangent to the adjacent curved surface section. Each curved surface sections 402, 404, 406, 408, 410, and 412 contacts the tibial bearing insert through different ranges of degrees of flexion. For example, the curved surface sections 402, 404 of the condyle surface 400 contact the tibial insert 104 during early flexion. The curved surface sections 406, 408 of the condyle surface 400 contact the tibial insert 104 during mid-flexion. And, the curved surface sections 410, 412 of the condyle surface 400 contact the tibial insert 104 during late flexion.

Each curved surface sections 402, 406, 408, 410, and 412 is defined by a constant radius of curvature R1, R3, R4, R5, and R6, respectively. However, as discussed in more detail below, the curved surface section 404 is defined by a plurality of rays, rather than a constant radius of curvature. In particular, the curved surface section 3604 is designed to transition gradually the condyle surface 400 from the radius of curvature R1 of the curved surface section 402 to a radius of curvature R2, which is tangent to the curved surface section 406. As such, the curved surface section 3604 has a continuously decreasing radius of curvature.

Figure 5:
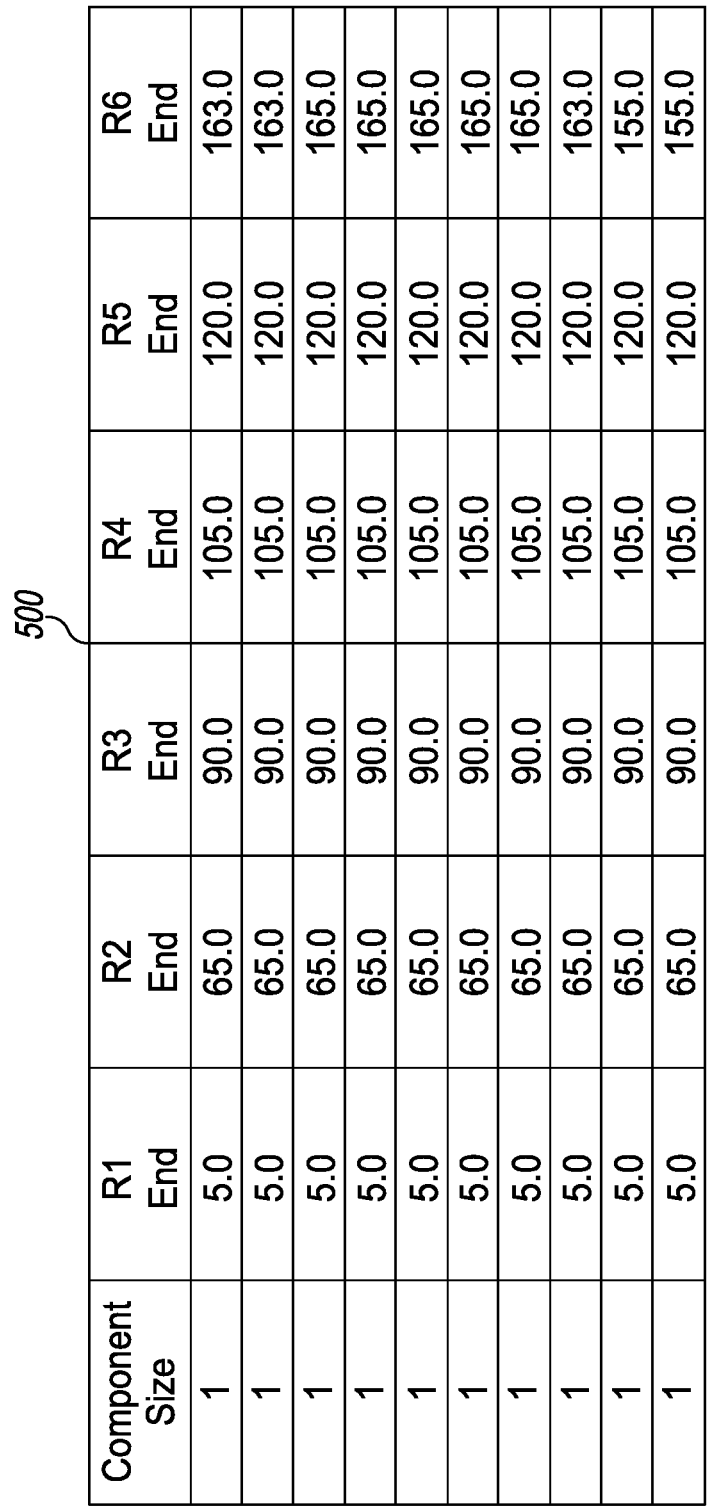
FIG. 5 is a table of an embodiment of ending degrees of flexion for radii of curvature for a family of femoral component sizes of the femoral component of FIG. 4.

In the illustrative embodiment as shown in table 500 of FIG. 5, the curved surface section 402 defined by the radius of curvature R1 ranges from a first degree of flexion of −5 degrees to a second degree of flexion of 5 degrees. The curved section 404 defined by the radius of curvature R2 ranges from a first degree of flexion of 5 degrees to a second degree of flexion of 65 degrees. The curved section 406 defined by the radius of curvature R3 ranges from a first degree of flexion of 65 degrees to a second degree of flexion of 90 degrees. The curved section 408 defined by the radius of curvature R4 ranges from a first degree of flexion of 90 degrees to a second degree of flexion of 105 degrees. The curved section 410 defined by the radius of curvature R5 ranges from a first degree of flexion of 105 degrees to a second degree of flexion of 120 degrees. And, the curved section 412 defined by the radius of curvature R6 ranges from a first degree of flexion of 120 degrees to a second degree of flexion of 163 degrees (or 155 degrees depending on the size). In other embodiments, any of the curved surface sections 402, 406, 408, 410, and 412 have range across a different number of degrees.

Figure 6:
FIG. 6 is a table of an embodiment of radii of curvature length values and corresponding ratios for a family of femoral component sizes of the femoral component of FIG. 4.
Figure 8:
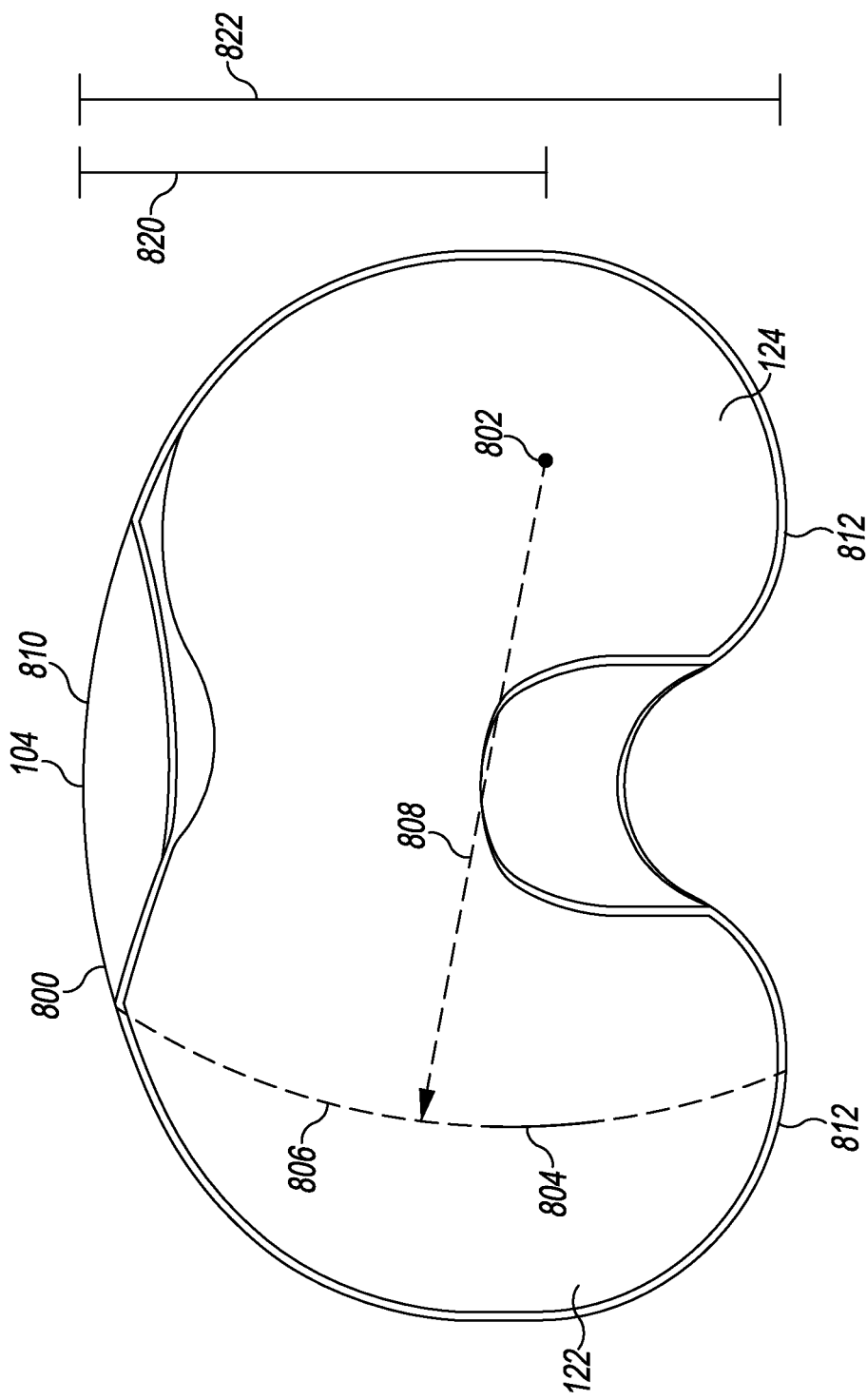
FIG. 8 is a superior plan view of a tibial insert of the orthopaedic knee prosthesis of FIG. 1 illustrating a lateral arcuate articular path.

As shown in FIG. 6, a table 600 defines the length of each radius of curvature R1, R2, R3, R4, R5, and R6, for a family of femoral component sizes 1 through 10. As illustrated in the table 600, while the particular length of each radius of curvature R1, R2, R3, R4, R5, R6 for each size 1-10 of the femoral component 102 may vary across sizes, the ratios of R1/R2, R1/R3, and R1/R4 are relatively constant, or vary slightly, across the femoral component sizes. For example, the ratio of the radius of curvature R1 to the radius of curvature R2 may vary in a range of about 1.347 to 1.355, to maintain a value of about 1.350 across the femoral component sizes 1 through 10. Similarly, the ratio of the radius of curvature R1 to the radius of curvature R3 may vary in a range of about 1.277 to 1.278, to maintain a value of about 1.280 across the femoral component sizes 1 through 10. Furthermore, the ratio of the radius of curvature R1 to the radius of curvature R4 may be maintained at a value of about 1.305 across the femoral component sizes 1 through 10.

It should also be appreciated that the condyle surface 400 of the femoral component 102 is designed such that the radius of curvature R3 is greater than the radius of curvature R2 by an amount in the range of about 0.5 millimeters to about 5 millimeters in some embodiments. As discussed below, the particular amount of increase may be based on the size of the femoral component in some embodiments. Additionally, based on the above analysis, the condyle surface 400 is designed such that the increase in the radius of curvature from R2 to R3 occurs at a degree of flexion in the range of about 45 degrees to about 90 degrees. In one particular embodiment, the increase in radius of curvature from R2 to R3 occurs at about 65 degrees of flexion on the condyle surface 400.

As discussed above, the curved surface section 404 is designed to provide a gradual transition from the radius of curvature R1 to the radius of curvature R2. As such, the size of the angle defined by the curved surface section 404 may be selected based on the desired rate of transition. For example, in some embodiments, the condyle surface 400 of the femoral component 102 is designed such that the curved surface section 404 extends from a first degree of flexion in the range of about 0.0 to about 30.0 degrees to a second degree of flexion in the range of about 45.0 to about 90.0 degrees of flexion. In one particular embodiment, the curved surface section 404 extends from about 5.0 degrees of flexion to about 65.0 degrees of flexion, as discussed above.

It should be appreciated that the particular amount of increase in the radius of curvature R2 to R3 of the condyle surface 400 of the femoral component 102 and/or the positioning of such increase on the condyle surface 400 may also be based on, scaled, or otherwise affected by the size of the femoral component 102. That is, it should be appreciated that an increase of the radius of curvature R2 to R3 of the condyle surface 400 of 0.5 millimeters is a relatively larger increase in small-sized femoral components compared to larger-sized femoral components. As such, the magnitude of the increase in the radius of curvature R2 to R3 of the condyle surface 400 of the femoral component 102 may change across femoral component sizes. In some embodiments, however, the ratios of the radius of curvatures R1 to the radius of curvatures R2, R3, and R4 are maintained at a substantially constant value across the family of femoral component sizes.

As discussed above, the curved surface section 404 is designed to provide a gradual transition from the radius of curvature R1 to the radius of curvature R2. To do so, the curved surface section 404 is defined by a plurality of rays 420, which originate from a common origin O. Each of the plurality of rays 420 defines a respective contact point on the curved surface section 404. The location of each of those contact points, which collectively define the curved surface section 404, can be determined based on the length of each ray 420 at each degree of flexion according to the following polynomial equation:

$$r_\theta = (a + (b*\theta) + (c*\theta^2) + (d*\theta^3)), \quad (3)$$

wherein "$r_\theta$" is the length of a ray 420 (in metric units) defining a contact point on the curved surface section 404 at "$\theta$" degrees of flexion, "a" is a scalar value between 20 and 50, and "b" is a coefficient value selected such that:

$$-0.30 < b < 0.00,$$

$$0.00 < b < 0.30, \text{ or}$$

$$b = 0 \quad (4)$$

If the selected coefficient "b" is in the range of $-0.30 < b < 0.00$, then coefficients "c" and "d" are selected such that:

$$0.00 < c < 0.012, \text{ and}$$

$$-0.00015 < d < 0.00. \quad (5)$$

Alternatively, if the selected coefficient "b" is in the range of $0.00 < b < 0.30$, then coefficients "c" and "d" are selected such that:

$$-0.010 < c < 0.00, \text{ and}$$

$$-0.00015 < d < 0.00. \quad (6)$$

Further, if the selected coefficient "b" is equal to 0, then coefficients "c" and "d" are selected such that:

$$-0.0020 < c < 0.00, \text{ or}$$

$$0.00 < c < 0.0025, \text{ and}$$

$$-0.00015 < d < 0.00. \quad (7)$$

It should be appreciated that ranges of values for the scalar "a" and coefficients "b", "c", and "d" are a subset of an infinite number of possible solutions for the polynomial equation (3). That is, the particular set of ranges provided above have been determined from an infinite number of possibilities to generate a family of curves (i.e., the curved surface section 404) that provide a gradual transitioning of the condyle surface 400 from the radius of curvature R1 to the radius of curvature R2 such that anterior translation of the femoral component 102 relative to the tibial insert 104 (e.g., anterior translation of the medial side) is reduced or delayed. Additionally, it should be appreciated that the range of values for each coefficient "a", 'b", "c", and "d" are provided above in regard to embodiments designed using the metric system of units. However, such range of coefficient values may be converted for use in embodiments using other systems of units such as the English system of units.

The overall shape of the curved surface section 404 is also affected by the placement of the common origin O of the plurality of rays 420. By limiting the distance between the common origin O of the plurality of rays 420 and the origin 422 of the radius of curvature R1, which defines the early flexion curved surface section 402, paradoxical anterior sliding of the femoral component 102 on the tibial insert 104 may be reduced or delayed. As such, in one embodiment, the location of the common origin O of the plurality of rays 420 is selected such that the distance between the common origin O and the origin 422 of the radius of curvature R1 is less than about 10 millimeters. It should be appreciated that the distance between the common origin O and the origin 422 of the radius of curvature R1 and the particular coefficient values may be dependent upon the particular size of the femoral component 102 in some embodiments. An illustrative embodiment of distances between the common origin O and the origin 422 of the radius of curvature R1 and the particular coefficient values for equation (3) are shown in table 700 of FIG. 7.

In other embodiments, the curved surface section 404 may be designed to provide a gradual transition from the radius of curvature R1 to the radius of curvature R2 using other geometry. For example, the radii forming the curved surface section 404 may not have common origin but may be of the same length. In such embodiment, the origin of each radii is moved along a spiral to provide a gradual transition from the radius of curvature R1 to the radius of curvature R2. Additionally, in yet other embodiments, the curved surface section 404 may be formed from a plurality of small curved sections each having a small arc length (e.g., 1 degree) and each defined by a constant radius that decreases relative to the anterior-most adjacent small curved section.

Referring now to FIGS. 8-18, the illustrative tibial insert 104 includes a body 800, which includes the asymmetrical lateral and medial articular surfaces 122, 124. The medial articular surface 124 includes a dwell point 802, which defines a distal most point of the medial articular surface 124 and, generally, the contact point or region at which the medial condyle 114 of the femoral component 102 contacts the medial articular surface 124 during articulation (although some contact between the femoral component 102 and the tibial insert 104 may occur anterior to the medial dwell point 802 at some degrees flexion and depending on loading of the femoral component 102 and tibial insert 104.

Illustratively, the dwell point 802 is located on the medial articular surface 124 in relation to an anterior sidewall 810 of the body 800 of the tibial insert 104. For example, in the illustrative embodiment, the dwell point 802 is located on the medial articular surface 124 a distance 820 that is about 63.3% of the overall medial anterior-posterior length 822, which is defined as the distance from an anterior-most point on the anterior sidewall 810 to a posterior-most point on a posterior sidewall 812 of the body 800 of the tibial insert 104 on the medial side (i.e., measured across the medial articular surface 124). It should be appreciated that in some embodiments, the lateral articular surface 122 and the medial articular surface 124 may have different anterior-posterior lengths due to different posterior-most points on the posterior sidewall 812.

Unlike the dwell point 802 of the medial articular surface 124, the lateral articular surface 122 includes a dwell region 804 (shown as a solid line in FIG. 8), which defines a distal-most region of the lateral articular surface 122. The dwell region 804 is embodied as a region of contact because the dwell region 804 corresponds to a semi-planar or semi-flat section of the "sagittal" curvature of the lateral articular surface 122. As used herein, the term "semi-planar" refers to a section that is either planar or is otherwise defined by a radius that is at least three times the length of the radius of curvature of the adjacent curved section as discussed in more detail below. That is, the dwell region 804 may be embodied as a surface section that is defined by a large enough radius of curvature that the curvature of the dwell region 804 approximates a planar section when viewed in a cross-section taken along the arcuate articular path 806.

The dwell region 804 lies on an arcuate articular path 806 of the lateral articular surface 122, which defines a path of contact points between the lateral condyle 112 of the femoral component 102 and the lateral articular surface 122 through flexion of the femoral component 102 (although the lateral condyle 112 may not travel the complete arcuate articular path 806 during normal flexion). The arcuate path 806 is defined by a radius of curvature 808, which has an origin congruent with the dwell point 802 of the medial articular surface 124 or within a reference distance thereof. In the illustrative embodiment, the length of the radius of curvature 808 is design to match, within manufacturing tolerances, the pitch of the condyles 112, 114 of the femoral component 102 (i.e., the distance between the distal-most points on each condyle 112, 114). As such, the curvature of the lateral articular surface 122 is designed to allow the femoral component 102 to pivot or rotate, relative to the dwell point 802, along the arcuate articular path 806 during flexion of the femoral component 102. That is, as the femoral component 102 is moved from extension through flexion, the contact point between the lateral condyle 112 of the femoral component 102 and the lateral articular surface 122 moves posteriorly along the arcuate path 806.

Similar to the dwell point 802, the dwell point 804 is illustratively located on the lateral articular surface 122 in relation to the anterior sidewall 810 of the body 800 of the tibial insert 104. For example, in the illustrative embodiment, the dwell point 804 is located on the lateral articular surface 122 a distance 920 that is about 62.6% of the overall lateral anterior-posterior length 922, which is defined as the distance from an anterior-most point on the anterior sidewall 810 to a posterior-most point on a posterior sidewall 812 of the body 800 of the tibial insert 104 on the lateral side (i.e., measured across the lateral articular surface 122). Again, it should be appreciated that in some embodiments, the lateral articular surface 122 and the medial articular surface 124 may have different anterior-posterior lengths due to different posterior-most points on the posterior sidewall 812.

Figure 9:
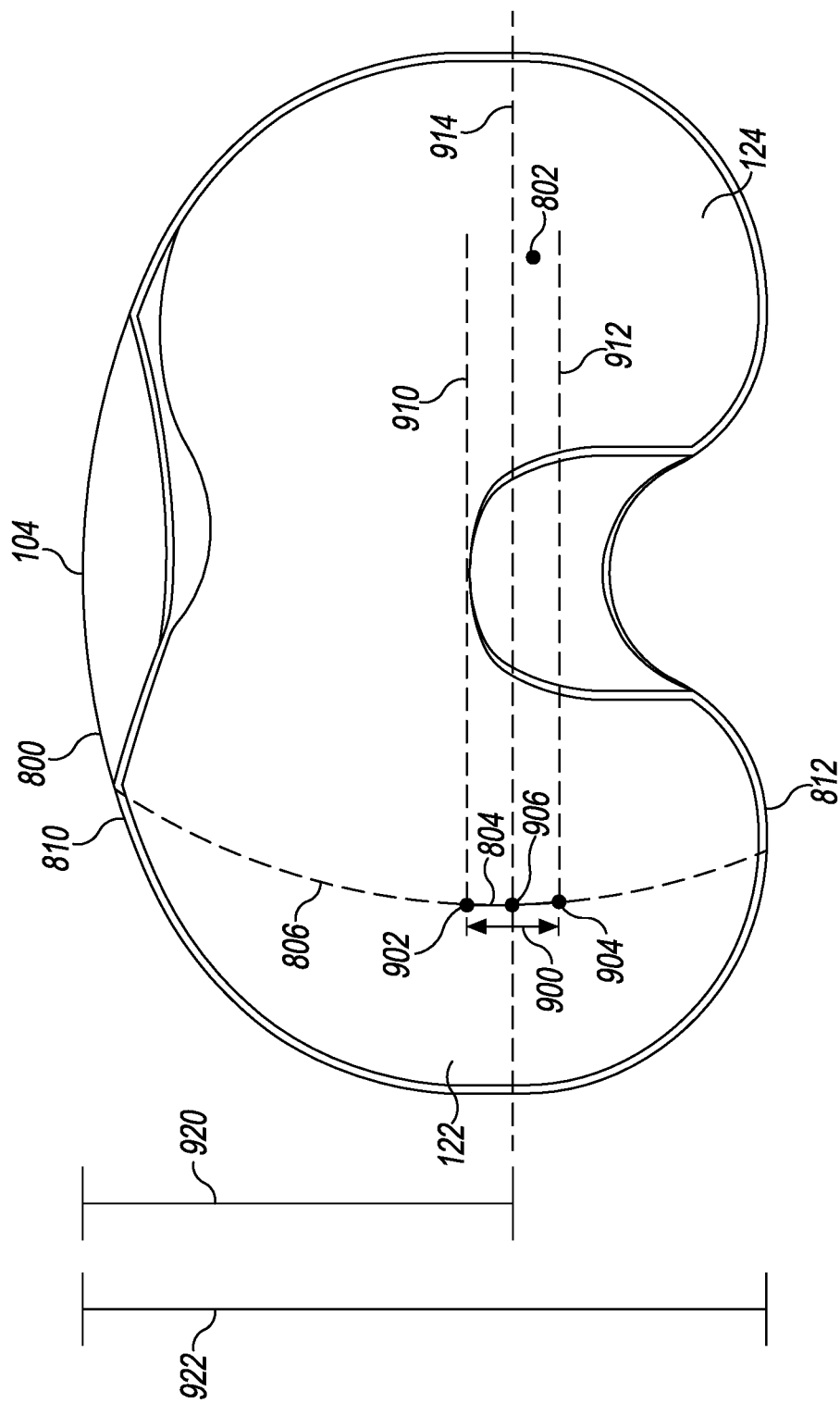
FIG. 9 is another superior plan view of the tibial insert of FIG. 8 illustrating a lateral dwell region.

Additionally, as shown in FIG. 9, the dwell point 802 of the medial articular surface 124 is spatially related to the dwell region 804 of the lateral articular surface 122. Specifically, the dwell region 804 has a length 900 defined as the distance between an anterior-most end 902 of the dwell region 804 (shown as a solid point on FIG. 9) and a posterior-most end 904 of the dwell region 804 (also shown as a solid point on FIG. 9), and the dwell point 802 is located on the medial articular surface 124 between the anterior-most end 902 and the posterior-most end 904 of the dwell region 804. That is the dwell point 804 is located on the medial articular surface 124 between an anterior, imaginary medial-lateral bisecting line 910 that includes the anterior-most end 902 of the dwell region 804 and a posterior, imaginary medial-lateral bisecting line 912 that includes the posterior-most end 904 of the dwell region 804. Additionally, as shown in FIG. 9, the dwell point 804 is located on the medial articular surface 124 posterior to a midpoint 906 of the dwell region 804 (shown as a solid point on FIG. 9). That is the dwell point 804 is located on the medial articular surface 124 posterior to an imaginary medial-lateral bisecting line 914 that includes the midpoint 906 of the dwell region 804.

Figure 10:
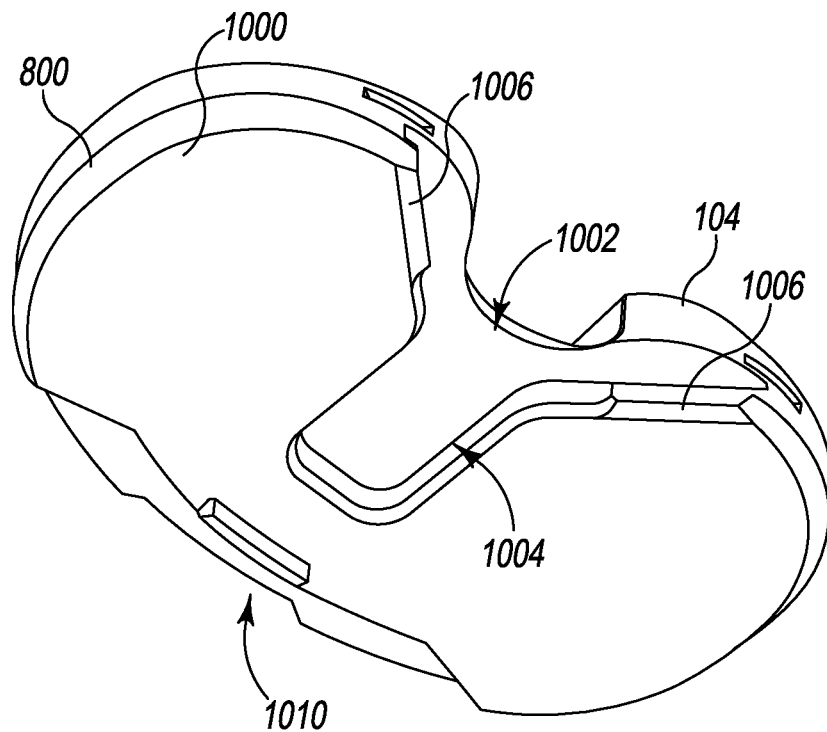
FIG. 10 is an inferior perspective view of the tibial insert of FIG. 8.
Figure 11:
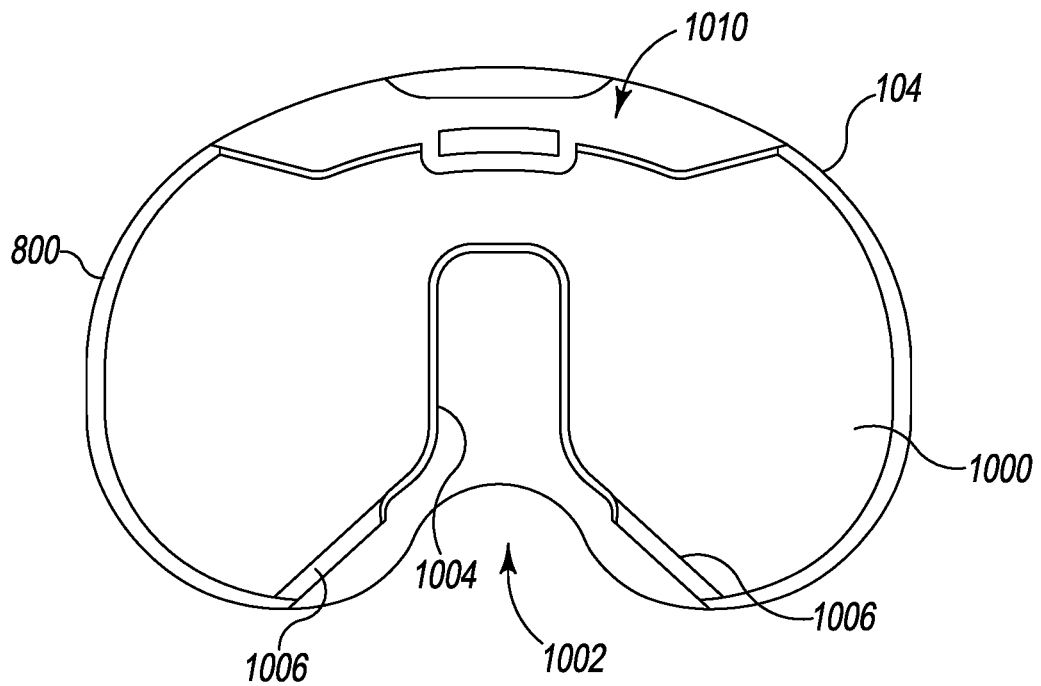
FIG. 11 is an inferior plan view of the tibial insert of FIG. 8.
Figure 12:
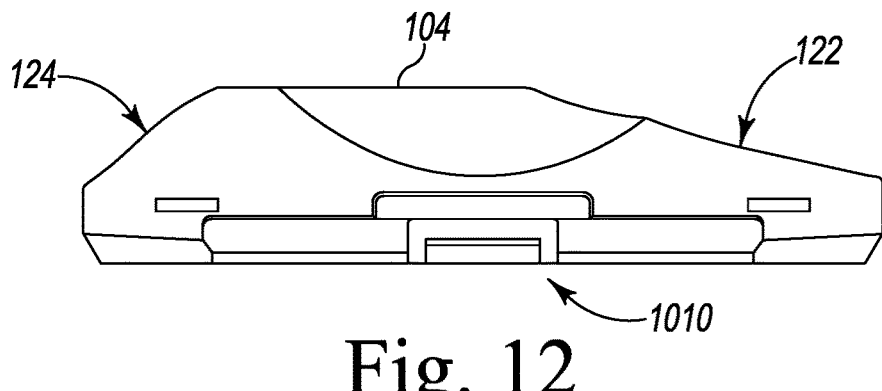
FIG. 12 is an anterior elevation view of the tibial insert of FIG. 8.
Figure 13:
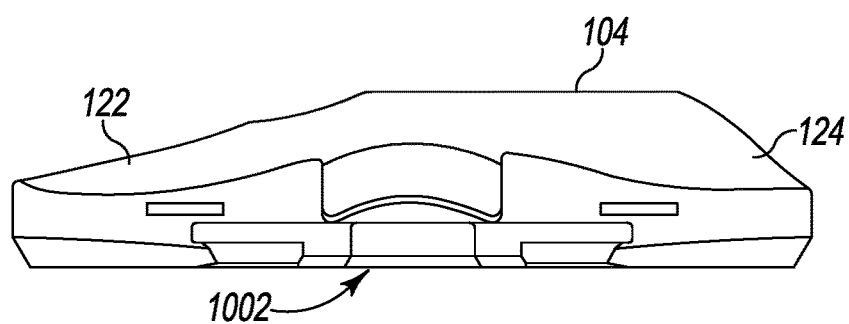
FIG. 13 is a posterior elevation view of the tibial insert of FIG. 8.
Figure 14:
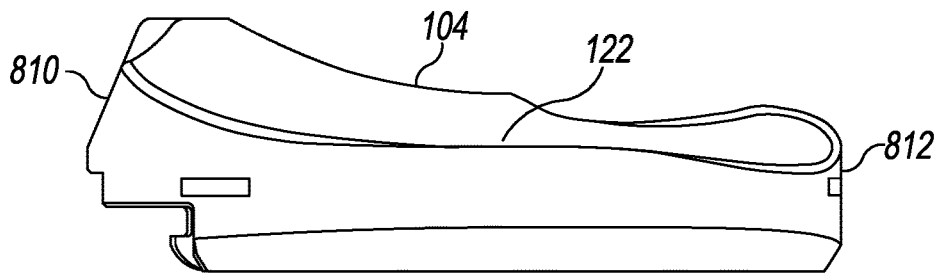
FIG. 14 is a lateral elevation view of the tibial insert of FIG. 8.
Figure 15:
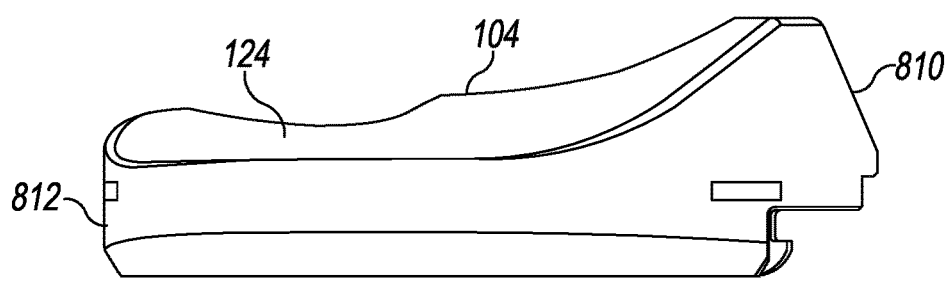
FIG. 15 is a medial elevation view of the tibial insert of FIG. 8.

As shown in FIGS. 10 and 11, the body 800 of the tibial insert 104 includes a bottom side 1000, which is configured to confront a platform of a tibial tray (not shown) during implantation as discussed above. The illustrative tibial insert 104 includes a posterior channel 1002 sized and shaped to receive a posterior buttress of the tibial tray. The posterior channel 1002 is defined by sidewalls 1004, which includes flanges 1006 that extend inwardly into the posterior channel 1002 and are positioned to be received in undercuts of the corresponding tibial tray. The tibial insert 104 also includes an anterior channel 1010 that is sized and shaped to receive an anterior buttress of the corresponding tibial tray. In this way, the channels 1002, 1010 cooperate with features of the corresponding tibial tray to lock the tibial insert 104 onto the tibial tray in a single orientation relative to the tibial tray. It should be appreciated that in other embodiments the tibial insert 104 and a corresponding tibial tray may include a non-mobile bearing interface that allows the tibial insert 104 to move independent of the corresponding tibial tray. Additionally, as discussed above, the tibial insert 104 may be configured to attach directly to the patient's tibia in some embodiments. In such embodiments, the tibial insert 104 may not include the features described above for coupling to a tibial tray and may include other geometry that allows for implantation of the tibial insert 104 directly onto the patient's bony anatomy.

Figure 16:
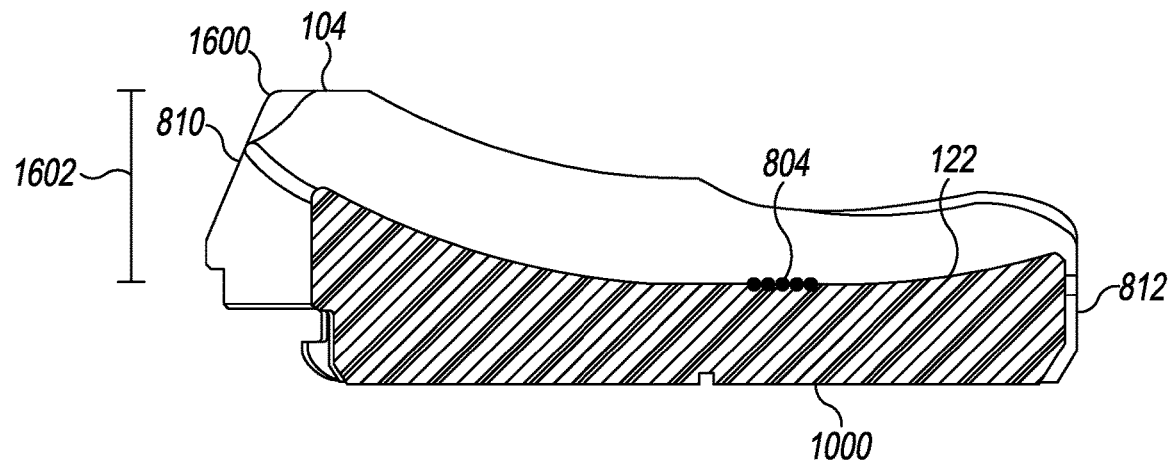
FIG. 16 is a cross-sectional view of a lateral articulation surface of the tibial insert of FIG. 8 in a illustrating a lateral dwell region.
Figure 17:
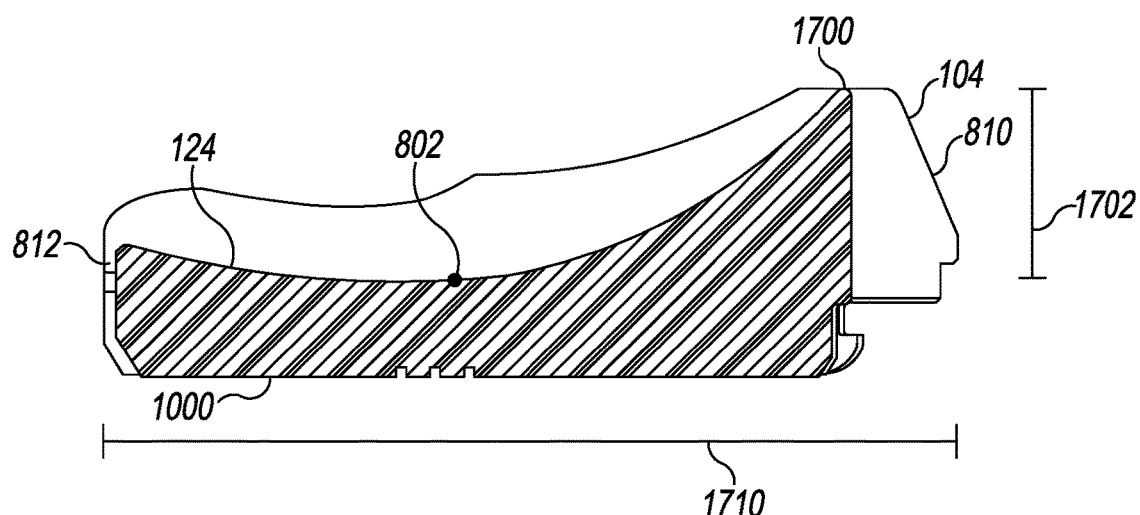
FIG. 17 is a cross-sectional view of a medial articulation surface of the tibial insert of FIG. 8 in a sagittal plane illustrating a medial dwell point.

As discussed above, the medial articular surface 124 and the lateral articular surface 122 are asymmetric to each other. For example, as best shown in FIGS. 12-17, the medial articular surface 124 has an anterior lip that is higher than an anterior lip of the lateral articular surface 122. For example, as shown in FIG. 16, the lateral articular surface 122 includes a lateral anterior lip 1600, which defines the lip or rim of the anterior sidewall 810 on the lateral side. The lateral anterior lip 1600 has a lip height 1602 defined by a vertical distance (i.e., an inferior-superior distance) between the lateral dwell point/region 804 of the tibial insert 104 and the lateral anterior lip 1600. Similarly, as shown in FIG. 17, the medial articular surface 124 includes a medial anterior lip 1700, which defines the lip or rim of the anterior sidewall 810 on the medial side. The medial anterior lip 1700 has a lip height 1702 defined by a vertical distance (i.e., an inferior-superior distance) between the medial dwell point 802 of the tibial insert 104 and the medial anterior lip 1700. In the illustrative embodiment, the lip height 1702 of the medial anterior lip 1700 is greater than the lip height 1602 of the lateral anterior lip 1600.

Additionally, the dwell point 802 of the medial articular surface 124 is positioned such that a ratio between the distance 1710 of the medial dwell point 802 and the anterior sidewall 810 to the lip height 1702 is relatively constant across sizes of the tibial insert 104. For example, in one illustrative embodiment, the ratio between the lip height 1702 to the dwell point distance 1710 is in the range of 18.9% to 20.9%, depending on the size of the tibial insert 104.

Figure 18:
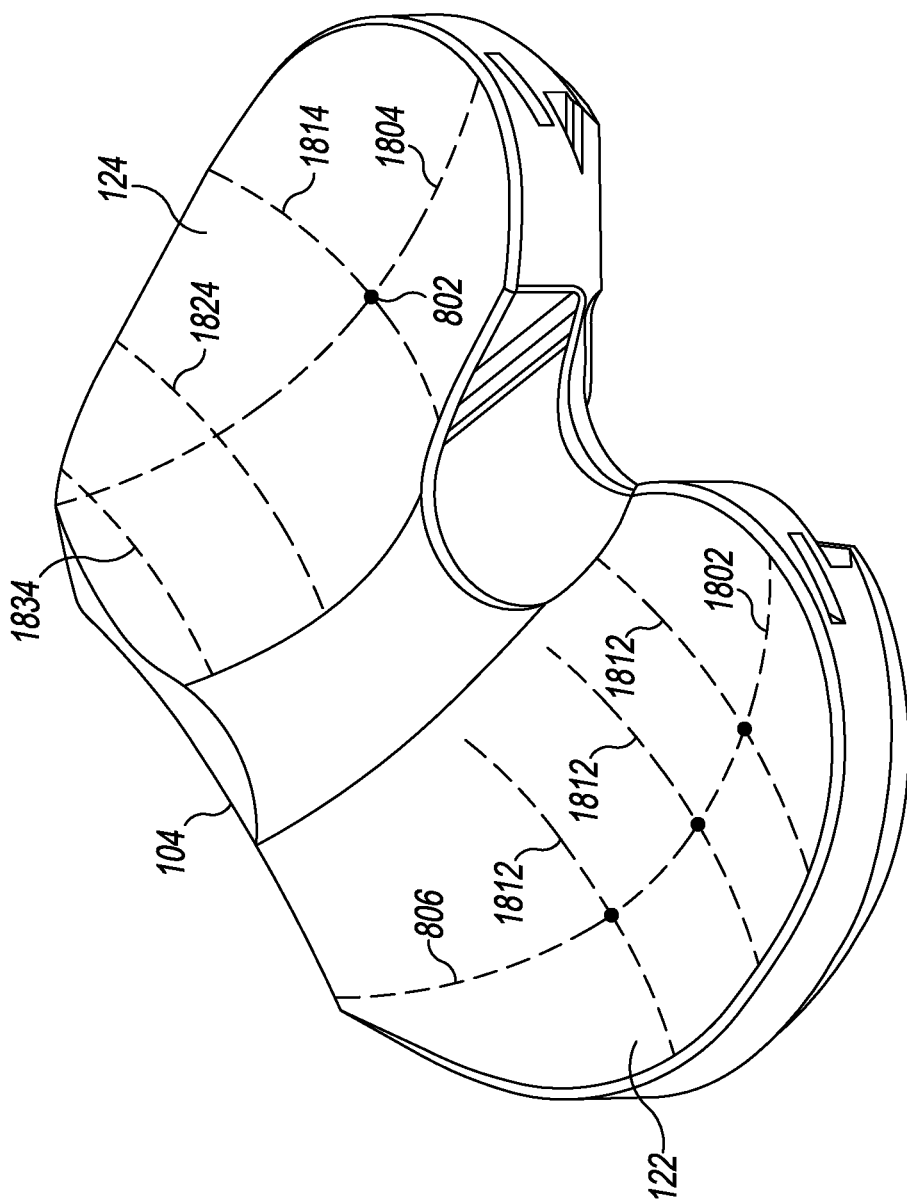
FIG. 18 is a perspective view of the tibial insert of FIG. 8 illustrating sagittal and coronal curvatures of the articular surfaces of the tibial insert.

Referring now to FIGS. 18-27, as discussed above the lateral and medial articular surfaces 122, 124 have different contours such that the articular surfaces 122, 124 are asymmetric with each other. For example, as shown in FIG. 18, the lateral articular surface 122 includes a concave curvature 1802 when viewed in an anterior-posterior complex cross-section taken along the arcuate articular path 806. It should be appreciated that the anterior-posterior complex concave curvature 1802 of the arcuate articular path 806 does not lie on a single sagittal plane due to the arcuate shape of the arcuate articular path 806 when viewed in a transverse plane. Additionally, the lateral articular surface 122 has a concave curvature 1812 when viewed in a cross-section taken orthogonal to the arcuate articular path 806. The cross-sectional concave curvature 1812 is uniform at each point along the arcuate articular path 806 (shown in FIG. 18 by multiple concave curvatures 1812). That is, the cross-section concave curvature 1812 of the arcuate articular path 806 is uniform along the arcuate articular path 806 in the general anterior-to-posterior direction (which also curves in the medial-lateral direction due to the arcuate shape of the arcuate articular path 806). Again, it should be appreciated that the cross-section concave curvature 1812 does not lie directly on the coronal planes of the lateral articular surface 122 due to the arcuate shape of the arcuate articular path 806 when viewed in a transverse plane.

Conversely, the medial articular surface 124 is defined by a sagittal concave curvature 1804 and a plurality of non-uniform coronal curvatures 1814, 1824, 1834. However, as indicated in FIG. 18, the coronal curvature of the medial articular surface 124 is uniform posteriorly of the medial dwell point 802 and defined by the coronal curvature 1814. Conversely, anterior of the medial dwell point 802, the coronal curvature of the medial articular surface is non-uniform and defined by the coronal curvatures 1824 and 1834.

In some embodiments, the coronal conformity between the medial articular surface 124 and the medial condyle 114 in not uniform across the coronal curvatures 1814, 1824, 1834 and/or across degrees of flexion of the femoral component 102 on the tibial insert 104. For example, in the illustrative embodiment, the coronal conformity between the medial articular surface 124 and the medial condyle 114 (i.e., the amount at which the radius of curvature defining the coronal curvature of the medial articular surface 124 at a particular contact point and the radius of curvature defining the contact point (or region) of the condyle surface 400 of the medial condyle 114 match) is less between the coronal curvature 1814 and the condyle surface 400 of the medial condyle 114 at a particular degree of flexion (e.g., at 30.0 degrees of flexion) than between the coronal curvature 1824 or 1834 and the condyle surface 400 of the medial condyle 114 at the particular degree of flexion. That is, at a particular degree of flexion, the coronal conformity between the coronal curvature 1824 and the condyle surface 400 of the medial condyle 114 is greater than the coronal conformity between the coronal curvature 1814 (e.g., at the medial dwell point 802) and the condyle surface 400 of the medial condyle 114. While the coronal curvature of the medial articular surface 124 is design so as to avoid impingement and/or unintended contact between the femoral component 102 and the tibial insert 104, it should also be appreciated that because the coronal conformity between the medial articular surface 124 and the medial condyle 114 increases anterior of the medial dwell point 802 at a particular degree of flexion (e.g., at 30.0 degrees of flexion), anterior translation of the medial condyle 114 may be limited, restricted, or otherwise reduced.

Figure 19:
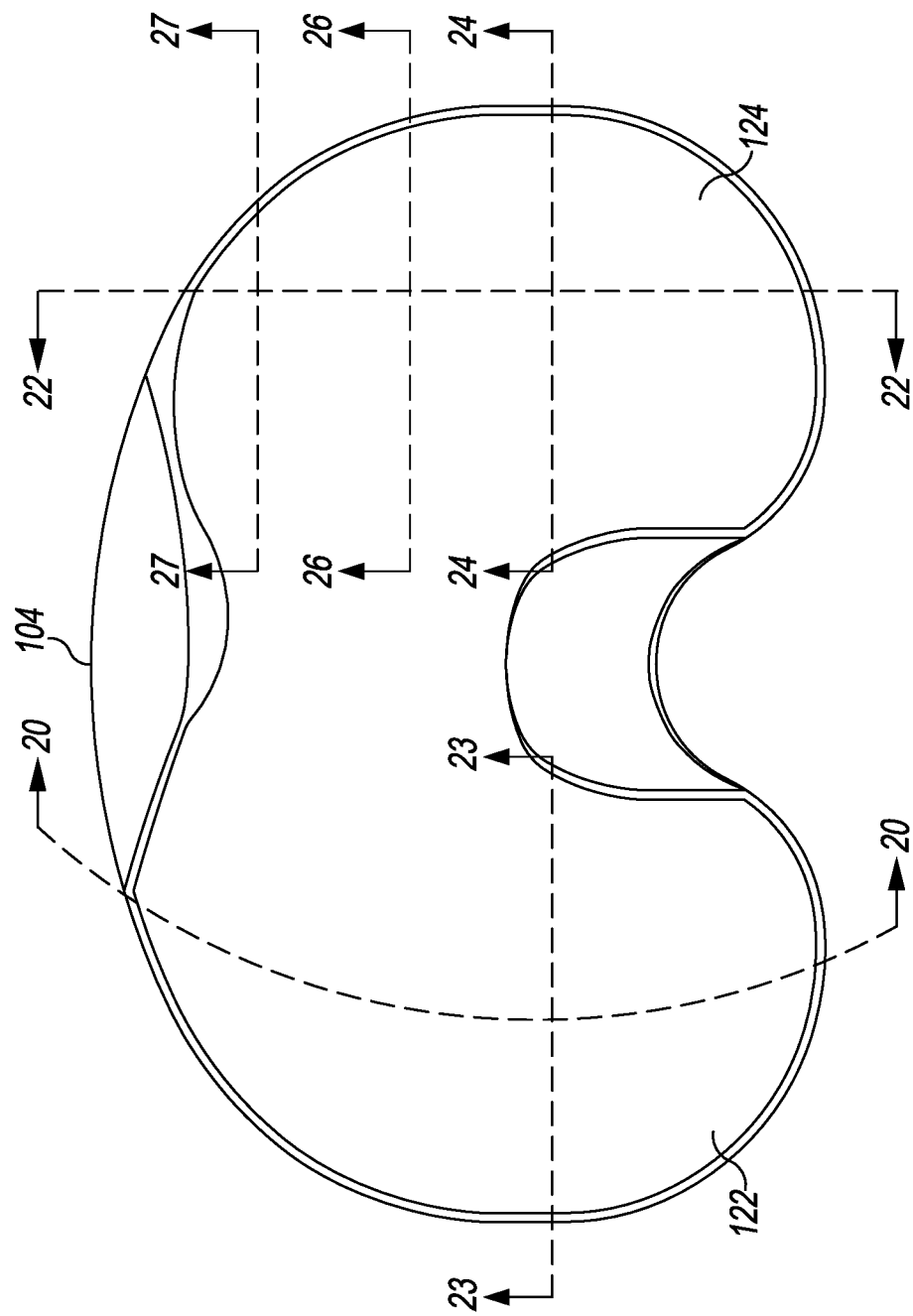
FIG. 19 is a superior plan view of the tibial insert of FIG. 8 showing several cross-sectional cut lines.
Figure 20:
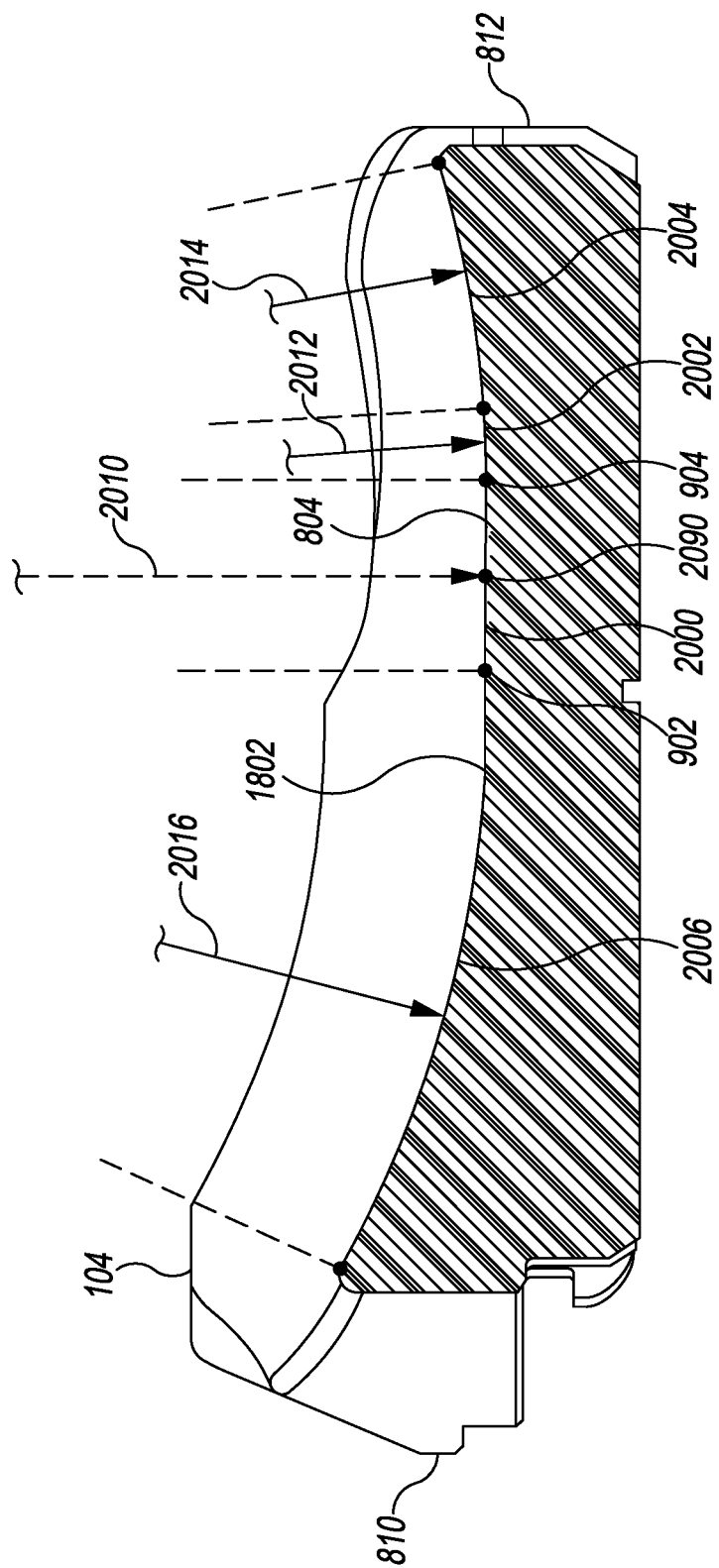
FIG. 20 is a cross-sectional view of a lateral articulation surface of an embodiment of the tibial insert of FIG. 8 in a complex plane along the line 20-20 in FIG. 19.

Referring now to FIG. 20, an illustrative embodiment of the anterior-posterior complex concave curvature 1802 of the lateral articular surface 122 is shown in a cross-section of the tibial insert 104 taken generally along the line 20-20 of FIG. 19 (i.e., along the arcuate articular path 806). The illustrative anterior-posterior complex concave curvature 1802 includes a semi-planar section 2000 corresponding to the dwell region 804, a first set of curved sections extending posteriorly of the flat section 2000 and an anterior curved section 2006 extending anteriorly of the flat section 2000. The first set of curved sections illustratively include a first curved section 2002 and a second curved section 2004.

As discussed above the flat section 2000 (i.e., the dwell region 804) is semi-planar and extends from anterior-most end 902 to a posterior-most end 904. Again, the flat section 2000 is "semi-planar" in that it may be defined as a planar section as shown in FIG. 20 or as a curved section having a radius that is sufficiently large so as to approximate a planar section. For example, in an illustrative embodiment, the flat section 2000 is defined by a large radius of curvature 2010 that has a length of at least three times the length of a radius of curvature that defines either adjacent curved section (i.e., curved section 2012 and curved section 2016). In such embodiments, the flat section 2000 includes a dwell point 2090 that defines the distal-most point of the flat section 2000 and extends for about 1.15 degrees anterior of the dwell point 2090 and about 1.58 degrees posterior of the dwell point 2090 for a total arc length of about 2.73 degrees.

Illustratively, the first curved section 2002 of the first set of curved sections extends posteriorly from the posterior-most end 904 of the flat section 2000 for about 3.4 degrees and is defined by a constant radius of curvature 2012. The second curved section 2004 is adjacent to the first curved section 2002, extends posteriorly therefrom for an arc length in the range of about 13.2 degrees to about 13.7 degrees depending on the size of the tibial insert 104. The second curved section 2004 is defined by a constant radius of curvature 2014. In an illustrative embodiment, the radius of curvature 2014 is less than the radius of curvature 2012 (i.e., the radii of curvature of the anterior-posterior complex concave curvature 1802 decrease posteriorly). In other embodiments, however, the first set of curved sections that extend posteriorly from the flat section 2000 may include additional curved sections to smoothly open up the posterior side of the anterior-posterior complex concave curvature 1802 and/or be defined by a gradually or continuously decreasing radii as discussed above in regard to the femoral component 102.

The anterior curved section 2006 extends anteriorly from the anterior-most end 902 of the flat section 2000 for an arc length in the range of about 33.5 degrees to about 34.4 degrees, depending on the size of the tibial insert 104. In an illustrative embodiment, the radius of curvature 2016 is less than the radius of curvature 2012 and greater than the radius of curvature 2014.

Figure 21:
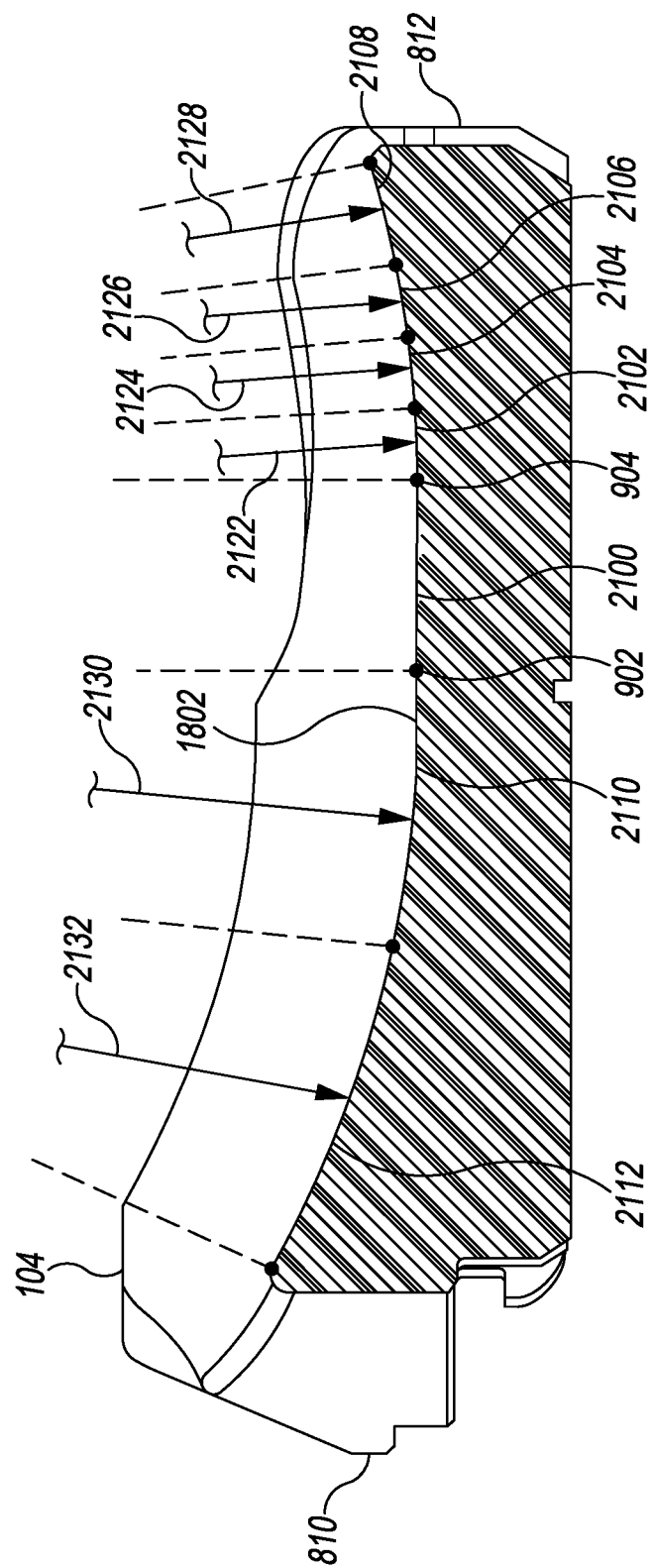
FIG. 21 is a cross-sectional view of a lateral articulation surface of another embodiment of the tibial insert of FIG. 8 in a complex plane along the line 20-20 in FIG. 19.

Referring now to FIG. 21, in another embodiment, the anterior-posterior complex concave curvature 1802 may include a flat or planer section 2100 corresponding to the dwell region 804, a first set of curved sections extending posteriorly of the flat section 2100 and a second set of curved sections extending anteriorly of the flat section 2100. As discussed above the flat section 2100 (i.e., the dwell region 804) extends from anterior-most end 902 to a posterior-most end 904.

The first set of curved sections illustratively include a first curved section 2102, a second curved section 2104, a third curved section 2106, and a fourth curved section 2108. The first curved section 2102 extends for about 5.0 degrees and is defined by a constant radius of curvature 2122. The second curved section 2104 extends for about 5.0 degrees and is defined by a constant radius of curvature 2124. The third curved section 2106 extends for about 5.0 degrees and is defined by a constant radius of curvature 2126. And, the fourth curved section 2108 extends for 18.0 degrees and is defined by a constant radius of curvature 2128. In some embodiments, however, the first set of curved sections that extend posteriorly from the flat section 2100 may include additional curved sections to smoothly open up the posterior side of the anterior-posterior complex concave curvature 1802 and/or be defined by a gradually or continuously decreasing radii as discussed above in regard to the femoral component 102. In an illustrative embodiment, the radii of curvature of the first sec of curved sections increases posteriorly. That is, the radius of curvature 2128 is greater than the radius of curvature 2126, which is greater than the radius of curvature 2124, which is greater than the radius of curvature 2122.

The second set of curved sections illustratively includes a fifth curved section 2110 and a sixth curved section 2112. The fifth curved section 2110 extends for about 15.0 degrees and is defined by a radius of curvature 2130. And, the sixth curved section 2112 extends for about 35.0 degrees and is defined by a radius of curvature 2132. In an illustrative embodiment, the radius of curvature 2130 is greater than the radius of curvature 2132.

Figure 22:
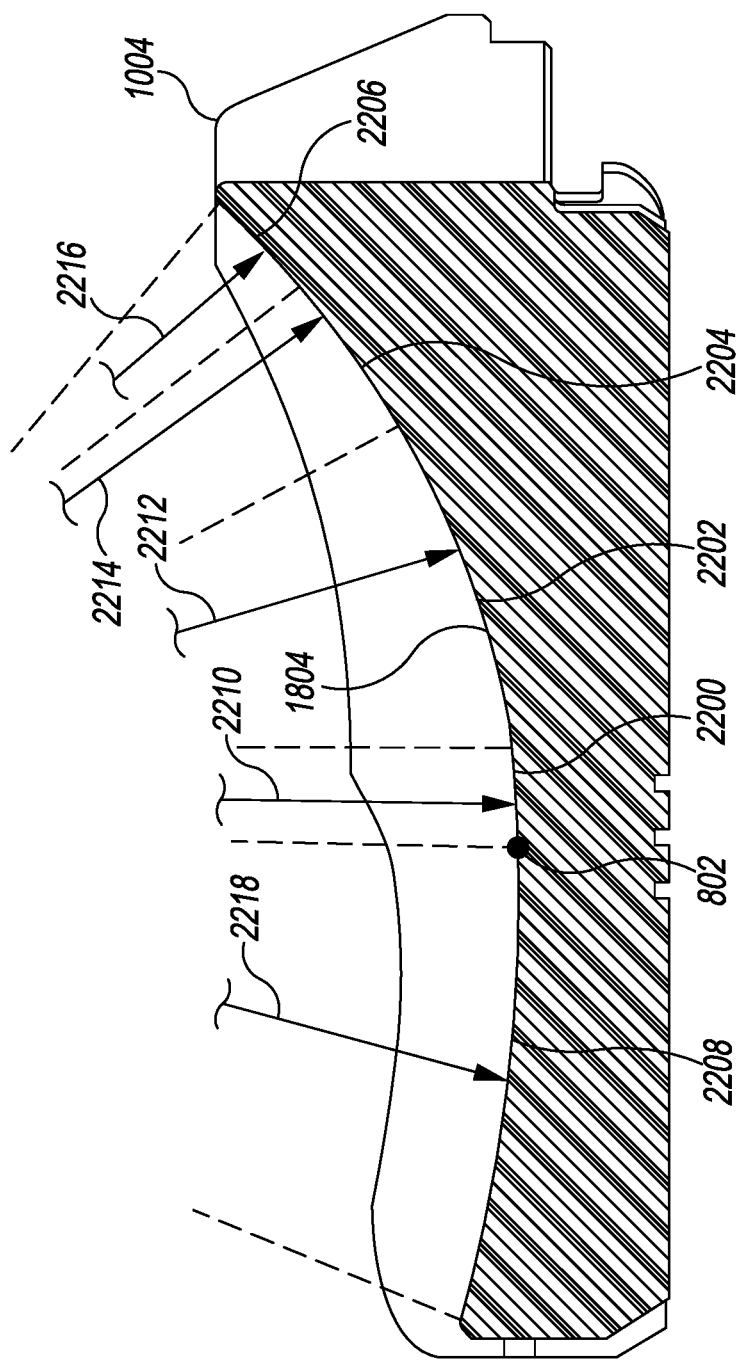
FIG. 22 is a cross-sectional view of a medial articulation surface of an embodiment of the tibial insert of FIG. 8 in a sagittal plane along the line 22-22 in FIG. 19.

Referring now to FIG. 22, an illustrative embodiment of the medial sagittal concave curvature 1804 of the tibial insert 104 is shown in a cross-section taken generally along the line 22-22 of FIG. 19, which generally matches the sagittal concave curvature 1804 of FIG. 18. The illustrative medial sagittal concave curvature 1804 includes a first curved section 2200, a second curved section 2202 anteriorly adjacent the first curved section 2200, third curved section 2204 anteriorly adjacent the second curved section 2202, a fourth curved section 2206 anteriorly adjacent the third curved section, and a fifth curved section 2208 posteriorly adjacent the first curved section 2200. Illustratively, the medial dwell point 802 lies at the intersection of the first curved section 2200 and the fifth curved section 2208. However, in other embodiments, the dwell point 802 may lie on the first curved section 2200 or the fifth curved section 2208.

The first curved section 2200 extends from the dwell point 802 anteriorly for about 5.2 degrees and is defined by a constant radius of curvature 2210. The second curved section 2202 extends anteriorly from the first curved section 2200 for an arc length in the range of about 14.8 degrees to about 24.8 degrees, depending on the size of the tibial insert 104, and is defined by a constant radius of curvature 2212. The third curved section 2204 extends anteriorly from the second curved section 2202 for an arc length in the range of about 10.7 degrees to about 20.7 degrees, depending on the size of the tibial insert 104, and is defined by a constant radius of curvature 2214. The fourth curved section 2206 extends anteriorly from the third curved section 2204 for an arc length in the range of about 0.2 degrees to about 6.3 degrees, depending on the size of the tibial insert 104, and is defined by a constant radius of curvature 2216. And, the fifth curved section 2208 extends posteriorly from the first curved section 2200 for an arc length in the range of about 15.9 degrees to about 17.4 degrees, depending on the size of the tibial insert 104, and is defined by a constant radius of curvature 2218. In an illustrative embodiment, the radius of curvature 2218 is greater than the radius of curvature 2210. Additionally, in an illustrative embodiment, the radius of curvature 2212 is less than each of the radii of curvatures 2210, 2214, and 2216.

The medial sagittal concave curvature 1804 of the tibial insert 104 may be shaped differently to have a different curvature in other embodiments. For example, in another embodiment, the second curved section 2202 may extend anteriorly from the first curved section 2200 for about 24.8 degrees. The third curved section 2204 may extend anteriorly from the second curved section 2202 for about 15.0 degrees. And, the fifth curved section 2208 may extend posteriorly from the first curved section 2200 for about 19.0 degrees.

In some embodiments, the sagittal conformity between the medial articular surface 124 and the medial condyle 114 is not uniform across degrees of flexion. For example, as discussed in more detail below in regard to FIGS. 28-43, the overall sagittal conformity between the medial sagittal concave curvature 1804 of the tibial insert 104 and the sagittal convex curvature of the medial condyle 114 of the femoral component 102 may be greater at a particular degree of flexion (e.g., at 30 degrees of flexion) than at extension. The overall sagittal conformity between the sagittal curvatures of the femoral component 102 and the tibial insert 104 (i.e., the conformity across the complete sagittal curvature rather than only at a particular contact point) can be defined as the amount of overall gap between those curvatures at a particular degree of flexion. As such, the sagittal curvature of the medial condyle 114 of the femoral component 102 matches the sagittal curvature of the medial articular surface 124 of the tibial insert the greatest amount at the particular degree of flexion (e.g., at 30 degrees of flexion). The sagittal conformity may be increased further under loading conditions (i.e., the femoral component 102 may be compressed further onto the tibial insert 104 such that the sagittal conformity at the particular degree of flexion is further increased). By increasing the overall sagittal conformity between the medial condyle 114 and the medial articular surface 124 during flexion, relative to extension, anterior translation of the femoral component 102 on the medial articular surface 124 may be reduced at that particular degree of flexion (e.g., at 30 or 35 degrees of flexion).

Additionally, at a particular degree of flexion (e.g., 30 degrees of flexion) the sagittal conformity between the medial condyle 114 and the sagittal curvatures 2200, 2202, 2204, 2206. For example, in an illustrative embodiment, the sagittal conformity between the medial articular surface 124 and the medial condyle 114 (i.e., the amount at which the radius of curvature defining the sagittal curvature of the medial articular surface 124 at a particular contact point and the radius of curvature defining the contact point on the condyle surface 400 of the medial condyle 114 match) is less between the fourth curved section 2206 and the condyle surface 400 of the medial condyle 114 at a particular degree of flexion (e.g., at 30.0 degrees of flexion) than between the first curved section 2200 and the condyle surface 400 of the medial condyle 114 at the particular degree of flexion. That is, at a particular degree of flexion, the sagittal conformity at the point (or region) of contact between the first curved section 2200 and the condyle surface 400 of the medial condyle 114 is greater than the sagittal conformity between the point (or region) of contact between the fourth curved section 2206 and the condyle surface 400 of the medial condyle 114. As such, it should be appreciated that because the sagittal conformity between the medial articular surface 124 and the medial condyle 114 increases anterior of the medial dwell point 802 at a particular degree of flexion (e.g., at 30.0 degrees of flexion), anterior translation of the medial condyle 114 on the medial articular surface 124 may be limited, restricted, or otherwise reduced.

Additionally, it should be appreciated that the sagittal conformity between the medial articular surface 124 and the medial condyle 114 at the medial dwell point 802 may increase through a particular range of flexion in some embodiments. For example, in an illustrative embodiment, as the femoral component 102 is flexed through a particular range of flexion, the point of contact between the femoral component 102 and the tibial insert 104 moves along the curved surface section 404 defined by the decreasing radii of curvature. As such, in the illustrative embodiment, the sagittal curvature of the medial articular surface 124 at the medial dwell point 802 is designed to have the greatest amount of sagittal conformity with the medial condyle 114 at a particular degree of flexion (e.g., at 30 degrees of flexion) at which the point of contact between the femoral component 102 and the tibial insert 104 occurs on the curved surface section 404, resulting in an increasing amount of sagittal conformity between the femoral component 102 and the tibial insert 104 as the particular degree of flexion is approached.

Figure 23:
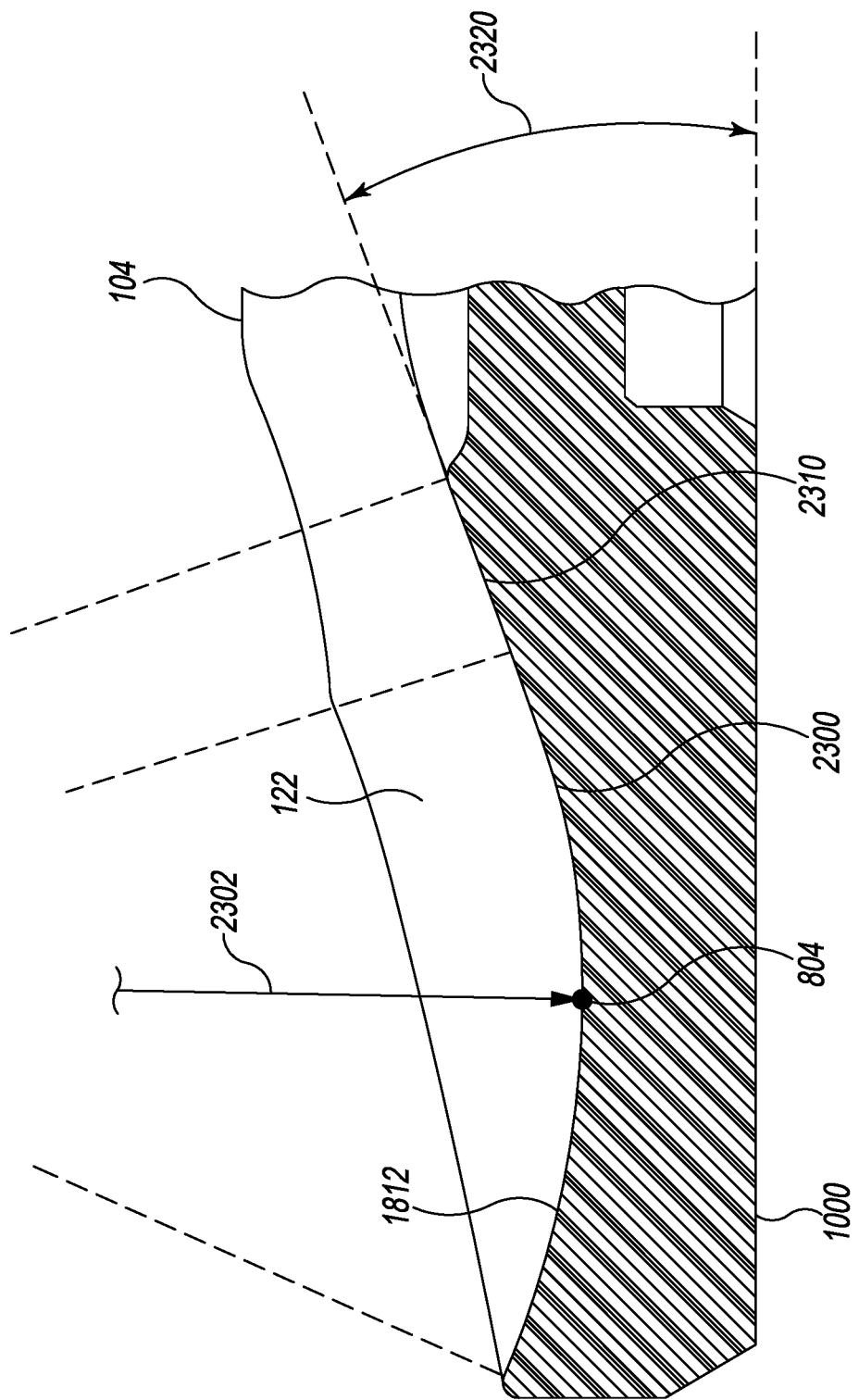
FIG. 23 is a cross-sectional view of the lateral articulation surface of an embodiment of the tibial insert of FIG. 8 in a coronal plane along the line 23-23 in FIG. 19.

Referring now to FIG. 23, an illustrative embodiment of the cross-section concave curvature 1812 of the lateral articular surface 122 of the tibial insert 104 is shown in a cross-section taken generally along the line 23-23 of FIG. 19, which generally matches the uniform cross-section curvature 1812 of FIG. 18. As discussed above, in the illustrative embodiment, the cross-section curvature 1812 of the lateral articular surface 122 is uniform along the anterior-posterior complex concave curvature 1802 and has a single curved section 2300 having a constant radius of curvature 2302. The curved section 2300 extends medially (i.e., inboard) of the lateral dwell region 804 for about 25 degrees and extends laterally (i.e., outboard) of the lateral dwell region 804 for an arc length in the range of about 18.7 degrees to about 31.1 degrees for an overall arc length of about 43.7 degrees to about 56.1 degrees, depending on the size of the tibial insert 104. Additionally, the cross-section curvature 1812 of the lateral articular surface 122 includes a planar section 2310 that is tangent to and extends medially of (i.e., inboard) the medial-most point of the curved section 2300. Additionally, as shown in FIG. 23, the planar section 2310 is angled relative to the bottom side 1000 of the tibial insert 104 at an angle 2320 of about 25.0 degrees. The size, shape, and orientation of the planar section 2310 may be selected or designed to match the inboard shape of the femoral component 102 and/or to avoid impingement of the femoral component 102.

Figure 24:
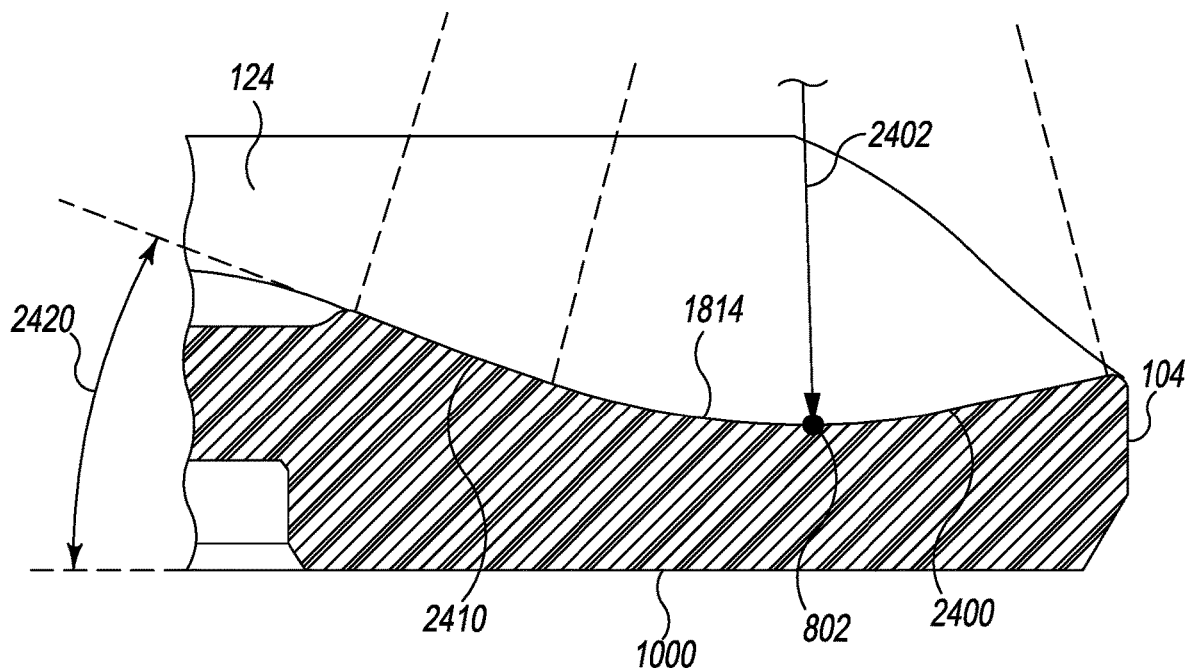
FIG. 24 is a cross-sectional view of the medial articulation surface of an embodiment of the tibial insert of FIG. 8 in a coronal plane along the line 24-24 in FIG. 19.

Referring now to FIG. 24, an illustrative embodiment of the coronal curvature 1814 of the tibial insert 104 is shown in a cross-section taken generally along the line 24-24 of FIG. 19, which generally matches the coronal curvature 1814 of FIG. 18. In the illustrative embodiment, the coronal curvature 1814 of the medial articular surface 124 is uniform posterior of the medial dwell point 802 and has a single curved section 2400 having a constant radius of curvature 2402.

The curved section 2400 extends laterally (i.e., inboard) of the medial dwell point 802 for about 25 degrees and extends medially (i.e., outboard) of the medial dwell point 802 for an arc length in the range of about 18.6 degrees to about 26.8 degrees for an overall arc length of about 43.6 degrees to about 51.8 degrees, depending on the size of the tibial insert 104. Additionally, the coronal curvature 1814 of the medial articular surface 124 includes a planar section 2410 that is tangent to and extends laterally of (i.e., inboard) the lateral-most point of the curved section 2400. As shown in FIG. 24, the planar section 2410 is angled relative to the bottom side 1000 of the tibial insert 104 at an angle 2420 of about 25.0 degrees. Similarly, to planar section 2310 of the lateral articular surface 122, the size, shape, and orientation of the planar section 2410 may be selected or designed to match the inboard shape of the femoral component 102 and/or to avoid impingement of the femoral component 102.

Figure 25:
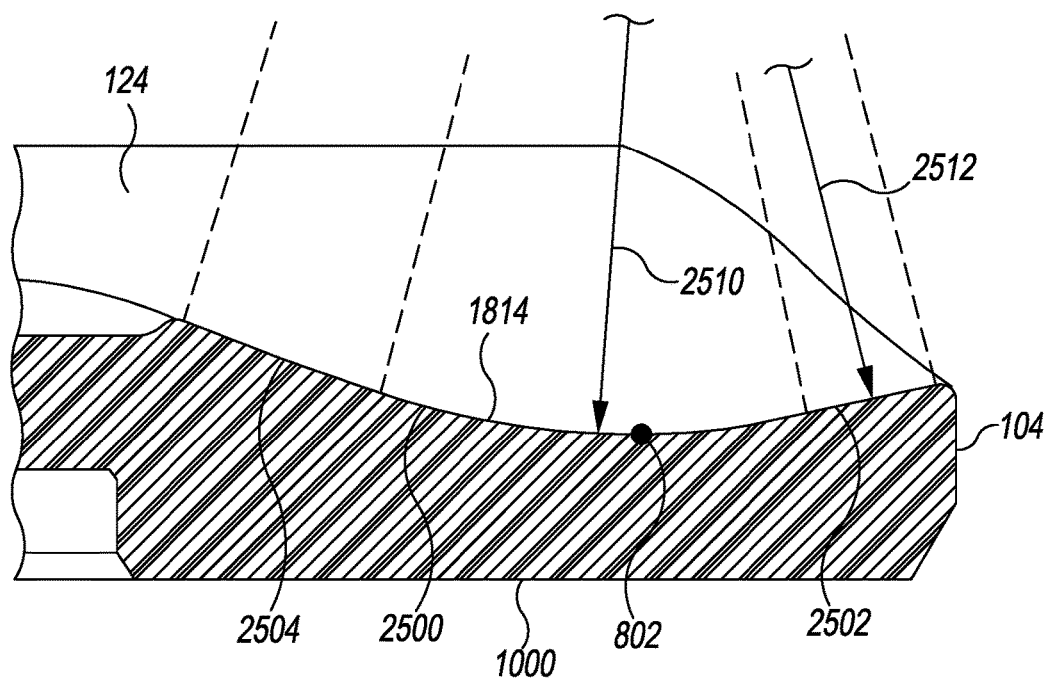
FIG. 25 is a cross-sectional view of the medial articulation surface of another embodiment of the tibial insert of FIG. 8 in a coronal plane along the line 24-24 in FIG. 19.

In other embodiments, the coronal curvature 1814 may be defined by a plurality of curved sections. For example, as shown in FIG. 25, in another embodiment, the coronal curvature 1814 may be defined by a first curved section 2500 on which the dwell point 802 lies and a second curved section 2502 located medially adjacent (i.e., outboard of) the first curved section 2500. The first curved section 2500 extends for about 20 degrees and is defined by a radius of curvature 2510, and the second curved section 2502 extends for about 10 degrees and is defined by a radius of curvature 2512. In such embodiments, the radius of curvature 2512 may be greater than the radius of curvature 2510. Additionally, the coronal curvature 1814 of FIG. 25 may include a planar section 2504 that is tangent to and extends laterally of (i.e., inboard) the lateral-most point of the curved section 2500. Similar to planar section 2410, the planar section 2504 may be angled relative to the bottom side 1000 of the tibial insert 104 at an angle of about 25.0 degrees.

Figure 26:
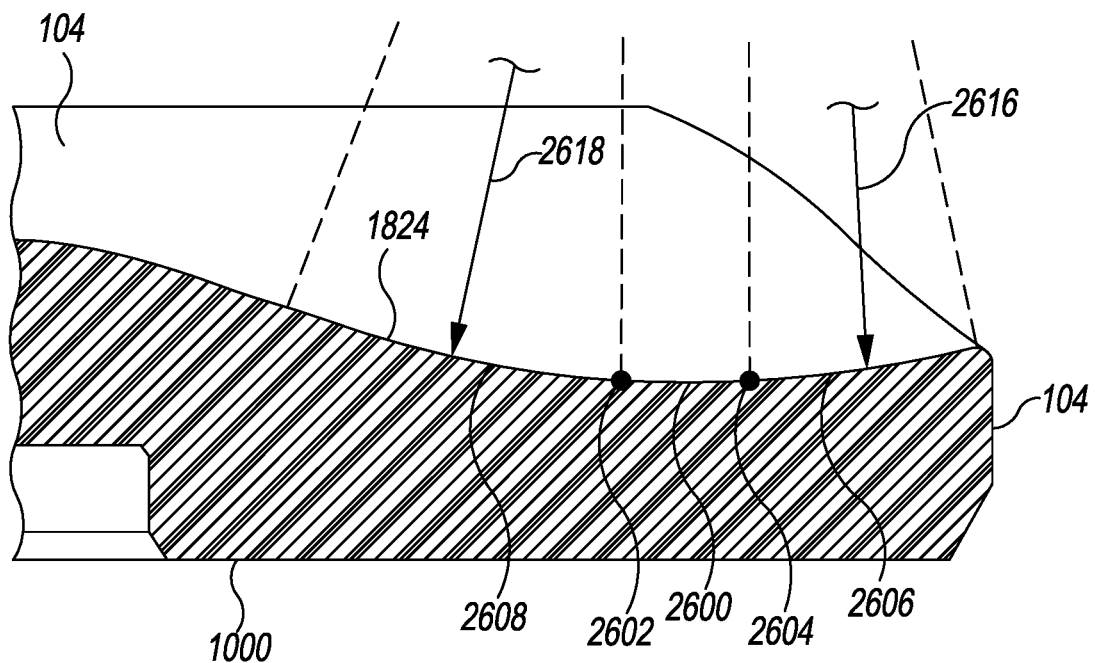
FIG. 26 is another cross-sectional view of the medial articulation surface of an embodiment of the tibial insert of FIG. 8 in a coronal plane along the line 26-26 in FIG. 19.

Referring now to FIG. 26, an illustrative embodiment of the coronal curvature 1824 of the tibial insert 104 is shown in a cross-section taken generally along the line 26-26 of FIG. 19, which generally matches the coronal curvature 1824 of FIG. 18. The coronal curvature 1824 crosses the sagittal concave curvature 1804 at an anterior-most point of the second curved section 2202 that defines the medial sagittal concave curvature 1804 (see FIG. 22). The coronal curvature 1824 includes a flat or planar section 2600 having a lateral end 2602 (i.e., an inboard end) and a medial end 2604 (i.e., an outboard end), a first curved section 2606 extending from the medial end 2604 of the planar section 2600, and a second curved section 2608 extending from the lateral end 2602 of the planar section 2600. The first curved section 2606 extends for an arc length in the range of about 14.7 degrees to about 15.7 degrees, depending on the size of the tibial insert 104, and is defined by a constant radius of curvature 2616. The second curved section 2608 extends for an arc length in the range of about 20.1 degrees to about 28.5 degrees, depending on the size of the tibial insert 104, and is defined by a constant radius of curvature 2618. In the illustrative embodiment, the radius of curvature 2618 is greater than the radius of curvature 2616.

Figure 27:
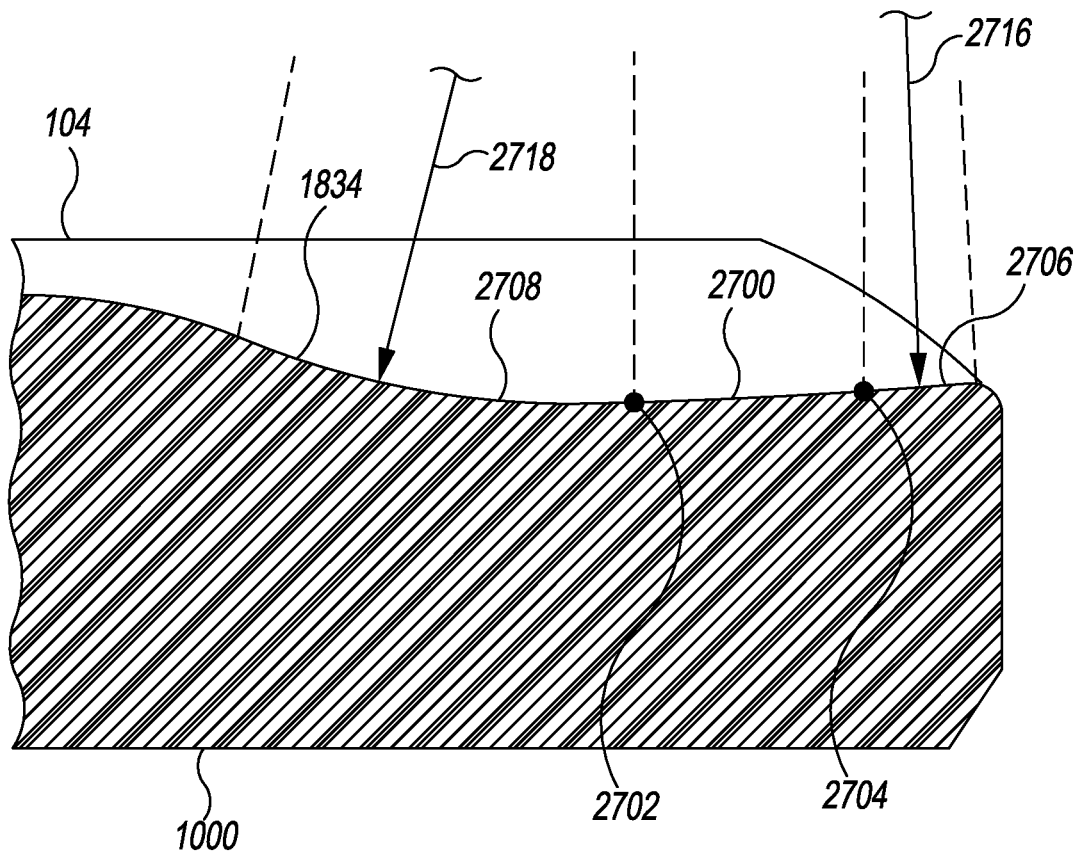
FIG. 27 is another cross-sectional view of the medial articulation surface of an embodiment of the tibial insert of FIG. 8 in a coronal plane along the line 27-27 in FIG. 19.
Figure 28:
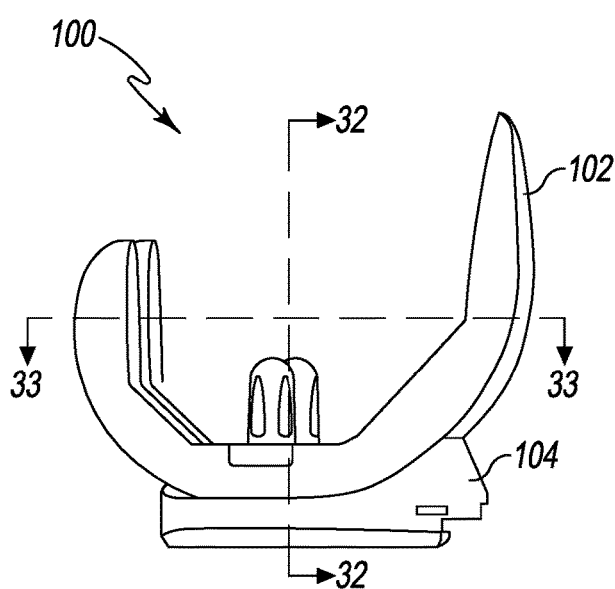
FIG. 28 is a medial elevation view of the orthopaedic knee prosthesis of FIG. 1 at about 0 degrees of flexion.

Referring now to FIG. 27, an illustrative embodiment of the coronal curvature 1834 of the tibial insert 104 is shown in a cross-section taken generally along the line 27-27 of FIG. 19, which generally matches the coronal curvature 1834 of FIG. 18. The coronal curvature 1834 crosses the sagittal concave curvature 1804 at an anterior-most point of the third curved section 2204 that defines the medial sagittal concave curvature 1804 (see FIG. 22). Similar to the coronal curvature 1824, the coronal curvature 1834 includes a flat or planar section 2700 having a lateral end 2702 (i.e., an inboard end) and a medial end 2704 (i.e., an outboard end), a first curved section 2706 extending from the medial end 2704 of the planar section 2700, and a second curved section 2708 extending from the lateral end 2702 of the planar section 2700. In some embodiments, the planar section 2700 may be angled relative to the bottom side 1000 of the tibial insert 104 at about 6.0 degrees. The first curved section 2706 extends for an arc length in the range of about 0.3 degrees to about 0.9 degrees, depending on the size of the tibial insert 104, and is defined by a constant radius of curvature 2616. The second curved section 2708 extends for an arc length in the range of about 16.4 degrees to about 24.7 degrees, depending on the size of the tibial insert 104, and is defined by a constant radius of curvature 2718. In the illustrative embodiment, the radius of curvature 2716 is greater than the radius of curvature 2718.

Figure 29:
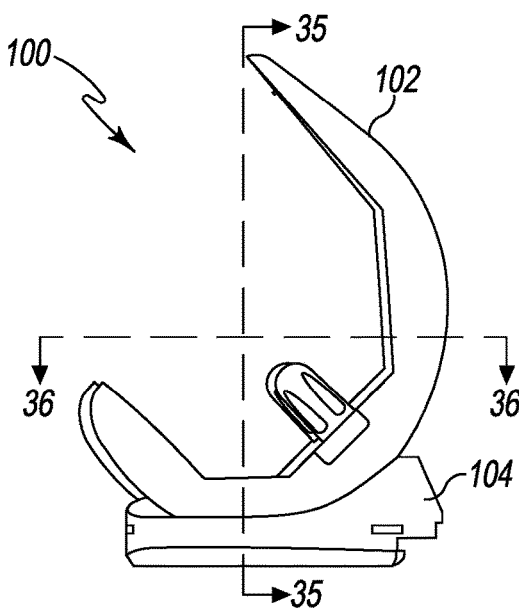
FIG. 29 is a medial elevation view of the orthopaedic knee prosthesis of FIG. 1 at about 35 degrees of flexion.
Figure 30:
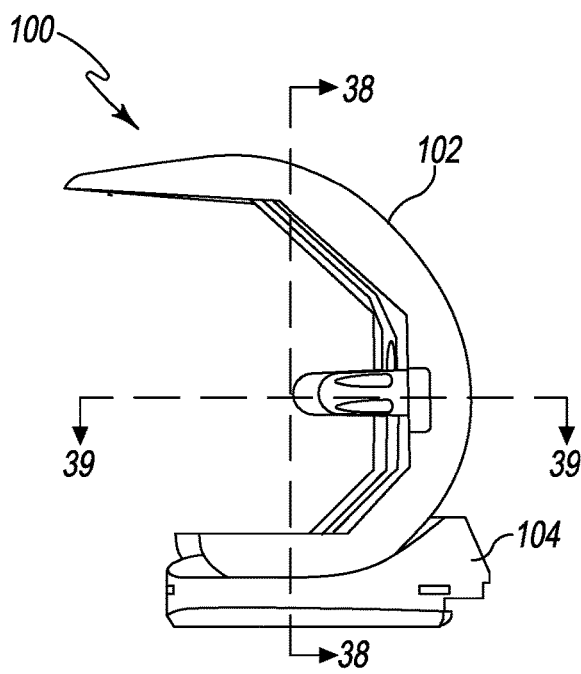
FIG. 30 is a medial elevation view of the orthopaedic knee prosthesis of FIG. 1 at about 90 degrees of flexion.
Figure 31:
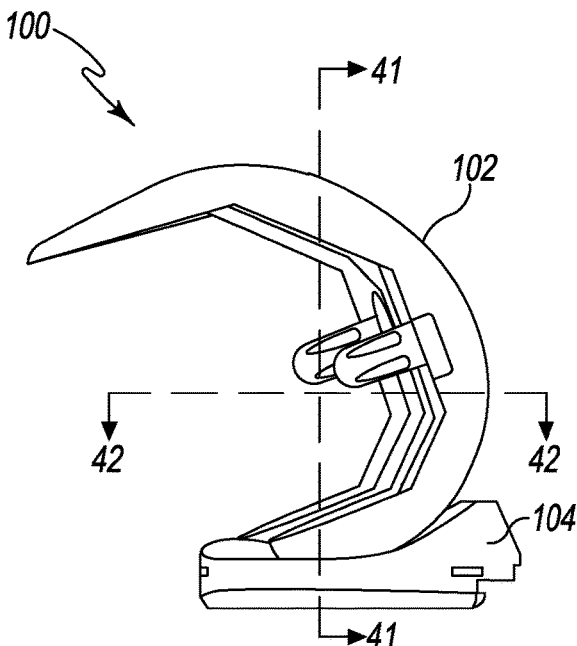
FIG. 31 is a medial elevation view of the orthopaedic knee prosthesis of FIG. 1 at about 110 degrees of flexion.

Referring now to FIGS. 28-43, as discussed above, the femoral component 102 is configured to articulate on the tibial insert 104 through a range of degrees of flexion. For example, the femoral component 102 is shown at extension (i.e., 0 degrees of flexion) in FIG. 28. In FIG. 29, the femoral component 102 has articulated to about 35 degrees of flexion. In FIG. 30, the femoral component 102 has articulated to about 90 degrees of flexion. And, in FIG. 31, the femoral component 102 has articulated to about 110 degrees of flexion.

Figure 32:
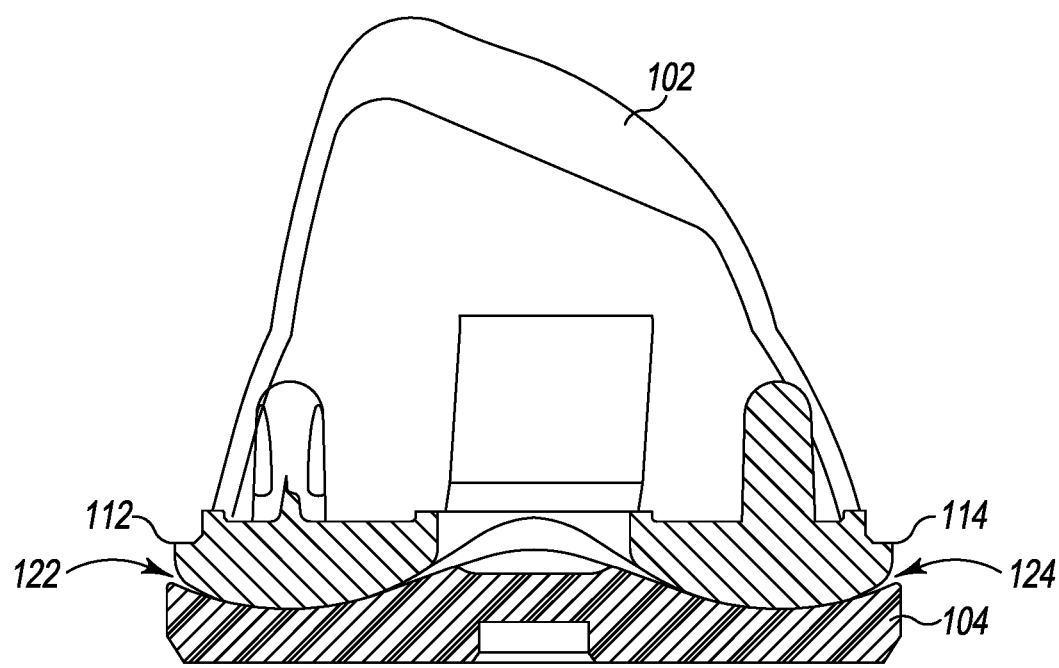
FIG. 32 is a cross-sectional view of the orthopaedic knee prosthesis of FIG. 28 in a coronal plan along the line 32-32 in FIG. 28.
Figure 33:
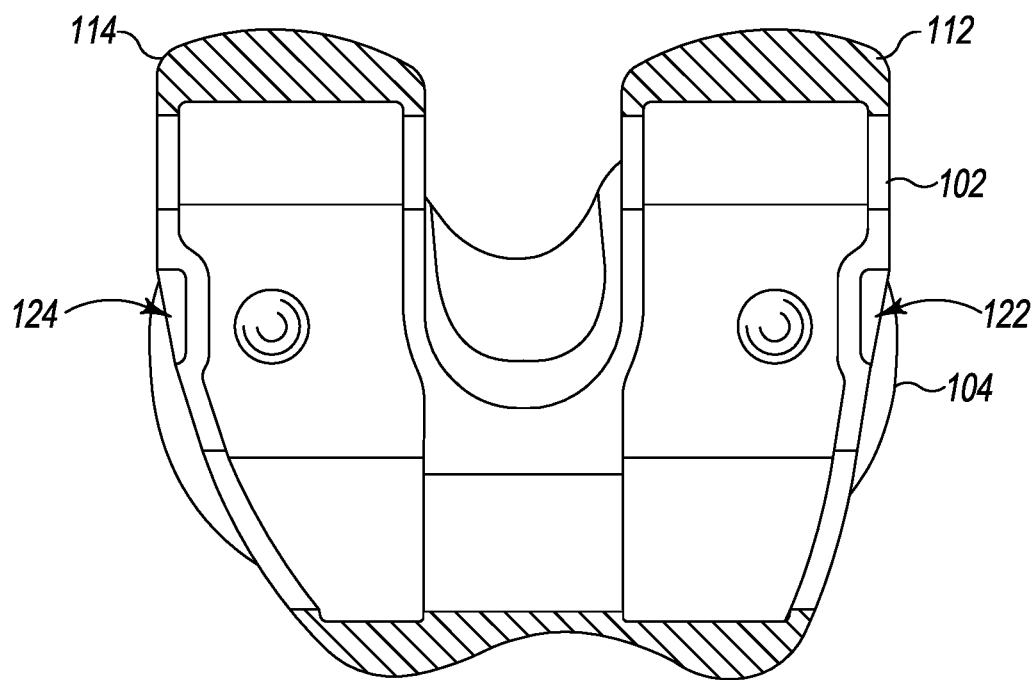
FIG. 33 is a cross-sectional view of the orthopaedic knee prosthesis of FIG. 28 in a transverse plane along the line 33-33 in FIG. 28.
Figure 34:
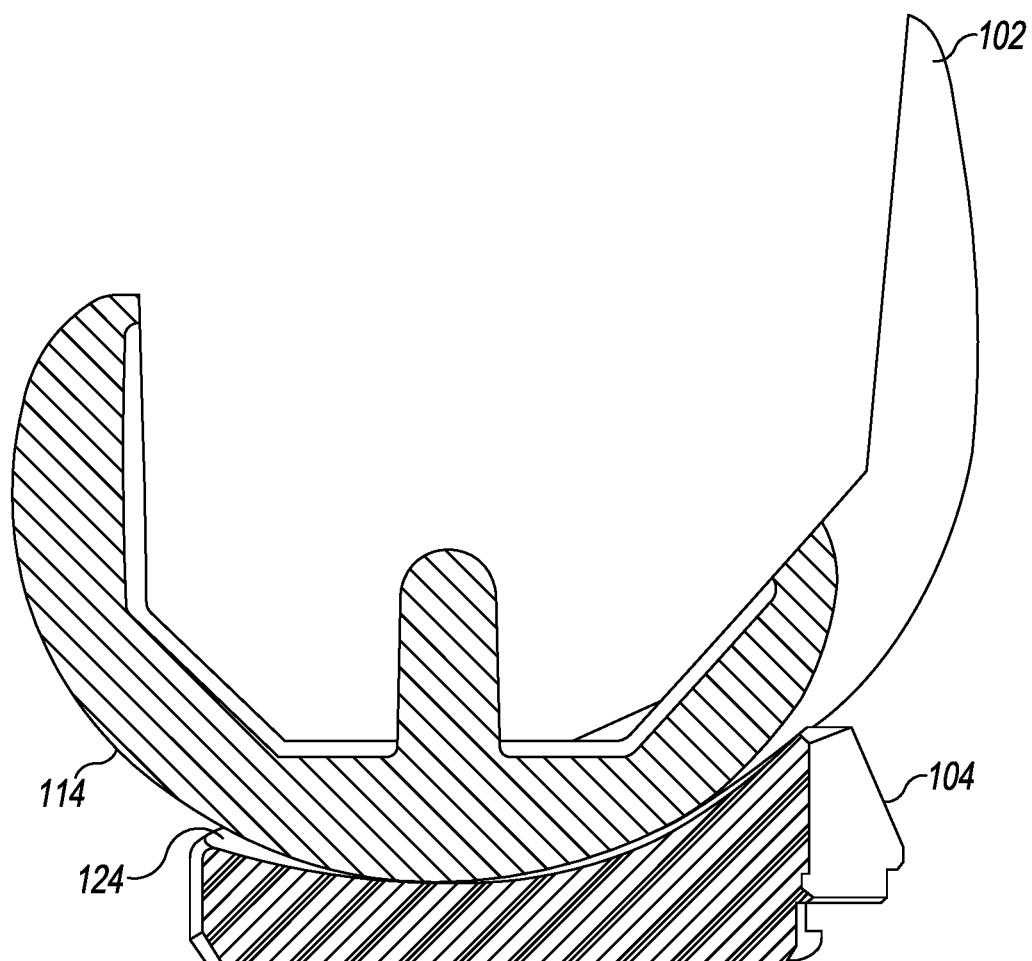
FIG. 34 is a cross-sectional view of the orthopaedic knee prosthesis of FIG. 28 in a sagittal plan along a medial dwell point of a medial articular surface of the tibial insert of the orthopaedic knee prosthesis of FIG. 28.

As discussed above, the condyles 112, 114 of the femoral component 102 may have a different amount of conformity with the articular surfaces 122, 124 at different degrees of flexion. For example, in FIGS. 32-34, the orthopaedic prosthesis 100 is shown at about 0.0 degrees of flexion. As indicated in FIG. 32, the femoral component 102 and the tibial insert 104 have an increase coronal conformity when in extension. Additionally, as shown in FIG. 33, the femoral component 102 is only slightly pivoted or rotated on the tibial insert 104. Furthermore, as shown in FIG. 34, the medial condyle 114 and the medial articular surface 124 have an overall sagittal conformity (i.e., the amount of space between the sagittal curvatures of the medial condyle 114 and the medial articular surface 124) at extension.

Figure 35:
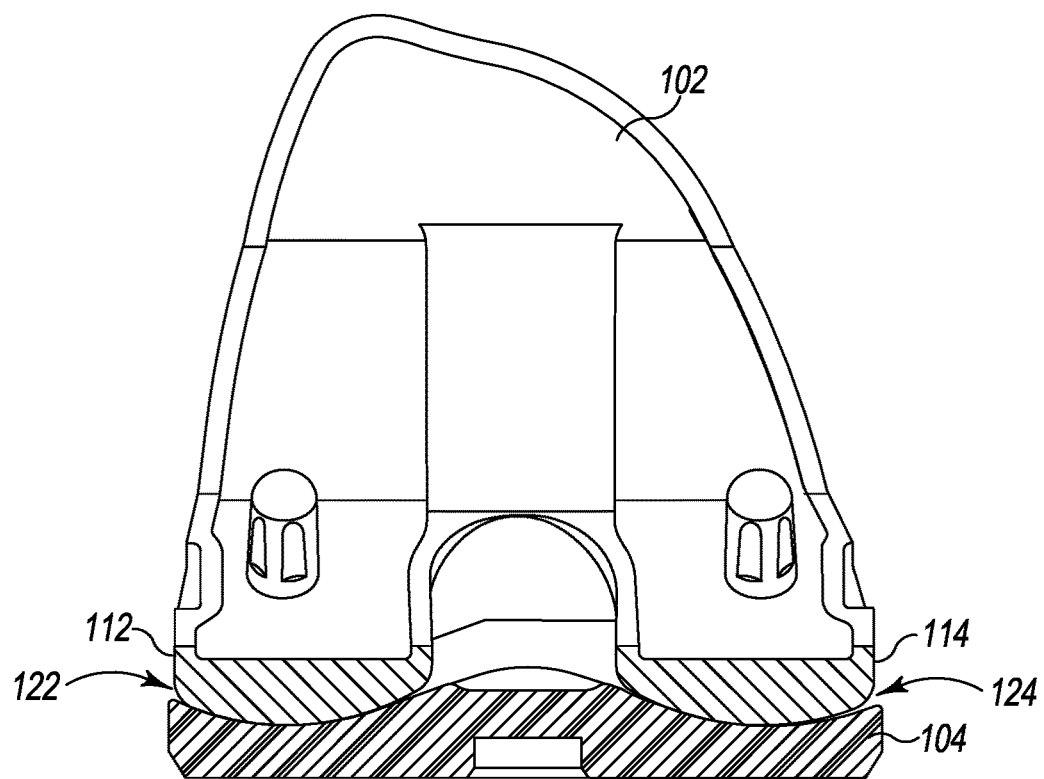
FIG. 35 is a cross-sectional view of the orthopaedic knee prosthesis of FIG. 29 in a coronal plan along the line 35-35 in FIG. 29.
Figure 36:
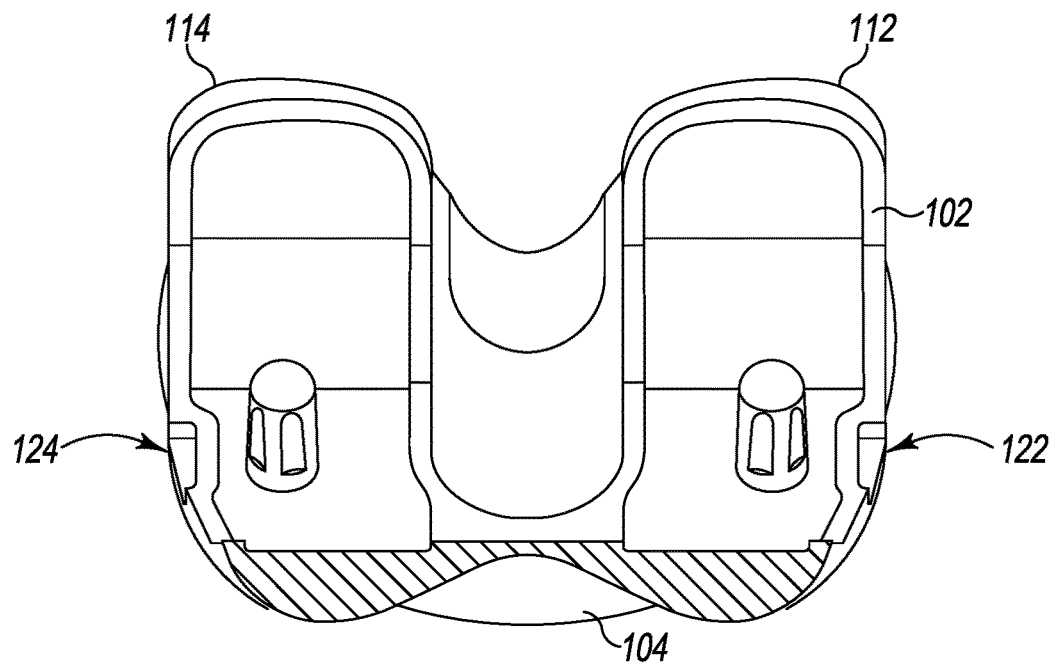
FIG. 36 is a cross-sectional view of the orthopaedic knee prosthesis of FIG. 29 in a transverse plane along the line 36-36 in FIG. 29.
Figure 37:
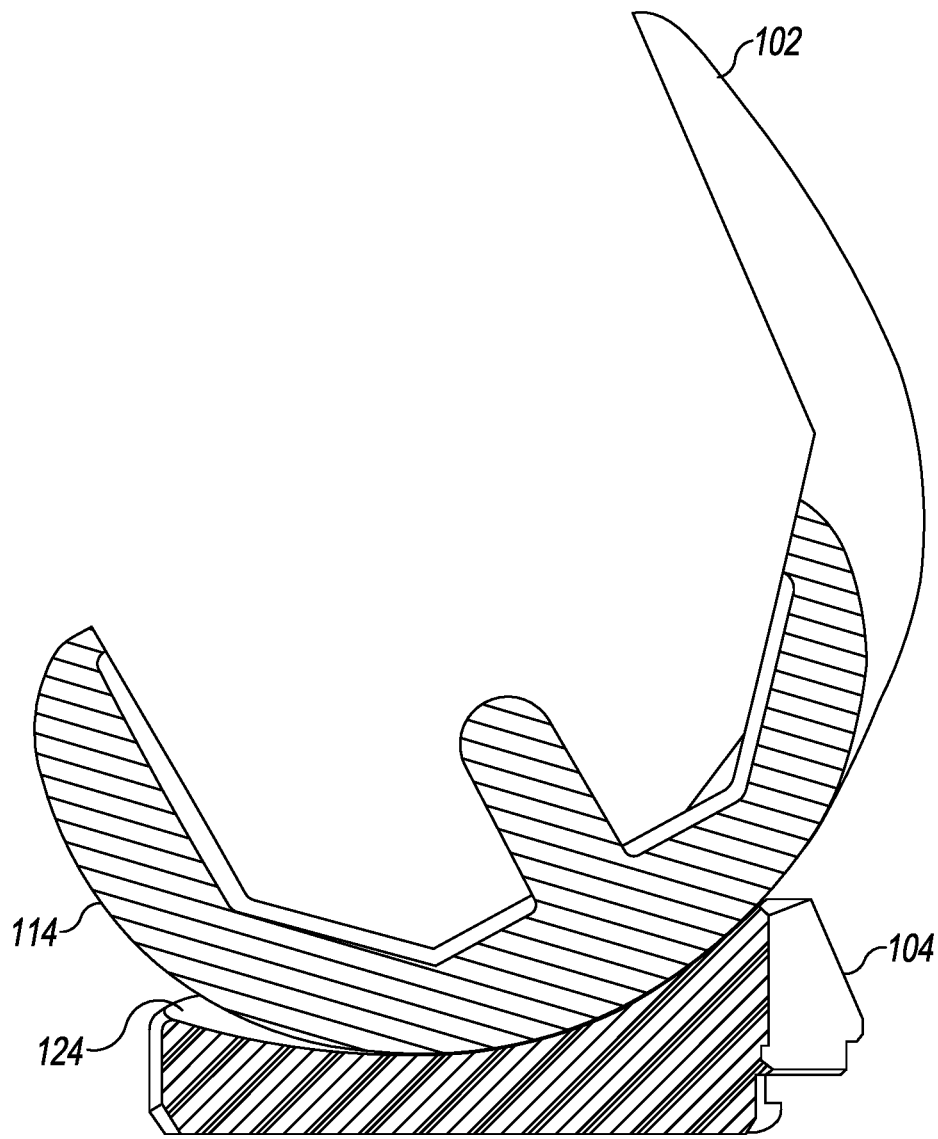
FIG. 37 is a cross-sectional view of the orthopaedic knee prosthesis of FIG. 29 in a sagittal plan along a medial dwell point of a medial articular surface of the tibial insert of the orthopaedic knee prosthesis of FIG. 29.

In FIGS. 35-37, the orthopaedic prosthesis 100 is shown at 35.0 degrees of flexion. As indicated in FIG. 35, the femoral component 102 and the tibial insert 104 has a slightly less coronal conformity relative to the extension position. Additionally, as shown in FIG. 36, the femoral component 102 is pivoted or rotated on the tibial insert 104 to a greater amount. Furthermore, as shown in FIG. 37, the medial condyle 114 and the medial articular surface 124 have an overall sagittal conformity that is increased relative to the 0.0 degrees of flexion of FIG. 34.

Figure 38:
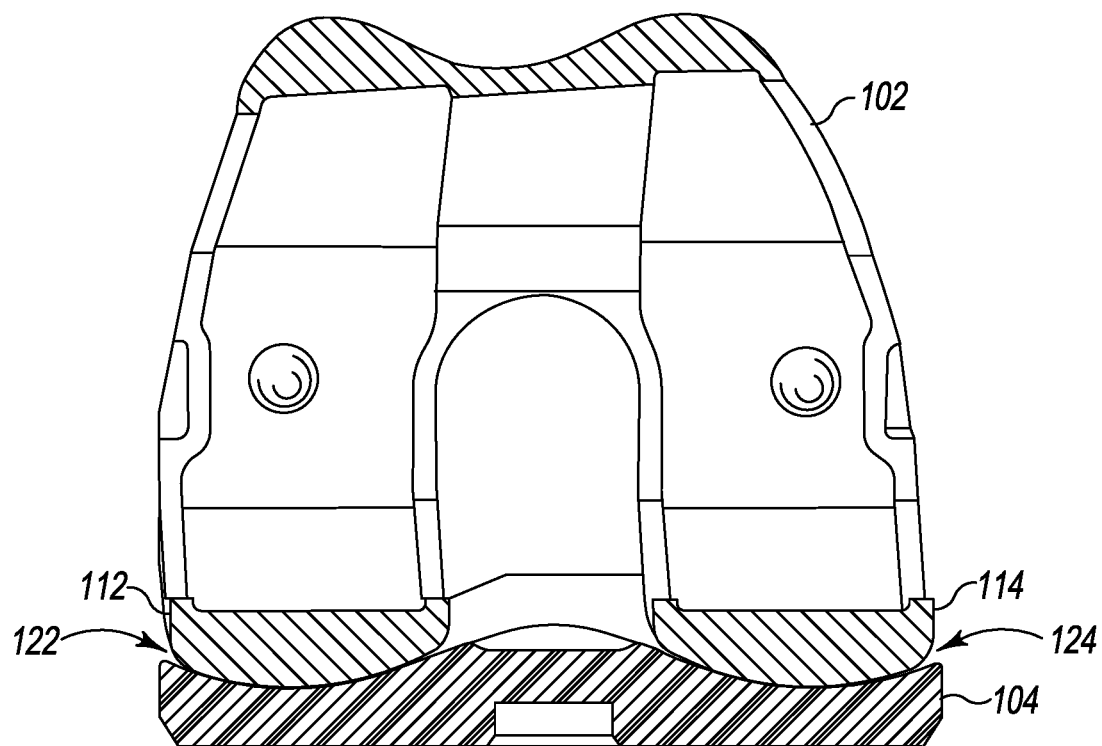
FIG. 38 is a cross-sectional view of the orthopaedic knee prosthesis of FIG. 30 in a coronal plan along the line 38-38 in FIG. 30.
Figure 39:
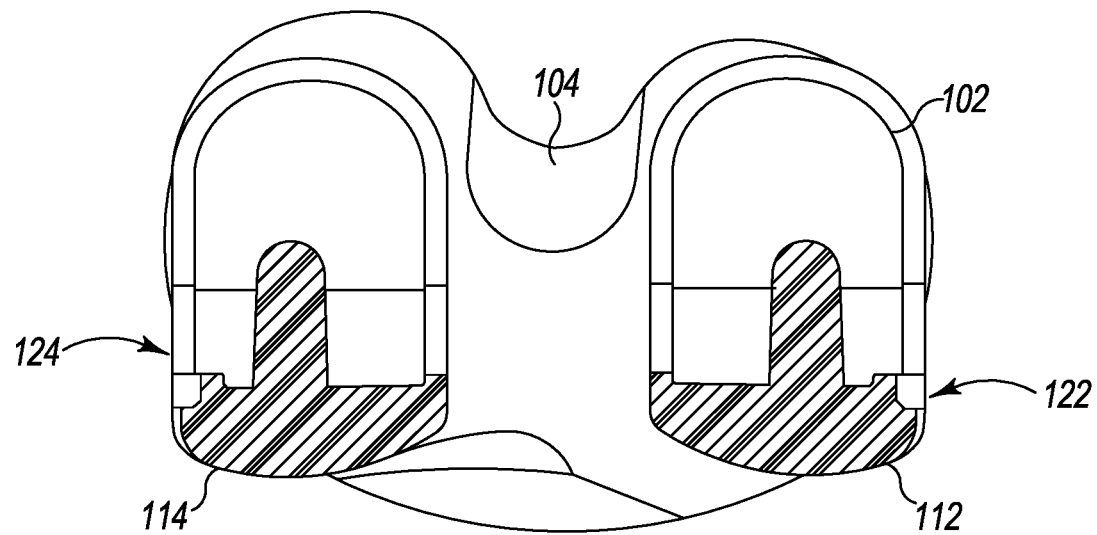
FIG. 39 is a cross-sectional view of the orthopaedic knee prosthesis of FIG. 30 in a transverse plane along the line 39-39 in FIG. 30.
Figure 40:
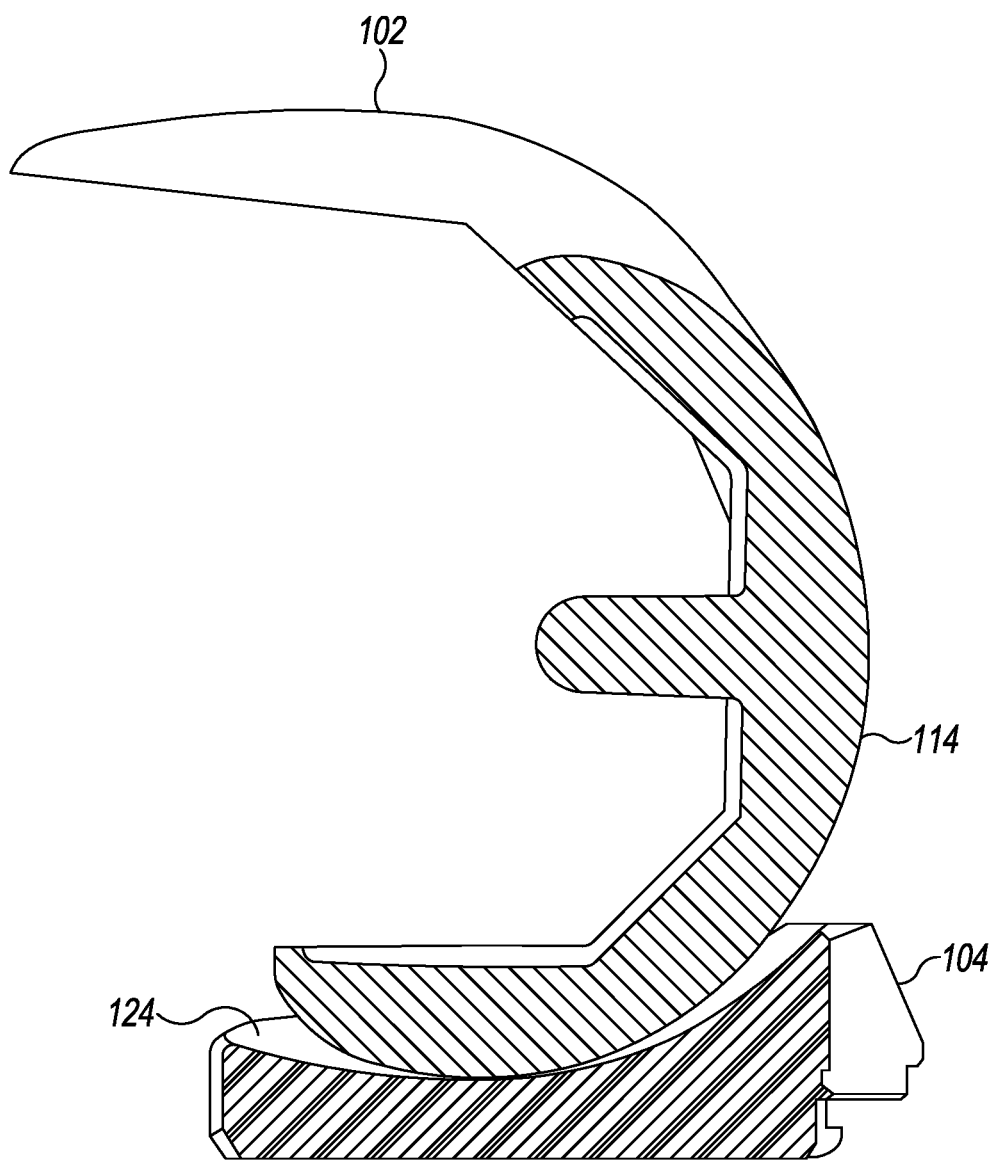
FIG. 40 is a cross-sectional view of the orthopaedic knee prosthesis of FIG. 30 in a sagittal plan along a medial dwell point of a medial articular surface of the tibial insert of the orthopaedic knee prosthesis of FIG. 30.

In FIGS. 38-40, the orthopaedic prosthesis 100 is shown at about 90 degrees of flexion. As indicated in FIG. 38, the femoral component 102 and the tibial insert 104 has less coronal conformity relative to the 35 degrees of flexion of FIGS. 34 and 35. Additionally, as shown in FIG. 39, the femoral component 102 is pivoted or rotated on the tibial insert 104 to a greater amount relative to 35 degrees of flexion of FIGS. 35 and 36. Furthermore, as shown in FIG. 40, the medial condyle 114 and the medial articular surface 124 have an overall sagittal conformity that is decreased relative to the 35.0 degrees of flexion of FIG. 37.

Figure 41:
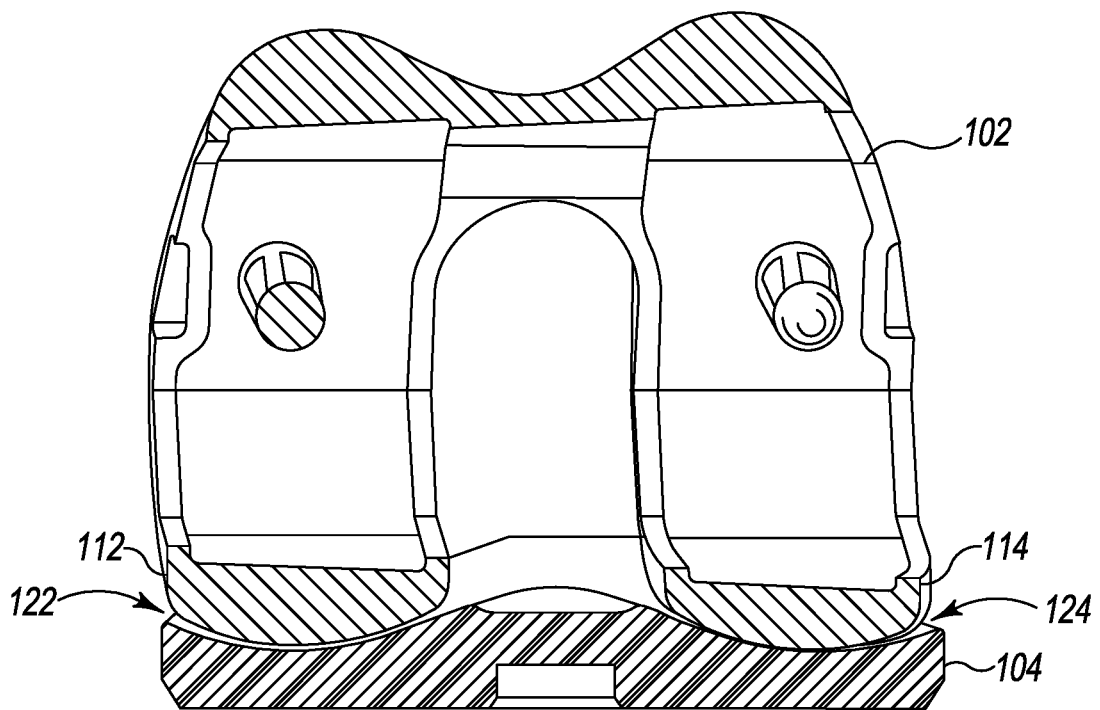
FIG. 41 is a cross-sectional view of the orthopaedic knee prosthesis of FIG. 31 in a coronal plan along the line 41-41 in FIG. 31.
Figure 42:
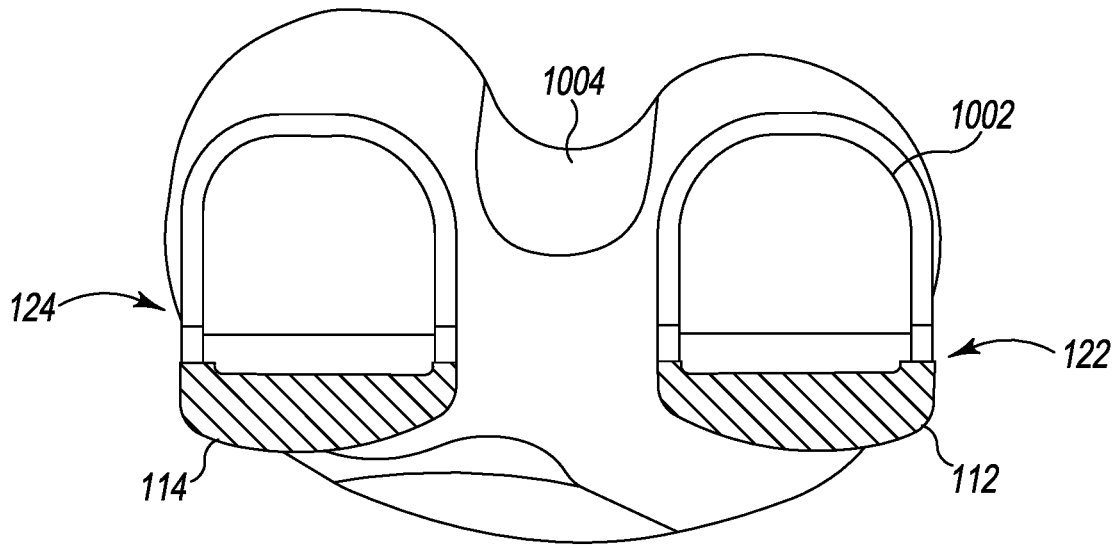
FIG. 42 is a cross-sectional view of the orthopaedic knee prosthesis of FIG. 31 in a transverse plane along the line 42-42 in FIG. 31.
Figure 43:
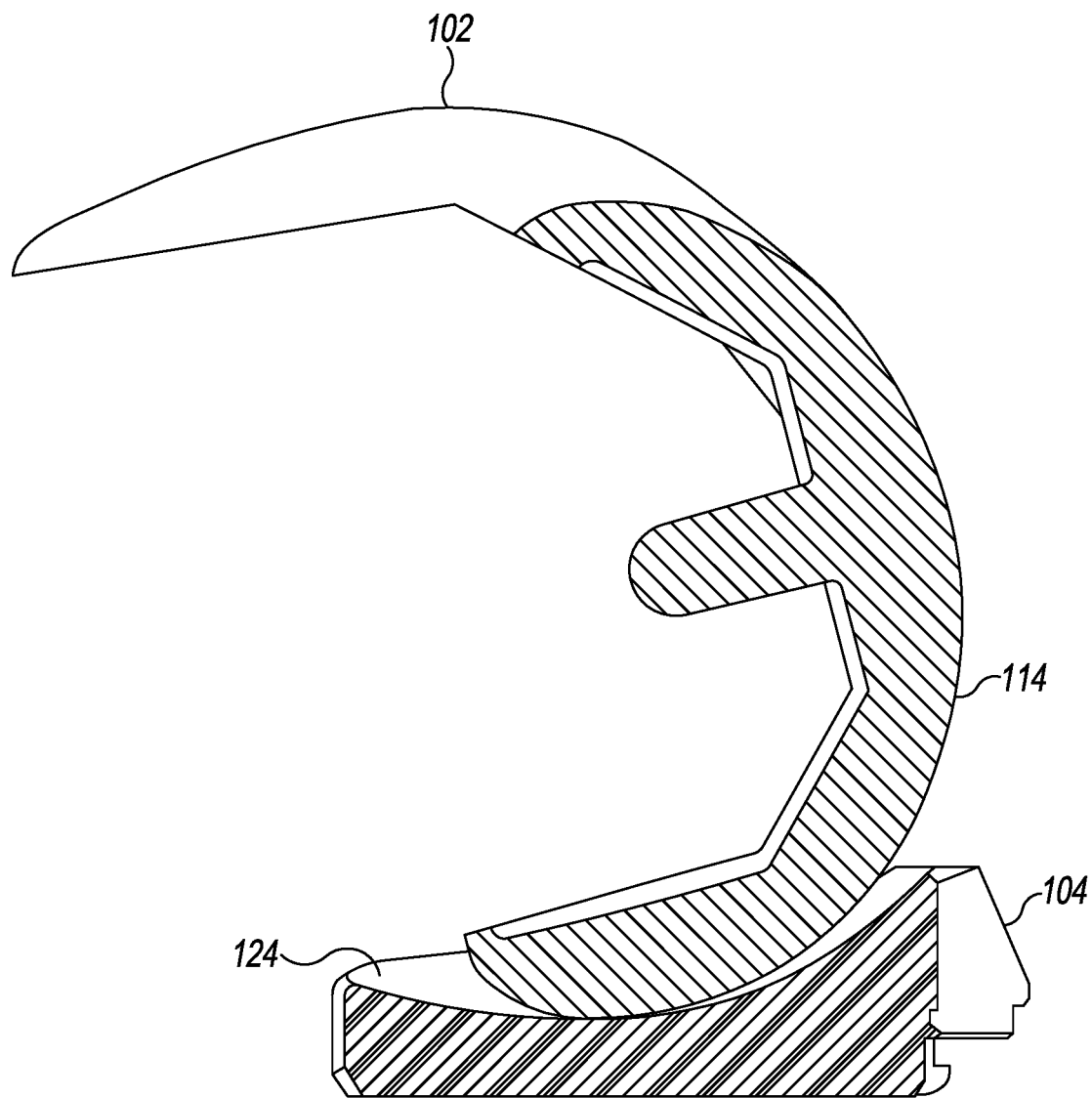
FIG. 43 is a cross-sectional view of the orthopaedic knee prosthesis of FIG. 31 in a sagittal plan along a medial dwell point of a medial articular surface of the tibial insert of the orthopaedic knee prosthesis of FIG. 31.

In FIGS. 41-43, the orthopaedic prosthesis 100 is shown at about 110 degrees of flexion. As indicated in FIG. 41, the femoral component 102 and the tibial insert 104 has less coronal conformity relative to the 90 degrees of flexion of FIGS. 38 and 39. Additionally, as shown in FIG. 42, the femoral component 102 is pivoted or rotated on the tibial insert 104 to a greater amount relative to 90 degrees of flexion of FIGS. 38 and 39. Furthermore, as shown in FIG. 43, the medial condyle 114 and the medial articular surface 124 have an overall sagittal conformity that is further decreased relative to the 90.0 degrees of flexion of FIG. 40.

Figure 44:
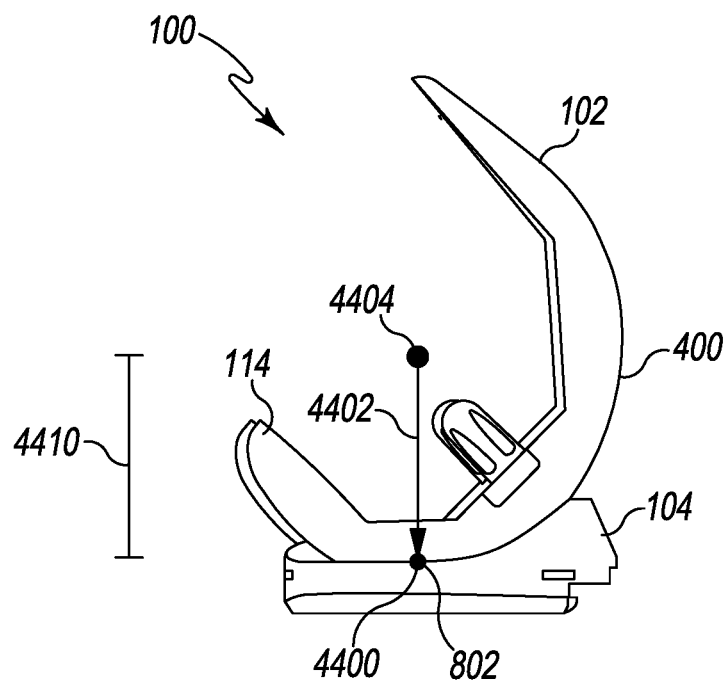
FIG. 44 is a lateral elevation view of the orthopaedic knee prosthesis of FIG. 1 flexed to a degree of flexion and showing a point of contact defined by a radius of curvature.
Figure 45:
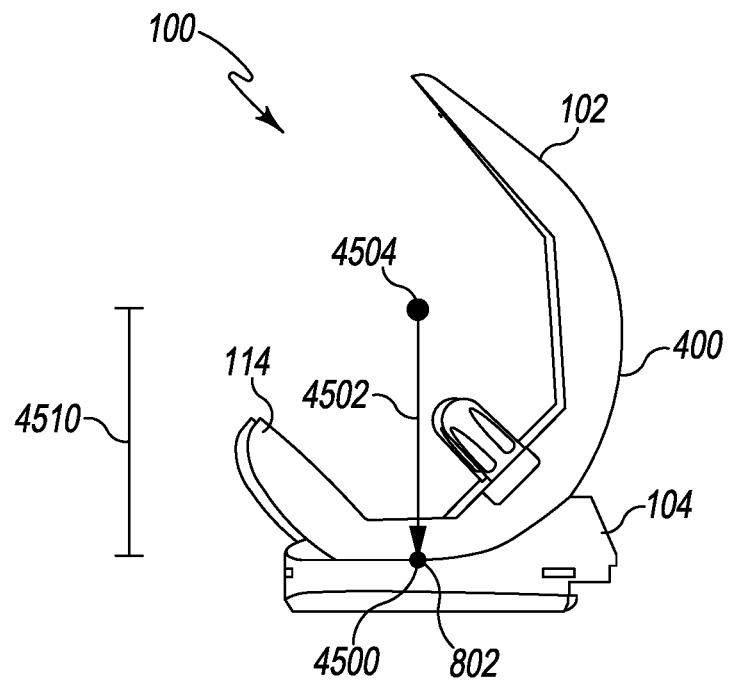
FIG. 45 is a lateral elevation view of the orthopaedic knee prosthesis of FIG. 1 flexed to a degree of flexion slightly greater than FIG. 44 and showing another point of contact defined by another radius of curvature.

Referring now to FIGS. 44 and 45, as the femoral component 102 is moved through a range of flexion, the condyle surface 400 of the medial condyle 114 contacts the medial dwell point 802 of the tibial insert 104 at different points on contact on the condyle surface 400. For example, an illustrative embodiment, as the femoral component 102 moves from about 65 degrees of flexion to a degree of flexion greater than 65 degrees, the point of contact between the femoral component 102 and the tibial insert 104 moves from the curved surface section 404 defined by the decreasing radii of curvature to the curved surface section 406 defined by a radius of curvature that is greater than the posterior-most radii of curvature of the curved surface section 404. In doing so, the distance between the origin that defines the radius of curvature of the point of contact between the femoral component 102 and the tibial insert increases.

For example, FIG. 44 illustrates the femoral component 102 at a first degree of flexion at which a point of contact 4400 between the condyle surface 400 of the medial condyle 114 of the femoral component 102 and the tibial insert 104 is located at the dwell point 802 of the tibial insert 104 and is defined by a posterior-most radii 4402 of the plurality of decreasing radii that define the curved surface section 404. The posterior-most radii 4402 has an origin 4404 that is located a distance 4410 from the medial dwell point 802.

In FIG. 45, the femoral component 102 has been moved to a second degree of flexion, slightly greater than the first degree of flexion, at which a point of contact 4500 between the condyle surface 400 of the medial condyle 114 of the femoral component 102 and the tibial insert 104 is located at the dwell point 802 of the tibial insert 104 and is defined by a constant radius of curvature 4502 that defines the curved surface section 406 (i.e., radius of curvature R3 of FIG. 4). The constant radius of curvature 4502 has an origin 4504 that is located a distance 4510 from the medial dwell point 802. It should be appreciated that the distance 4510 between the origin 4504 and the medial dwell point 802 is greater than the distance 4410 between the origin 4404 and the medial dwell point 802. As such, the increase in distance between the origins 4404, 4504 as the point of contact between the femoral component 102 and the tibial insert 104 moves from the curved surface section 404 to the curved section 406 of the condyle surface 400 of the medial condyle 114 extends the tibial-femoral envelope, which increases tension on the ligaments of the knee joint and may improve stability of the knee joint.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and/or systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. An orthopaedic knee prosthesis comprising:
   a femoral component having a lateral condyle and a medial condyle, wherein the medial condyle includes a femoral articular surface defined by a plurality of curved femoral surface sections that includes a first curved femoral surface section defined by a continually decreasing radius of curvature; and
   a tibial insert having a lateral articular surface configured to articulate with the lateral condyle of the femoral component and a medial articular surface configured to articulate with the medial condyle of the femoral component, wherein the medial articular surface is asymmetrically shaped relative to the lateral articular surface and includes a medial dwell point that defines a distal-most point on the medial articular surface,
   wherein the medial condyle contacts the medial dwell point at a first contact point on the first curved femoral surface section at a first degree of flexion and contacts the medial dwell point at a second contact point on the first curved femoral surface section at a second degree of flexion, wherein the second contact point is posterior of the first contact point and wherein the second degree of flexion is greater than the first degree of flexion, and
   wherein the medial articular surface includes a sagittal concave curvature that has a first sagittal conformity with the medial condyle at a location anterior to dwell point at the first degree of flexion and a second sagittal conformity with the medial condyle at the location anterior to the dwell point at the second degree of flexion, wherein the second sagittal conformity is greater than the first sagittal conformity to reduce anterior translation of the medial condyle at the second degree of flexion.

2. The orthopaedic knee prosthesis of claim 1, wherein the medial condyle of femoral component includes a sagittal convex curvature, and wherein a sagittal conformity between the sagittal concave curvature of the medial articular surface and sagittal concave curvature of the medial condyle is greater at a first degree of flexion of the femoral condyle than at extension.

3. The orthopaedic knee prosthesis of claim 1, wherein the medial articular surface includes a coronal concave curvature and wherein a coronal conformity between the coronal concave curvature and the medial condyle at the degree of flexion is greater at the medial dwell point of the medial articular surface than at the location on the medial articular surface that is anterior of the medial dwell point, and
   wherein the medial articular surface is non-uniform anterior of the medial dwell point and uniform posterior of the medial dwell point.

4. The orthopaedic knee prosthesis of claim 1, wherein the medial condyle and the medial articular surface are more conforming with each other than the lateral condyle and the lateral articular surface.

5. The orthopaedic knee prosthesis of claim 1, wherein the medial articular surface includes a coronal concave curvature and wherein a coronal conformity between the coronal concave curvature and the medial condyle is greater when the femoral component is positioned at extension than when the femoral component is positioned at a later degree of flexion.

6. The orthopaedic knee prosthesis of claim 1, wherein the lateral articular surface includes an arcuate articular path that when viewed in a cross-section plane has a curvature that includes a planar section, an anterior curved section located anterior of the semi-planar section, and a plurality of posterior curved sections located posterior of the planar section, and
   wherein the semi-planar section defines a distal-most area of the lateral articular surface and wherein each posterior curved section is defined by a corresponding radius of curvature, and wherein the radii of curvature of the plurality of posterior curved sections decrease posteriorly.

7. The orthopaedic knee prosthesis of claim 1, wherein the sagittal concave curvature of the medial articular surface, when viewed in a sagittal plane, includes a plurality of curved sections and wherein the medial dwell point is located on the sagittal concave curvature, and
   wherein the plurality of curved sections includes a first curved section adjacent to the medial dwell point and extending posterior therefrom, a second curved section adjacent the medial dwell point and extending anterior therefrom, a third curved section adjacent to the second curved section and extending anterior therefrom, a fourth curved section adjacent to the third curved section and extending anterior therefrom, and a fifth curved section adjacent the fourth curved section and extending anterior therefrom,
   wherein a radius of curvature of the first curved section is greater than a radius of curvature of the second curved section and wherein a radius of curvature of the third curved section is less that the radius of curvature of the second curved section, less than a radius of curvature of the fourth curved section, and less than a radius of the fifth radius of curvature.

8. The orthopaedic knee prosthesis of claim 1, wherein a distal-most point of the femoral articular surface when the femoral component is in extension defines zero degrees of flexion, and wherein the first curved femoral surface section extends from a first degree of flexion of about 5 degrees to a second degree of flexion of about 65 degrees and is defined by a plurality of rays extending from a common origin to a corresponding point on the second curved femoral surface section, and wherein each ray has a length defined by the following polynomial equation:

$$r_\theta = (a + (b*\theta) + (c*\theta^2) + (d*\theta^3)),$$

wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30 < b < 0.00$, $0.00 < b < 0.30$, and $b = 0$, wherein when b is in the range of $-0.30 < b < 0.00$, (i) c is a coefficient value between 0.00 and 0.012 and (ii) d is a coefficient value between $-0.00015$ and 0.00, wherein when b is in the range of $0 < b < 0.30$, (i) c is a coefficient value between $-0.010$ and 0.00 and (ii) d is a coefficient value between $-0.00015$ and 0.00, and wherein when b is equal to 0, (i) c is a coefficient value in a range selected from the group consisting of: $-0.0020 < c < 0.00$ and $0.00 < c < 0.0025$ and (ii) d is a coefficient value between $-0.00015$ and 0.00.

9. The orthopaedic knee prosthesis of claim 8, wherein the plurality of curved femoral surface sections includes a second curved femoral surface section posteriorly adjacent the first curved femoral section, wherein the second curved femoral surface section is defined by a constant radius of curvature greater than a posterior-most radii of curvature of the first curved femoral surface section.

10. An orthopaedic knee prosthesis comprising:
a femoral component having a lateral condyle and a medial condyle, wherein the medial condyle includes a femoral articular surface defined by a plurality of curved femoral surface sections that includes a first curved femoral surface section and a second curved femoral surface section posteriorly adjacent the first curved femoral surface section, wherein the first curved femoral surface section is defined by a continually decreasing radius of curvature and the second curved femoral surface section is defined by a constant radius of curvature greater than a posterior-most radii of curvature of the first curved femoral surface section; and
a tibial insert having a lateral articular surface configured to articulate with the lateral condyle of the femoral component and a medial articular surface configured to articulate with the medial condyle of the femoral component, wherein the medial articular surface is asymmetrically shaped relative to the lateral articular surface and includes a medial dwell point that defines a distal-most point on the medial articular surface,
wherein the medial condyle (i) contacts the medial dwell point at a first contact point on the first curved femoral surface section at a first degree of flexion, the first contact point being defined by the posterior-most radii of curvature of the first curved femoral surface section and (ii) contacts the medial dwell point at a second contact point on the second curved femoral surface section at a second degree of flexion greater than the first degree of flexion, the second contact point being defined by the constant radius of curvature of the second curved femoral surface section, and
wherein an inferior-superior distance between the medial dwell point and an origin of the constant radius of curvature of the second curved femoral surface section at the second degree of flexion is greater than an inferior-superior distance between the medial dwell point and an origin of the posterior-most radii of curvature of the first curved femoral surface section at the first degree of flexion.

11. The orthopaedic knee prosthesis of claim 10, wherein the medial condyle of femoral component includes a sagittal convex curvature and the medial articular surface includes a sagittal concave curvature, and wherein a sagittal conformity between the sagittal concave curvature of the medial articular surface and sagittal concave curvature of the medial condyle is greater at a first degree of flexion of the femoral condyle than at extension.

12. The orthopaedic knee prosthesis of claim 10, wherein the medial articular surface includes a sagittal concave curvature, wherein at the medial dwell point the sagittal concave curvature has a first sagittal conformity with the medial condyle at a first degree of flexion of the femoral component, wherein at a location on the medial articular surface that is anterior of the medial dwell point the sagittal concave curvature has a second sagittal conformity with the medial condyle at the first degree of flexion, and wherein the second sagittal conformity is greater than the first sagittal conformity.

13. The orthopaedic knee prosthesis of claim 10, wherein a distal-most point of the femoral articular surface when the femoral component is in extension defines zero degrees of flexion, and wherein the first curved femoral surface section extends from a first degree of flexion of about 5 degrees to a second degree of flexion of about 65 degrees and is defined by a plurality of rays extending from a common origin to a corresponding point on the second curved femoral surface section, and wherein each ray has a length defined by the following polynomial equation:

$$r_\theta = (a + (b*\theta) + (c*\theta^2) + (d*\theta^3)),$$

wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30 < b < 0.00$, $0.00 < b < 0.30$, and $b = 0$, wherein when b is in the range of $-0.30 < b < 0.00$, (i) c is a coefficient value between 0.00 and 0.012 and (ii) d is a coefficient value between $-0.00015$ and 0.00, wherein when b is in the range of $0 < b < 0.30$, (i) c is a coefficient value between $-0.010$ and 0.00 and (ii) d is a coefficient value between $-0.00015$ and 0.00, and wherein when b is equal to 0, (i) c is a coefficient value in a range selected from the group consisting of: $-0.0020 < c < 0.00$ and $0.00 < c < 0.0025$ and (ii) d is a coefficient value between $-0.00015$ and 0.00.

14. The orthopaedic knee prosthesis of claim 13, wherein the plurality of curved femoral surface sections includes a second curved femoral surface section posteriorly adjacent the first curved femoral section, wherein the second curved femoral surface section is defined by a constant radius of curvature greater than a posterior-most radii of curvature of the first curved femoral surface section.

15. An orthopaedic knee prosthesis comprising:
a femoral component having a lateral condyle and a medial condyle, wherein the medial condyle includes a femoral articular surface defined by a plurality of curved femoral surface sections that includes a first curved femoral surface section defined by a continually decreasing radius of curvature; and
a tibial insert having a lateral articular surface configured to articulate with the lateral condyle of the femoral component and a medial articular surface configured to articulate with the medial condyle of the femoral component,
wherein the lateral articular surface includes an arcuate articular path extending in an anterior-posterior direction, wherein the arcuate articular path when viewed in a cross-section plane has a curvature that includes a planar section and wherein the planar section defines a distal-most area of the lateral articular surface, and
wherein the medial articular surface is asymmetrically shaped relative to the lateral articular surface and includes a medial dwell point that defines a distal-most point of the medial condyle surface, and wherein the medial dwell point is located on the medial condyle surface (i) between a first imaginary medial-lateral bisecting line of the tibial insert that includes an anterior-most end of the planar section of the sagittal curvature of the lateral articular surface and a second imaginary medial-lateral bisecting line of the tibial insert that includes a posterior-most end of the planar section of the sagittal curvature of the lateral articular surface and (ii) posterior to an anterior-posterior midpoint of the planar section of the sagittal curvature of the lateral articular surface.

16. The orthopaedic knee prosthesis of claim 15, wherein the medial condyle of femoral component includes a sagittal convex curvature and the medial articular surface includes a sagittal concave curvature, and wherein a sagittal conformity between the sagittal concave curvature of the medial articular surface and sagittal concave curvature of the medial condyle is greater at a first degree of flexion of the femoral condyle than at extension.

17. The orthopaedic knee prosthesis of claim 15, wherein the medial articular surface includes a sagittal concave curvature, wherein at the medial dwell point the sagittal concave curvature has a first sagittal conformity with the medial condyle at a first degree of flexion of the femoral component, wherein at a location on the medial articular surface that is anterior of the medial dwell point the sagittal concave curvature has a second sagittal conformity with the medial condyle at the first degree of flexion, and wherein the second sagittal conformity is greater than the first sagittal conformity.

18. The orthopaedic knee prosthesis of claim 17, wherein the medial articular surface includes a coronal concave curvature, wherein at the medial dwell point the coronal concave curvature has a first coronal conformity with the medial condyle at the first degree of flexion, wherein at the location on the medial articular surface that is anterior of the medial dwell point the coronal concave curvature has a second coronal conformity with the medial condyle at the first degree of flexion, and wherein the second coronal conformity is greater than the first coronal conformity.

19. The orthopaedic knee prosthesis of claim 15, wherein a distal-most point of the femoral articular surface when the femoral component is in extension defines zero degrees of flexion, and
wherein the first curved femoral surface section extends from a first degree of flexion of about 5 degrees to a second degree of flexion of about 65 degrees and is defined by a plurality of rays extending from a common origin to a corresponding point on the second curved femoral surface section, and wherein each ray has a length defined by the following polynomial equation:

$$r_\theta = (a + (b*\theta) + (c*\theta^2) + (d*\theta^3)),$$

wherein $r_\theta$ is the length of the ray defining a point on the second curved femoral surface section at $\theta$ degrees of flexion, a is a coefficient value between 20 and 50, and b is a coefficient value in a range selected from the group consisting of: $-0.30 < b < 0.00$, $0.00 < b < 0.30$, and $b = 0$,
wherein when b is in the range of $-0.30 < b < 0.00$, (i) c is a coefficient value between 0.00 and 0.012 and (ii) d is a coefficient value between $-0.00015$ and 0.00,
wherein when b is in the range of $0 < b < 0.30$, (i) c is a coefficient value between $-0.010$ and 0.00 and (ii) d is a coefficient value between $-0.00015$ and 0.00, and
wherein when b is equal to 0, (i) c is a coefficient value in a range selected from the group consisting of: $-0.0020 < c < 0.00$ and $0.00 < c < 0.0025$ and (ii) d is a coefficient value between $-0.00015$ and 0.00.

20. The orthopaedic knee prosthesis of claim 19, wherein the plurality of curved femoral surface sections includes a second curved femoral surface section posteriorly adjacent the first curved femoral section, wherein the second curved femoral surface section is defined by a constant radius of curvature greater than a posterior-most radii of curvature of the first curved femoral surface section.

* * * * *